United States Patent
Buck et al.

(10) Patent No.: US 11,230,727 B2
(45) Date of Patent: Jan. 25, 2022

(54) DETECTION REAGENTS AND ELECTRODE ARRANGEMENTS FOR MULTI-ANALYTE DIAGNOSTIC TEST ELEMENTS, AS WELL AS METHODS OF USING THE SAME

(71) Applicant: Roche Diabetes Care, Inc., Indianapolis, IN (US)

(72) Inventors: Harvey Buck, Indianapolis, IN (US); Terry A. Beaty, Indianapolis, IN (US); Stacy Hunt DuVall, Indianapolis, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 276 days.

(21) Appl. No.: 16/375,209

(22) Filed: Apr. 4, 2019

(65) Prior Publication Data

US 2019/0233870 A1 Aug. 1, 2019

Related U.S. Application Data

(63) Continuation of application No. PCT/US2017/047048, filed on Aug. 16, 2017.
(Continued)

(51) Int. Cl.
*G01N 27/327* (2006.01)
*C12Q 1/00* (2006.01)

(52) U.S. Cl.
CPC ............. *C12Q 1/004* (2013.01); *C12Q 1/005* (2013.01); *C12Q 1/006* (2013.01);
(Continued)

(58) Field of Classification Search
CPC ................... C12Q 1/004; G01N 27/327–3272
See application file for complete search history.

(56) References Cited

U.S. PATENT DOCUMENTS 4,008,448 A  2/1977 Muggli
4,225,410 A  9/1980 Pace
(Continued)

FOREIGN PATENT DOCUMENTS

EP  0302287 A2  2/1989
EP  0354441 A2  2/1990
(Continued)

OTHER PUBLICATIONS

Hoque et al., "Strcuture of D-3-hydroxybutyrate dehydrogenase prepared in the presence of D-3-hydroxybutyrate and NAD", Acta Crystallographica Section F—Structural Biology and Crystallization Communications, Acta Cryst. (2009). F65, 331-335 (Year: 2009).*

(Continued)

*Primary Examiner* — Alexander S Noguerola
(74) *Attorney, Agent, or Firm* — Maschoff Brennan

(57) ABSTRACT

Detection reagents, multi-analyte test elements, test systems, and multi-analyte measuring methods are provided. In particular, multi-analyte test elements have (1) a first working electrode and first counter electrode pair covered with a first analyte-specific reagent that includes an enzyme, a coenzyme and a first mediator and have (2) a second working electrode covered with a second analyte-specific reagent that includes an enzyme, a coenzyme and a second mediator, where the second mediator is different than the first mediator. The single counter electrode can be used as the counter electrode for both the first and second analyte measurements at their respective working electrodes. Moreover, the mediator concentrations, measurement ranges, and applied potential differences are not the same for each analyte-specific measurement.

36 Claims, 16 Drawing Sheets

Related U.S. Application Data

(60) Provisional application No. 62/404,258, filed on Oct. 5, 2016.

(52) U.S. Cl.
 CPC ..... *G01N 27/3272* (2013.01); *G01N 27/3273* (2013.01); *G01N 27/3276* (2013.01); *G01N 27/3271* (2013.01)

(56) References Cited

U.S. PATENT DOCUMENTS

| | | |
|---|---|---|
| 4,233,029 A | 11/1980 | Columbus |
| 4,323,536 A | 4/1982 | Columbus |
| 4,720,372 A | 1/1988 | Fey et al. |
| 4,891,319 A | 1/1990 | Roser |
| 4,919,770 A | 4/1990 | Preidel et al. |
| 4,963,814 A | 10/1990 | Parks et al. |
| 4,999,582 A | 3/1991 | Parks et al. |
| 4,999,632 A | 3/1991 | Parks |
| 5,053,199 A | 10/1991 | Keiser et al. |
| 5,108,564 A | 4/1992 | Szuminsky et al. |
| 5,120,420 A | 6/1992 | Nankai et al. |
| 5,122,244 A | 6/1992 | Hoenes et al. |
| 5,128,015 A | 7/1992 | Szuminsky et al. |
| 5,206,147 A | 4/1993 | Hoenes |
| 5,243,516 A | 9/1993 | White |
| 5,271,895 A | 12/1993 | McCroskey et al. |
| 5,282,950 A | 2/1994 | Dietze et al. |
| 5,286,362 A | 2/1994 | Hoenes et al. |
| 5,288,636 A | 2/1994 | Pollmann et al. |
| 5,352,351 A * | 10/1994 | White ................ G01N 27/3273 204/403.04 |
| 5,366,609 A | 11/1994 | White et al. |
| 5,371,687 A | 12/1994 | Holmes, II et al. |
| 5,379,214 A | 1/1995 | Arbuckle et al. |
| 5,385,846 A | 1/1995 | Kuhn et al. |
| 5,393,615 A | 2/1995 | Corey et al. |
| 5,405,511 A | 4/1995 | White et al. |
| 5,413,690 A | 5/1995 | Kost et al. |
| 5,437,999 A | 8/1995 | Diebold et al. |
| 5,438,271 A | 8/1995 | White et al. |
| 5,508,171 A | 4/1996 | Walling et al. |
| 5,526,111 A | 6/1996 | Collins et al. |
| 5,594,906 A | 1/1997 | Holmes, II et al. |
| 5,627,075 A | 5/1997 | Bateson |
| 5,628,890 A | 5/1997 | Carter et al. |
| 5,682,884 A | 11/1997 | Hill et al. |
| 5,694,932 A | 12/1997 | Michel |
| 5,727,548 A | 3/1998 | Hill et al. |
| 5,762,770 A | 6/1998 | Pritchard et al. |
| 5,858,691 A | 1/1999 | Hoenes et al. |
| RE36,268 E | 8/1999 | Szuminsky et al. |
| 5,948,695 A | 9/1999 | Douglas et al. |
| 5,975,153 A | 11/1999 | Hill et al. |
| 5,997,817 A | 12/1999 | Crismore et al. |
| 6,001,239 A | 12/1999 | Douglas et al. |
| 6,004,441 A | 12/1999 | Fujiwara et al. |
| 6,025,203 A | 2/2000 | Vetter et al. |
| 6,054,039 A | 4/2000 | Shieh |
| 6,134,504 A | 10/2000 | Douglas et al. |
| 6,144,922 A | 11/2000 | Douglas et al. |
| 6,162,639 A | 12/2000 | Douglas |
| 6,207,000 B1 | 3/2001 | Schwobel et al. |
| 6,245,215 B1 | 6/2001 | Douglas et al. |
| 6,254,736 B1 | 7/2001 | Earl et al. |
| 6,270,637 B1 | 8/2001 | Crismore et al. |
| 6,271,045 B1 | 8/2001 | Douglas et al. |
| 6,319,719 B1 | 11/2001 | Bhullar et al. |
| 6,406,672 B1 | 6/2002 | Bhullar et al. |
| 6,413,213 B1 | 7/2002 | Essenpreis et al. |
| 6,413,395 B1 | 7/2002 | Bhullar et al. |
| 6,425,863 B1 | 7/2002 | Werner et al. |
| 6,428,664 B1 | 8/2002 | Bhullar et al. |
| 6,447,657 B1 | 9/2002 | Bhullar et al. |
| 6,451,264 B1 | 9/2002 | Bhullar et al. |
| 6,455,324 B1 | 9/2002 | Douglas |
| 6,488,828 B1 | 12/2002 | Bhullar et al. |
| 6,506,575 B1 | 1/2003 | Knappe et al. |
| 6,540,890 B1 | 1/2003 | Bhullar et al. |
| 6,562,210 B1 * | 5/2003 | Bhullar ................ C12Q 1/001 204/403.02 |
| 6,582,573 B2 | 6/2003 | Douglas et al. |
| 6,592,815 B1 | 7/2003 | Zimmer |
| 6,627,057 B1 | 9/2003 | Bhullar et al. |
| 6,635,167 B1 | 10/2003 | Batman et al. |
| 6,638,772 B1 | 10/2003 | Douglas et al. |
| 6,645,368 B1 | 11/2003 | Beaty et al. |
| 6,662,439 B1 | 12/2003 | Bhullar |
| 6,743,635 B2 * | 6/2004 | Neel ................ C12Q 1/006 204/403.01 |
| 6,755,949 B1 | 6/2004 | Bhullar et al. |
| 6,767,440 B1 | 7/2004 | Bhullar et al. |
| 6,780,296 B1 | 8/2004 | Bhullar et al. |
| 6,780,651 B2 | 8/2004 | Douglas et al. |
| 6,787,109 B2 | 9/2004 | Haar et al. |
| 6,814,843 B1 | 11/2004 | Bhullar et al. |
| 6,814,844 B2 | 11/2004 | Bhullar et al. |
| 6,858,433 B1 | 2/2005 | Zivitz |
| 6,866,758 B2 | 3/2005 | Bhullar et al. |
| 6,927,749 B1 | 8/2005 | Klemm |
| 6,945,955 B1 | 9/2005 | Michel et al. |
| 6,984,307 B2 | 1/2006 | Zweig |
| 7,008,799 B1 | 3/2006 | Zimmer et al. |
| 7,018,843 B2 | 3/2006 | Heller |
| 7,018,848 B2 | 3/2006 | Douglas et al. |
| 7,025,836 B1 | 4/2006 | Zimmer et al. |
| 7,045,054 B1 | 5/2006 | Buck et al. |
| 7,063,774 B2 | 6/2006 | Bhullar et al. |
| 7,067,320 B2 | 6/2006 | Klimant |
| 7,073,246 B2 | 7/2006 | Bhullar et al. |
| 7,115,362 B2 | 10/2006 | Douglas et al. |
| 7,132,270 B2 | 11/2006 | Kratzsch et al. |
| 7,208,119 B1 | 4/2007 | Kurtock et al. |
| 7,238,534 B1 | 7/2007 | Zimmer |
| 7,276,146 B2 | 10/2007 | Wilsey |
| 7,276,147 B2 | 10/2007 | Wilsey |
| 7,291,107 B2 | 11/2007 | Hellwig et al. |
| 7,312,042 B1 | 12/2007 | Petyt et al. |
| 7,335,286 B2 | 2/2008 | Abel et al. |
| 7,338,639 B2 | 3/2008 | Burke et al. |
| 7,347,973 B2 | 3/2008 | Douglas et al. |
| 7,390,667 B2 | 6/2008 | Burke et al. |
| 7,386,937 B2 | 7/2008 | Bhullar et al. |
| 7,407,811 B2 | 8/2008 | Burke et al. |
| 7,417,811 B2 | 8/2008 | Chang |
| 7,429,865 B2 | 9/2008 | Drebholz et al. |
| 7,452,457 B2 | 11/2008 | Burke et al. |
| 7,473,398 B2 | 1/2009 | Bhullar et al. |
| 7,476,827 B1 | 1/2009 | Bhullar et al. |
| 7,479,211 B2 | 1/2009 | Bhullar et al. |
| 7,488,601 B2 | 2/2009 | Burke et al. |
| 7,494,816 B2 | 2/2009 | Burke et al. |
| 7,510,643 B2 | 3/2009 | Bhullar et al. |
| 7,545,148 B2 | 6/2009 | Lorimer et al. |
| 7,547,535 B2 | 6/2009 | Kratzsch et al. |
| 7,553,615 B2 | 6/2009 | Heindl et al. |
| 7,556,723 B2 | 7/2009 | Funke et al. |
| 7,569,126 B2 | 8/2009 | Celentano et al. |
| 7,597,793 B2 | 10/2009 | Burke et al. |
| 7,601,299 B2 | 10/2009 | Beaty et al. |
| 7,638,033 B2 | 12/2009 | Kasielke et al. |
| 7,638,095 B2 | 12/2009 | Sabol |
| 7,678,250 B2 | 3/2010 | Bell et al. |
| 7,727,467 B2 | 6/2010 | Burke et al. |
| 7,731,835 B2 | 6/2010 | Buck et al. |
| 7,732,179 B2 | 6/2010 | Boenitz-Dulat et al. |
| 7,749,437 B2 | 7/2010 | Mosoiu et al. |
| 7,751,864 B2 | 7/2010 | Buck, Jr. |
| 7,771,926 B2 | 8/2010 | Petyt et al. |
| 7,780,827 B1 | 8/2010 | Bhullar et al. |
| 7,820,451 B2 | 10/2010 | Brauner |
| 7,867,369 B2 | 1/2011 | Bhullar et al. |
| 7,892,849 B2 | 2/2011 | Burke et al. |

(56) References Cited

U.S. PATENT DOCUMENTS

| | | | |
|---|---|---|---|
| RE42,560 E | 7/2011 | Crismore et al. | |
| 7,977,112 B2 | 7/2011 | Burke et al. | |
| 7,981,363 B2 | 7/2011 | Burke et al. | |
| 8,008,037 B2 | 8/2011 | Wilsey et al. | |
| RE42,924 E | 11/2011 | Crismore et al. | |
| RE42,953 E | 11/2011 | Crismore et al. | |
| 8,062,490 B2 | 11/2011 | Bell et al. | |
| 8,071,030 B2 * | 12/2011 | Bhullar | G01N 27/3272 422/82.01 |
| 8,148,164 B2 | 4/2012 | Diebold et al. | |
| 8,180,423 B2 | 5/2012 | Mang et al. | |
| 8,211,632 B2 | 7/2012 | Petyt et al. | |
| 8,226,814 B2 * | 7/2012 | Mao | C07F 15/0026 205/777.5 |
| 8,298,401 B2 | 10/2012 | Wilsey | |
| 8,298,828 B2 | 10/2012 | Diebold et al. | |
| 8,329,026 B2 | 12/2012 | Wilsey | |
| 8,377,707 B2 | 2/2013 | Burke et al. | |
| 8,420,404 B2 | 4/2013 | Diebold et al. | |
| 8,431,408 B2 | 4/2013 | Lewis et al. | |
| 8,535,511 B2 * | 9/2013 | Wilsey | C12Q 1/006 205/777.5 |
| 8,632,965 B2 | 1/2014 | Petyt et al. | |
| 8,920,628 B2 | 12/2014 | Gerber et al. | |
| 8,921,061 B2 | 12/2014 | Wilsey | |
| 8,992,750 B1 | 3/2015 | Beaty et al. | |
| 9,157,109 B2 | 10/2015 | Brennan et al. | |
| 9,218,453 B2 | 12/2015 | Groll | |
| 9,416,397 B2 | 8/2016 | Wilsey | |
| 9,594,045 B2 | 3/2017 | Buck, Jr. et al. | |
| 9,638,698 B2 | 5/2017 | Petyt et al. | |
| 9,988,358 B2 | 6/2018 | Heindl et al. | |
| 2003/0031592 A1 | 2/2003 | Knappe | |
| 2003/0146110 A1 * | 8/2003 | Karinka | C12Q 1/002 205/777.5 |
| 2003/0146113 A1 | 8/2003 | Unkrig et al. | |
| 2004/0040868 A1 | 3/2004 | DeNuzzio et al. | |
| 2006/0003397 A1 | 1/2006 | Knappe et al. | |
| 2008/0017496 A1 | 1/2008 | Thompson | |
| 2008/0101983 A1 | 5/2008 | Petyt et al. | |
| 2008/0156662 A1 * | 7/2008 | Wu | G01N 33/49 205/787 |
| 2008/0179197 A1 * | 7/2008 | Wu | G01N 27/3274 205/775 |
| 2009/0186372 A1 | 7/2009 | Bell et al. | |
| 2009/0210249 A1 | 8/2009 | Rasch-Menges et al. | |
| 2009/0246808 A1 | 10/2009 | Wilsey et al. | |
| 2010/0227355 A1 | 9/2010 | Bell et al. | |
| 2010/0267161 A1 * | 10/2010 | Wu | C12Q 1/001 436/149 |
| 2011/0048972 A1 * | 3/2011 | Moffat | C12Q 1/001 205/792 |
| 2011/0099786 A1 | 5/2011 | Petyt et al. | |
| 2012/0053429 A1 | 3/2012 | Trepagnier et al. | |
| 2013/0031772 A1 | 2/2013 | Petyt et al. | |
| 2014/0124384 A1 * | 5/2014 | Gerber | G01N 27/416 205/782 |
| 2014/0127728 A1 | 5/2014 | Wilsey | |
| 2014/0127821 A1 | 5/2014 | Petyt et al. | |
| 2014/0212903 A1 | 7/2014 | Duvall et al. | |
| 2014/0322737 A1 | 10/2014 | Horn et al. | |
| 2014/0363835 A1 | 12/2014 | Chemnitius et al. | |
| 2015/0140584 A1 | 5/2015 | Wilsey | |
| 2015/0362455 A1 | 12/2015 | Moore et al. | |
| 2016/0010141 A1 * | 1/2016 | Gaessler-Dietsche | C12Q 1/54 435/26 |
| 2016/0011140 A1 | 1/2016 | Buck, Jr. et al. | |
| 2017/0226068 A1 | 8/2017 | Heindl et al. | |
| 2017/0276685 A1 | 9/2017 | Petyt et al. | |

FOREIGN PATENT DOCUMENTS

| | | | |
|---|---|---|---|
| EP | 0431456 A2 | 6/1991 | |
| EP | 0547710 A2 | 6/1993 | |
| EP | 0620283 A1 | 10/1994 | |
| EP | 0654079 A1 | 5/1995 | |
| EP | 0831327 A1 | 3/1998 | |
| EP | 1457572 A1 | 9/2004 | |
| EP | 1593434 A2 | 11/2005 | |
| EP | 1780288 A1 | 5/2007 | |
| EP | 2292785 A1 | 3/2011 | |
| JP | H07310194 A | 11/1995 | |
| JP | 2005530179 A | 10/2005 | |
| JP | 2011053211 A | 3/2011 | |
| JP | 2011510301 A | 3/2011 | |
| JP | 2012211916 A | 11/2012 | |
| JP | 2015536138 A | 12/2015 | |
| JP | 2016510123 A | 4/2016 | |
| JP | 2016105092 A | 6/2016 | |
| JP | 2017517480 A | 6/2017 | |
| WO | 1998033936 A1 | 8/1998 | |
| WO | 1998035225 A1 | 8/1998 | |
| WO | WO 99/30152 A1 * | 6/1999 | G01N 33/48 |
| WO | 2001049247 A2 | 7/2001 | |
| WO | 2001060248 A1 | 8/2001 | |
| WO | 2005045016 A2 | 5/2005 | |
| WO | 2007012494 A1 | 2/2007 | |
| WO | 2009015870 A1 | 2/2009 | |
| WO | 2009103540 A1 | 8/2009 | |
| WO | 2010094426 A1 | 8/2010 | |
| WO | 2010094427 A2 | 8/2010 | |
| WO | 2010094632 A1 | 8/2010 | |
| WO | 2011012269 A2 | 2/2011 | |
| WO | 2011012270 A1 | 2/2011 | |
| WO | 2011012271 A2 | 2/2011 | |
| WO | 2011020856 A1 | 2/2011 | |
| WO | 2012010308 A1 | 1/2012 | |
| WO | 2012089523 A1 | 7/2012 | |
| WO | 2012089524 A1 | 7/2012 | |
| WO | 2012139767 A1 | 10/2012 | |
| WO | 2013017218 A1 | 2/2013 | |
| WO | 2013131885 A1 | 9/2013 | |
| WO | 2014037372 A1 | 3/2014 | |
| WO | 2014068022 A1 | 5/2014 | |
| WO | 2014068024 A1 | 5/2014 | |
| WO | WO 2014128271 * | 8/2014 | G01N 33/535 |
| WO | 2014140164 A1 | 9/2014 | |
| WO | WO 2014/140170 A1 * | 9/2014 | G01N 27/327 |
| WO | 2014140172 A1 | 9/2014 | |
| WO | 2014140173 A1 | 9/2014 | |
| WO | 2014140177 A2 | 9/2014 | |
| WO | 2014140178 A1 | 9/2014 | |
| WO | 2014140718 A2 | 9/2014 | |
| WO | 2015057933 A1 | 4/2015 | |
| WO | 2015158645 A1 | 10/2015 | |
| WO | 2015187580 A1 | 12/2015 | |
| WO | 2016030346 A2 | 3/2016 | |
| WO | 2016174458 A1 | 11/2016 | |
| WO | 2016174460 A1 | 11/2016 | |
| WO | 2017167815 A1 | 10/2017 | |

OTHER PUBLICATIONS

Office Action dated Apr. 28, 2020 in JP Application No. 2019-518202; 6 pages.

International Search Report and Written Opinion dated Nov. 6, 2017 in International Patent Application No. PCT/US2017/047048.

Mansson et al. "Covalent Binding of an NAD Analogue to Liver Alcohol Dehydrogenase Resulting in an Enzyme-Coenzyme Complex not Requiring Exogenous Coenzyme for Activity," Eur. J. Biochem., May 16, 1978 (May 16, 1978), vol. 86, pp. 455-463.

McKenzie et al. "Real-Time Monitoring of Cellular Bioenergetics with a Multi-Analyte Screen-Printed Electrode," Anal Chem, Aug. 4, 2015 (Aug. 4, 2015), vol. 87, pp. 7857-7864.

Baik et al. (2005), "Cooperative Effect of Two Surface Amino Acid Mutations (Q252L and E170K) in Glucose Dehydrogenase from Bacillus megaterium IWG3 on Stabilization of Its Oligomeric State", Appl. Environ. Microbiol. 71:3285-3293.

Baldwin (1983), "Phenylenediamine-Containing Chemically Modified Carbon Paste Electrodes as Catalytic Voltammetric Sensors", Anal. Chem. 55:1588-1591.

(56) References Cited

OTHER PUBLICATIONS

Degrand & Miller (1980), "An Electrode Modified with Polymer-Bound Dopamine Which Catalyzes NADH Oxidation", J. Am. Chem. Soc. 102:5728-5732.

Gorton & Dominguez (2002), "Electrocatalytic oxidation of NAD(P)H at mediator-modified electrodes", Rev. Mol. Biotechnol. 82:371-392.

Gorton (1986), "Chemically Modified Electrodes for the Electrocatalytic Oxidation of Nicotinamide Coenzymes", Chem. Soc., Faraday Trans. 1 82:1245-1258.

Habermüller et al. (2000), "Electron-transfer mechanisms in amperometric biosensors", Fresenius J. Anal. Chem. 366:560-568.

Heller et al. (2008), "Electrochemical Glucose Sensors and Their Applications in Diabetes Management", Chem. Rev. 108:2482-2505.

Huang et al. (2014), "Evaluation of accuracy of FAD-GDH—and mutant Q-GDH-based blood glucose monitors in multi-patient populations", Clin. Chim. Acta. 433:28-33.

Hutchinson et al. (1996), "Synthesis of carbocyclic NAD+ containing a methylenebisphosphonate linkage for the investigation of ADP-ribosyl cyclase", Chem. Commun. 24:2765-2766.

Hönes et al. (2008), "The Technology Behind Glucose Meters: Test Strips", Diabetes Technol. Ther. 10:S10-S26.

Kitani & Miller (1981), "Fast Oxidants for NADH and Electrochemical Discrimination between Ascorbic Acid adn NADH", J. Am. Chem. Soc. 103:3595-3597.

Pickup et al. (2005), "Fluorescence-based glucose sensors", Biosens. Bioelectron. 20:2555-2565.

Slama & Simmons (1988), "Carbanicotinamide Adenine Dinucleotide: Synthesis and Enzymological Properties of a Carbocyclic Analogue of Oxidized Nicotinamide Adenine Dinucleotide", Biochem. 27:183-193.

Slama & Simmons (1989), "Inhibition of NAD Glycohydrolase and ADP-ribosyl Transferases by Carbocyclic Analogues of Oxidized Nicotinamide Adenine Dinucleotide", Biochem. 28:7688-7694.

Vásquez-Figueroa et al. (2007), "Development of a Thermostable Glucose Dehydrogenase by a Structure-Guided Consensus Concept", ChemBioChem 8:2295-2301.

McKenzie et al., "Real-Time Monitoring of Cellular Bioenergetics with a Multi-Analyte Screen-Printed Electrode", Anal Chem, Aug. 4, 2015, p. 7857-7864, vol. 87.

\* cited by examiner

DETECTION REAGENTS AND ELECTRODE ARRANGEMENTS FOR MULTI-ANALYTE DIAGNOSTIC TEST ELEMENTS, AS WELL AS METHODS OF USING THE SAME

CROSS-REFERENCE TO RELATED APPLICATIONS

This patent application claims priority to and the benefit of U.S. Provisional Patent Application No. 62/404,258 (filed 5 Oct. 2016), and is a Continuation of International Patent Application No. PCT/US2017/047048 (filed 16 Aug. 2017). The contents of these applications are incorporated herein by reference in their entirety.

TECHNICAL FIELD

This disclosure relates generally to chemistry, engineering, and medicine/medical diagnostics, and more particularly, it relates to detection reagents and electrode arrangements for multi-analyte diagnostic test elements, as well as multi-analyte analysis methods using the same.

BACKGROUND

Disposable diagnostic test elements have become commonplace for analyzing selected analytes in body fluid samples (i.e., detecting presence and/or measuring concentration thereof). For example, persons with diabetes typically engage in daily self-monitoring of at least blood glucose concentration. After determining a blood glucose concentration, it may necessary for such a person to take corrective action to bring the blood glucose concentration back within an acceptable range if it is too high or too low, as failure to take corrective action can have serious medical implications. As such, daily self-monitoring of blood glucose concentration is an everyday occurrence for persons with diabetes, and the accuracy of such monitoring can mean the difference between life and death. Failing to maintain blood glucose concentration in the acceptable range on a regular basis can result in serious diabetes-related complications including, but not limited to, cardiovascular disease, kidney disease, nerve damage and blindness.

A number of analytical systems, such as test meters and associated diagnostic test elements, are available that permit a person to electrochemically or optically measure glucose concentration in body fluid samples. In current test meters, the information displayed following a successful blood glucose test is the respective blood glucose concentration, typically shown in mg/dL or mmol/L (mM), and perhaps the time and date the measurement was performed. This information, in combination with calculation of planned/known intake of carbohydrates and/or planned/known activities and/or knowledge of other situational or individual factors, is in most cases sufficient to allow a person with diabetes to adjust or derive his or her dietary intake and/or an immediate dose of insulin to avoid or attenuate hyperglycemia in the short term. Also, in case of a low glucose concentration, the person with diabetes can detect a need for an intake of sugar to avoid hypoglycemia.

An absence or insufficient amount of insulin prevents the body from using glucose as a fuel source to produce energy. When this occurs, the body uses an alternative fuel source and produces energy by breaking down fatty acids, which results in ketone byproducts and increased ketone concentrations. Likewise, increased ketone concentrations in a person with diabetes may be caused by a heart attack, stroke, recreational drug usage, or an intercurrent illness such as pneumonia, influenza, gastroenteritis or a urological infection.

Excessive ketone concentrations in persons with diabetes can lead to diabetic ketoacidosis (DKA), which is a medical emergency that may lead to death if not treated. Preventing DKA can be achieved by measuring ketone concentrations and seeking medical attention if ketone concentrations rise above a certain threshold. The American Diabetes Association (ADA) recommends that ketone concentrations should be checked every 4-6 hours when a person with diabetes has an illness (such as a cold or the flu) or when a person with diabetes has a blood glucose concentration of more than 240 mg/dL (available on the World Wide Web at diabetes.org/living-with-diabetes/complications/ketoacidosis-dka.html).

Ketones typically are measured in the urine and/or blood. However, for persons with diabetes who perform multiple blood glucose tests per day, performing separate urine and/or blood ketone tests in addition to their blood glucose tests is time consuming and burdensome. Moreover, using separate tests for determining a ketone concentration also requires additional diagnostic supplies and its attendant costs, which makes it difficult to correlate glucose and ketone concentrations.

More recently, systems and methods have been developed for determining both blood glucose and blood ketone concentrations in a single test via multi-analyte diagnostic test elements. In these multi-analyte test elements, however, blood glucose tests are completed more quickly than blood ketone test such that displaying of blood ketone concentration is delayed and thus provided after the blood glucose concentration. See, e.g., U.S. Pat. No. 6,984,307. Alternatively, both the blood glucose and blood ketone concentrations are delayed until the blood ketone test is completed.

In either case, waiting for the results of one or both tests until the blood ketone test is completed can be quite burdensome and time consuming for a person with diabetes who performs a relatively high number of such tests each day, particularly when considering that in some instances the blood ketone test can take almost twice as long to complete as the blood glucose test. Moreover, when blood glucose concentration is provided before and separate from blood ketone concentration, a possibility arises for the person to discontinue testing before the blood ketone test is completed and/or divert attention elsewhere after the blood glucose test results have been provided but before the results of the blood ketone test have been properly considered.

A recent advance in multi-analyte testing is improved ketone reagent formulations that permit both blood ketone and blood glucose concentrations to be provided within 7.5 seconds or less after contacting a test element with a body fluid sample and even within seconds of one another. See, e.g., Int'l Patent Application Publication No. WO 2014/068022. Another advance in multi-analyte testing includes a "ketone watch," which may be initiated when a blood glucose concentration is at a certain predetermined value to trigger an analysis of ketone trends, as well as automatically providing blood ketone concentration with blood glucose concentration if glucose and/or ketone concentrations are above a predetermined value. See, e.g., Int'l Patent Application Publication No. WO 2014/068024. Alternatively, the ketone watch may be started if a person indicates that he or she has an illness such as a cold or the flu. See, id.

Current multi-analyte test elements, however, require complete detection reagents for each analyte of interest, as well as separate pairs of working and counter electrodes for each analyte of interest.

While known methods and systems provide many advantages with respect to separately measuring glucose and ketone concentrations, there remains a need for additional systems and methods of simultaneously measuring glucose and ketone concentrations on the same diagnostic test element.

BRIEF SUMMARY

An inventive concept described herein includes using particular combinations of mediators in multi-analyte detection reagents so that a single counter electrode (CE) can be used with a plurality of analyte-specific working electrodes (WEs). This inventive concept is achieved by providing a multi-analyte diagnostic test element having a first WE and first CE pair covered with a first analyte-specific detection reagent that includes a first mediator and also having a second WE covered with a second analyte-specific detection reagent that includes a second mediator. In this manner, the single CE can be used as the CE for both the first and second analyte measurements at their respective WEs. Moreover, the mediator concentrations, measurement ranges, applied potential differences, and sequence in which such potential differences are applied to a sample may vary for each analyte-specific measurement. Stated differently, the inventive concept includes using detection reagents for at least two different analytes, where one detection reagent includes a first mediator that provides the WE and CE function for one analyte measurement, and where the same CE also provides the CE function for any other analyte measurements at other WEs having their own analyte-specific detection reagent including a mediator that is distinct from the first mediator. This inventive concept therefore can be incorporated into exemplary dry detection reagents, multi-analyte diagnostic test elements, test systems, and multi-analyte measuring methods as described herein and in more detail below.

For example, detection reagents are provided for multi-analyte analysis that include a first detection reagent for a first analyte of interest and a second detection reagent for a second analyte of interest.

The first detection reagent includes a first coenzyme-dependent enzyme or a substrate for the first enzyme, a first coenzyme, and a first mediator. In some instances, the first coenzyme-dependent enzyme and the first coenzyme are attached, bound, integrated or linked to one another.

The first coenzyme-dependent enzyme can be an oxidase or a dehydrogenase. In some instances, the first coenzyme-dependent enzyme is a flavin adenine dinucleotide (FAD)-, nicotinamide adenine dinucleotide (NAD)-, or pyrroloquinoline-quinone (PQQ)-dependent dehydrogenase, especially a FAD-, NAD- or PQQ-dependent dehydrogenase, as well as enzymatically active mutants thereof. In other instances, the first coenzyme-dependent enzyme is a glucose dehydrogenase, a glucose-6-phospate dehydrogenase, or a glucose oxidase, as well as enzymatically active mutants thereof.

Likewise, the first coenzyme can be a FAD, a NAD, a nicotinamide adenine dinucleotide phosphate (NADP), a thio-NAD, a thio-NADP, a PQQ, or an artificial coenzyme such as a compound according to formula (I) or a salt or a reduced form thereof. In some instances, the first coenzyme is FAD, NAD, NADP, or the compound according to formula (I) or a salt or optionally a reduced form thereof. In other instances, the first coenzyme is FAD.

Moreover, the first mediator can be an azo compound or an azo precursor, benzoquinone, meldola blue, a nitrosoaniline or a nitrosoaniline-based precursor, a phenazine or a phenazine-based precursor, a quinone or a quinone derivative, a thiazine or a thiazine derivative, a transition metal complex such as potassium ferricyanide and osmium derivatives, or a combination of a phenazine/phenazine-based precursor and hexaammineruthenium chloride, as well as derivatives thereof. In some instances, the first mediator is a nitrosoaniline derivative or nitrosoaniline-based precursor, ferricyanide, ruthenium hexamine, or phenazine. In other instances, the first mediator is N,N-bis(hydroxyethyl)-3-methoxy-4-nitrosoaniline hydrochloride (called BM 31.1144 or NA1144; Roche Diagnostics, Inc.; Indianapolis, Ind. USA).

Thus, an exemplary first detection reagent can include a FAD-dependent glucose dehydrogenase as the enzyme; FAD as the coenzyme; and a nitrosoaniline-based precursor as the mediator, such as NA1144.

The second detection reagent likewise includes a second coenzyme-dependent enzyme or a substrate for the second enzyme, a second coenzyme, and a second mediator, where the second mediator may be distinct from the first mediator (i.e., the second mediator may not be the same as the first mediator). In some instances, the second coenzyme-dependent enzyme and the second coenzyme are attached, bound, integrated or linked to one another.

The second coenzyme-dependent enzyme can be an oxidase or a dehydrogenase. In some instances, the second coenzyme-dependent enzyme can be a FAD-, NAD- or PQQ-dependent dehydrogenase, especially a FAD-, NAD- or PQQ-dependent dehydrogenase, as well as enzymatically active mutants thereof. In other instances, the second coenzyme-dependent enzyme can be an alcohol dehydrogenase, a glucose dehydrogenase, a glucose-6-phosphate dehydrogenase, a glucose oxidase, a glycerol dehydrogenase, a hydroxybutyrate dehydrogenase (HBDH), a malate dehydrogenase, a sorbitol dehydrogenase, or an amino acid dehydrogenase comprising L-amino acid dehydrogenase, as well as enzymatically active mutants thereof. In certain instances, the second coenzyme-dependent enzyme is a HBDH such as 3-HBDH, as well as enzymatically active mutants thereof. Alternatively, the second coenzyme-dependent enzyme can be the same enzyme as the first coenzyme-dependent enzyme.

Likewise, the second coenzyme can be a FAD, a NAD, a NADP, a thio-NAD, a thio-NADP, a PQQ, or an artificial coenzyme such as a compound according to formula (I) or a salt or a reduced form thereof. In some instances, the second coenzyme is thio-NAD, thio-NADP, or a compound according to formula (I) or a salt or a reduced form thereof. In other instances, the second coenzyme is carba-NAD, carba-NADP, thio-NAD, or thio-NADP.

Moreover, the second mediator can be an azo compound or an azo precursor, benzoquinone, meldola blue, a nitrosoaniline or a nitrosoaniline-based precursor, a phenazine or a phenazine-based precursor, a phenoxazine, a phenothiazine, a quinone or a quinone derivative, a thiazine or a thiazine derivative, a transition metal complex such as potassium ferricyanide and osmium derivatives, or a combination of a phenazine/phenazine-based precursor and hexaammineruthenium chloride, as well as derivatives thereof. In some instances, the second mediator is medola blue, a phenazine or phenazine-based precursor, or a quinone or a quinone derivative. In other instances, the second mediator is a phenazine derivative such as name 1-(3-carboxy-propionylamino)-5-ethyl-phenazin-5-ium (PG355).

When the first analyte is glucose, the second analyte can be an analyte related to free fatty acid metabolism such as free fatty acids, ketones, glycerol or any other analyte representative of lipolysis, especially ketones and ketone bodies. Thus, an exemplary second detection reagent can include a HBDH as the enzyme; a carba-NAD, carba-NADP, thio-NAD or thio-NADP as the coenzyme; and a phenazine/phenazine-based precursor as the mediator, such as PG355. More specifically, the second detection reagent can be 3-HBDH, carba-NAD and PG355.

Alternatively, and when the first and second analytes are the same analyte such as glucose, an exemplary second detection reagent can include a FAD-dependent glucose dehydrogenase as the enzyme; FAD as the coenzyme; and a ferricyanide or a nitrosoaniline other than NA1144 as the mediator.

In addition, multi-analyte diagnostic test elements are provided that include a non-conductive base substrate having thereupon a first electrode system in communication with a first detection reagent as described herein and a second electrode system in communication with a second detection reagent as described herein. The first electrode system includes a CE and WE pair, as well as related conductive traces and contact pads. Likewise, the second electrode system includes a WE, as well as a related conductive trace and contact pad. In some instances, additional electrode systems and detection reagents for other analytes can be included provided that the additional detection reagents have a mediator different than the mediator in the first detection reagent. In other instances, the additional electrode systems also include sample sufficiency electrodes and/or integrity electrodes.

Moreover, systems are provided that include (1) a test meter configured to analyze a body fluid sample and (2) one or more multi-analyte diagnostic test elements as described herein. The meter is adapted to receive the multi-analyte test elements and thus includes a controller configured to provide a test sequence and to determine concentration of one or more analytes in the body fluid sample based upon response information obtain from the multi-analyte test elements. To assist in conveying test results to a user, the meter also can include one or more input devices and/or output devices.

In view of the foregoing, multi-analyte analysis methods are provided that include applying or contacting a multi-analyte diagnostic test element as described herein with a body fluid sample; applying an electrical test sequence to the body fluid sample to obtain response information relating to each analyte of interest; determining a first analyte concentration in the sample from respective response information to the test sequence, determining a second analyte concentration in the sample from respective response information to the test sequence, and displaying information to a user regarding one or both analyte concentrations. The methods optionally can include determining additional analyte concentrations when additional working electrodes and detection reagents are provided on the test element. The methods also optionally can include adjusting a treatment (e.g., insulin) or modifying a diet based upon the one or more analyte concentrations. The methods also optionally also can include transmitting a message to at least one of a user of the test element, healthcare provider, caregiver, and parent or guardian to adjust a treatment or modify a diet based upon the one or more analyte concentrations.

In some instances, both analyte concentrations are displayed to a user; however, in other instances, only one analyte concentration is displayed, while the other analyte concentration is displayed only if a predetermined threshold or condition for one analyte, the other analyte, or both analytes is met. In certain instances, the first analyte is glucose and the second analyte is ketone, where the glucose concentration is displayed to the user and the ketone concentration is displayed only of the predetermined threshold(s) or condition(s) is/are met, and where the predetermined threshold(s) or condition(s) can be a glucose concentration of about 240 mg/dL or a ketone concentration from about 0.6 mM to about 3.0 mM or even from about 0.6 mM to about 1.5 mM.

In other instances, the methods can include a step of displaying information to a user when the predetermined threshold(s) or condition(s) is/are met such as at least one of displaying the second analyte concentration, providing a warning, providing a list of actions to take in response to the second analyte concentration being above the predetermined value, or transmitting a message to at least one of a user of the test element, healthcare provider, caregiver, and parent or guardian.

In summary, detection reagents, multi-analyte diagnostic test elements, test systems and multi-analyte measuring methods are provided that can be used to determine concentration of a number of analytes including, but not limited to, amino acids, antibodies, bacteria, carbohydrates, drugs, lipids, markers, nucleic acids, peptides, proteins, toxins, viruses and other analytes, as well as combinations thereof.

These and other advantages, effects, features and objects of the inventive concept will become better understood from the description that follows. In the description, reference is made to the accompanying drawings, which form a part hereof and in which there is shown by way of illustration, not limitation, embodiments of the inventive concept.

BRIEF DESCRIPTION OF THE DRAWINGS

The advantages, effects, features and objects other than those set forth above will become more readily apparent when consideration is given to the detailed description below. Such detailed description makes reference to the following drawings, wherein:

FIG. 4A shows an exemplary test sequence having two direct current (DC) components for multi-analyte measurements (left panel) and an exemplary current response thereto (right panel). FIG. 4B shows an exemplary test sequence having two DC components preceded by a rest component for multi-analyte measurements (left panel) and an exemplary current response thereto (right panel).

FIG. 4C shows an exemplary test sequence having a first rest component, a first DC component, a second rest component, and a second DC component for multi-analyte measurements (left panel) and an exemplary current response thereto (right panel).

FIG. 4D shows an exemplary test sequence having a first rest component, a first DC component that is pulsed, and a second DC component for multi-analyte measurements (left panel) and an exemplary current response thereto (right panel). FIG. 4E shows an exemplary test sequence having an initial rest component, an alternating current (AC) component, a first DC component that is pulsed, a second DC component that is pulsed differently from the first DC component, and a third DC component for secondary analyte measurements (left panel) and an exemplary current response thereto (right panel). FIG. 4F shows an exemplary test sequence having a rest component, an AC component, a first DC component that is pulsed, a second DC component that is pulsed differently from the first DC component, and a third DC component that is pulsed differently from the first and the second DC components for multi-analyte measurements (left panel) and an exemplary current response thereto (right panel).

FIG. 6A shows impact on the glucose current in the presence of different levels of 3-HB (0 mM, 1 mM, 3 mM, and 8 mM). Two glucose levels were tested (0 mg/dL and 300 mg/dL), each with the different levels of 3-HB. FIG. 6B shows impact on 3-HB current in the presence of different levels of glucose (0 mg/dL and 300 mg/dL). Four different levels of 3-HB (0 mM, 1 mM, 3 mM, and 8 mM) were tested, each with the different levels of glucose.

FIG. 7A shows dose-response curves of NAD and cNAD in which test elements were dosed with samples containing 3-HB with varying concentrations (0 mM, 1 mM, 2 mM, 3 mM, and 4 mM). FIG. 7B shows dose-response curves of NAD and cNAD in which test elements having the ketone detection reagent and a glucose detection reagent were dosed with samples containing glucose with varying concentrations (0 mg/dL, 57 mg/dL, 123 mg/dL, 520 mg/dL, and 1000 mg/dL).

FIG. 9A shows 3-HB current in the presence of glucose with wild-type HBDH; FIG. 9B shows 3-HB current in the presence of glucose with an AFDH3 HBDH mutant; FIG. 9C shows 3-HB current in the presence of glucose with an AFDH4 HBDH mutant; FIG. 9D shows glucose current in the presence of glucose with wild-type HBDH; FIG. 9E shows glucose current in the presence of glucose with the AFDH3 HBDH mutant; and FIG. 9F shows glucose current in the presence of glucose with the AFDH4 HBDH mutant.

FIG. 10A shows impact on the glucose current in the presence of different levels of 3-HB. FIG. 6B shows impact on 3-HB current. Five different levels of 3-HB (0 mM, 0.5 mM, 1.5 mM, 4 mM, and 8 mM) were tested, each with the different levels of glucose.

FIG. 11A shows impact on the 3-HB current in the presence of different levels of glucose (0 mg/dL, 150 mg/dL, and 300 mg/dL). Three different levels of 3-HB (0.5 mM, 1.5 mM, and 3 mM) were tested, each with the different levels of glucose. FIG. 11B shows impact on glucose current in the presence of different levels of glucose 3-HB (0.5 mM, 1.5 mM, and 3 mM). Three glucose levels were tested (0 mg/dL, 150 mg/dL, and 300 mg/dL), each with the different levels of 3-HB.

FIG. 12A shows response of an electrode having a detection reagent with a mutant PQQ-GDH with low maltose sensitivity. No significant xylose response was seen with the mutant PQQ-GDH electrode. FIG. 12B shows response of an electrode having a detection reagent with FAD-GDH.

Corresponding reference characters indicate corresponding parts throughout the several views of the drawings.

Figure 1:
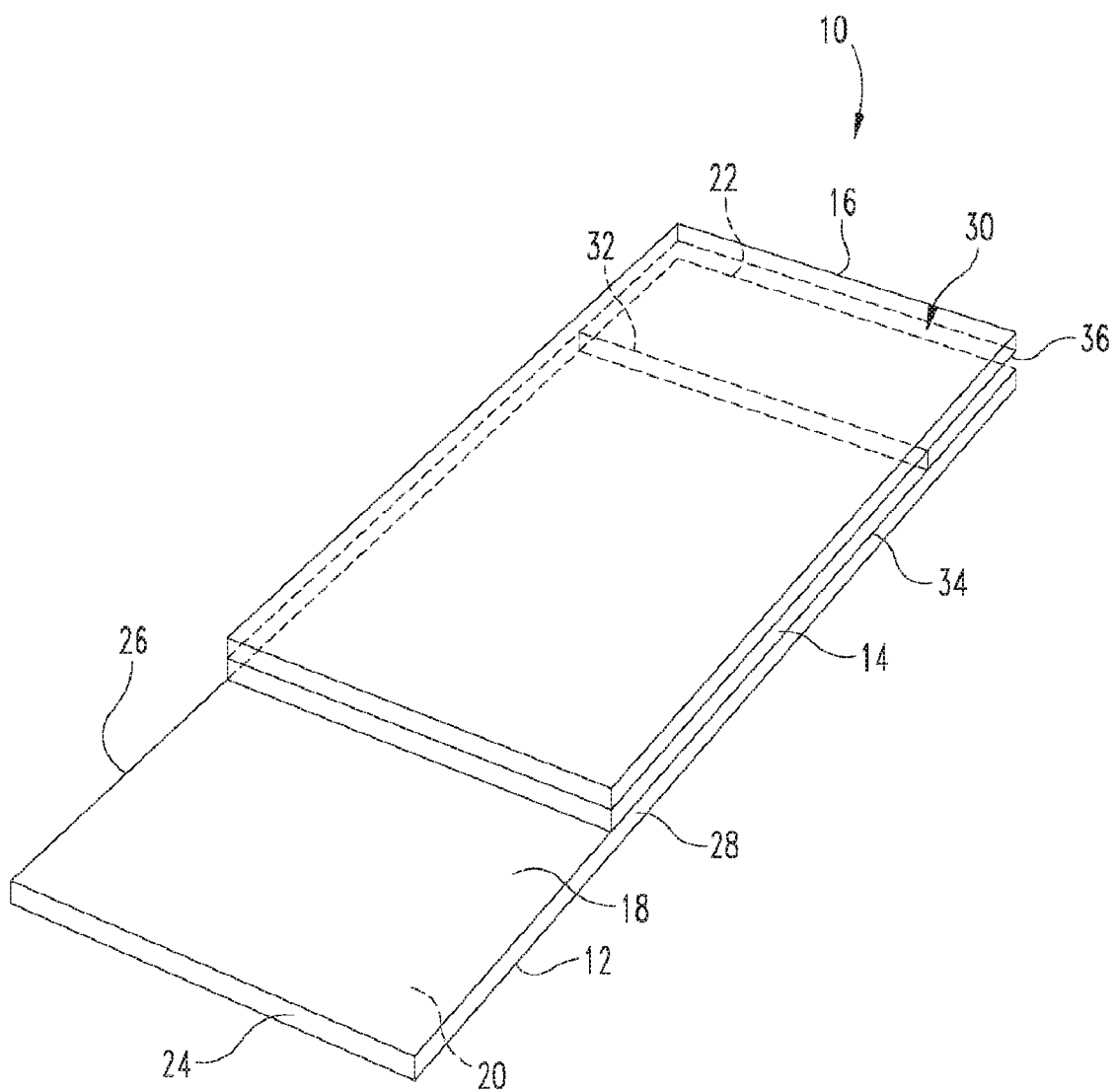
FIG. 1 shows an exemplary test element configuration.

While the inventive concept is susceptible to various modifications and alternative forms, exemplary embodiments thereof are shown by way of example in the drawings and are herein described in detail. It should be understood, however, that the description of exemplary embodiments that follows is not intended to limit the inventive concept to the particular forms disclosed, but on the contrary, the intention is to cover all advantages, effects, features and objects falling within the spirit and scope thereof as defined by the embodiments described herein and the claims below. Reference should therefore be made to the embodiments described herein and claims below for interpreting the scope of the inventive concept. As such, it should be noted that the embodiments described herein may have advantages, effects, features and objects useful in solving other problems.

DESCRIPTION OF EXEMPLARY EMBODIMENTS

The detection reagents, multi-analyte diagnostic test elements, test systems and multi-analyte measuring methods now will be described more fully hereinafter with reference to the accompanying drawings, in which some, but not all embodiments of the inventive concept are shown. Indeed, the detection reagents, multi-analyte diagnostic test elements, test systems and multi-analyte measuring methods may be embodied in many different forms and should not be construed as limited to the embodiments set forth herein; rather, these embodiments are provided so that this disclosure will satisfy applicable legal requirements.

Likewise, many modifications and other embodiments of the detection reagents, multi-analyte diagnostic test elements, test systems and multi-analyte measuring methods described herein will come to mind to one of skill in the art to which the disclosure pertains having the benefit of the teachings presented in the foregoing descriptions and the associated drawings. Therefore, it is to be understood that the detection reagents, multi-analyte diagnostic test elements, test systems and multi-analyte measuring methods are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the disclosure pertains. Although any methods and materials similar to or equivalent to those described herein can be used in the practice or testing of the detection reagents, multi-analyte diagnostic test elements, test systems and multi-analyte measuring methods, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one." Likewise, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. For example, the expressions "A has B," "A comprises B" and "A includes B" may refer both to a situation in which, besides B, no other element is present in A (i.e., a situation in which A solely and exclusively consists of B) or to a situation in which, besides B, one or more further elements are present in A, such as element C, elements C and D, or even further elements.

Overview

Detection reagents, multi-analyte diagnostic test elements, test systems and multi-analyte measuring methods are provided that are based upon an inventive concept that includes using particular combinations of mediators in detection reagents for multi-analyte test elements such that a single CE can be used with a plurality of analyte-specific WEs. For example, one detection reagent having a first mediator provides a WE and CE function for one analyte of interest and also provides the CE function for one or more other analytes of interest that each have their own detection reagent having a mediator different than the first mediator (i.e., the first mediator is not the same as subsequent mediators).

The detection reagents, multi-analyte diagnostic test elements, test systems and multi-analyte measuring methods are useful in a variety of applications. For example, the multi-analyte diagnostic test elements can be used to monitor a plurality of analyte concentrations in diseases or disorders such as diabetes (e.g., glucose and ketone) or heart disease (e.g., cholesterol/lipid and glucose). Likewise, the multi-analyte diagnostic test elements can be used to monitor the progress of a treatment or therapy such as an insulin therapy in diabetes.

With general regard to detection reagents, diagnostic test elements and analyte measuring methods, reference may be made to, for example, Hönes et al. (2008) *Diabetes Technol. Ther.* 10:S10-S26, Habermiller et al. (2000) *Fresenius J. Anal. Chem.* 366:560-568, and US Patent Application Publication No. 2009/0246808.

Although this disclosure is directed toward dual analyte detection reagents, diagnostic test elements, test systems and measuring methods for glucose and ketone, one of skill in the art will appreciate that other multi-analyte detection reagents, diagnostic test elements, test systems and multi-analyte measuring methods also may be beneficial such as, for example, a dual test for glucose and 1,5-anhydroglucitol or HbA1c, a dual test for glucose and cholesterol, a dual test for glucose and lactate, or even a dual test for glucose and fructosamine. It is further contemplated that more than two analytes can be measured via single multi-analyte diagnostic test elements. As such, analytes of interest include, but are not limited to, alcohols, amino acids, 1,5-anhydroglucitol, cholesterols, fructosamine, glucose, glycerines, HbA1c, HDL ketones/ketone bodies, lactates, lactate dehydrogenase, malates, pyruvates, sorbitol, triglycerides, and uric acid. As used herein, "ketone" means ketone bodies such as acetoacetate and hydroxybutyrate (HB).

Advantageously, the detection reagents, multi-analyte diagnostic test elements, test systems and multi-analyte measuring methods described herein can be used to provide a user with information on multiple analytes that provide diagnostic information specific to a disease or disorder such as diabetes. The assessments may range from detecting the presence of two or more analytes to determining the concentration of the two or more analytes. Specifically, the systems and methods herein permit persons with diabetes to more readily comply with testing recommendations and safer therapy by simultaneously measuring, for example, glucose and ketone concentrations. Moreover, the systems and methods herein permit a healthcare professional to assist in initiating and/or modifying a therapy or treatment for a disease or disorder such as diabetes.

Detection Reagents

Detection reagents can include a first analyte-specific detection reagent and a second analyte-specific detection reagent, although additional detection reagents are contemplated when more than two analytes are to be detected. As used herein, "detection reagent" or "detection reagents" mean a chemical substance or a chemical substance mixture, which in the presence of the at least one analyte changes at least one detectable property, in particular a physically and/or chemically detectable property. Typically, the property change takes place in the presence of the at least one analyte to be detected, not in the presence of other substances. However, in practice, a non-specific property change can be tolerated to a certain extent in the presence of other chemical substances, the presence of which in the sample of the body fluid is as a rule improbable and/or which only are present in very low concentrations.

In general, the components of the first and second detection reagents are dissolved or suspended in a matrix such that a body fluid sample hydrates or dissolves the matrix, and the analytes of interest in the body fluid sample diffuse through the matrix to react with one or more of the active components of the respective detection reagents.

With respect to the first analyte-specific detection reagent, it can include at least one first coenzyme-dependent enzyme, at least one first coenzyme, and at least one first mediator.

One component of the first analyte-specific detection reagent therefore is the first coenzyme-dependent enzyme. As used herein, "coenzyme-dependent enzyme" means an enzyme that requires an organic or inorganic cofactor called a coenzyme for catalytic activity.

In some instances, the first coenzyme-dependent enzyme can be a dehydrogenase. As used herein, "dehydrogenase" means a polypeptide that is capable of catalyzing an oxidation of a substrate by transferring hydrides ($H^-$) as redox equivalents to an acceptor molecule, such as a redox cofactor as referred to herein elsewhere. Examples of dehydrogenases include, but are not limited to, alcohol dehydrogenase (E.C. 1.1.1.1 or 1.1.1.2), glucose dehydrogenases, glycerin dehydrogenase (E.C. 1.1.1.6), HBDH, such as 3-HBDH (E.C. 1.1.1.30) or beta-HBDH, alpha-HBDH and gamma-HBDH, lactate dehydrogenase (E.C. 1.1.1.27 or 1.1.1.28), L-amino acid dehydrogenase (E.C. 1.4.1.5), malate dehydrogenase (E.C. 1.1.1.37), or sorbitol dehydrogenase (E.C. 1.1.1.14), especially a NAD(P)/NAD(P)H-dependent dehydrogenase.

In some instances, the dehydrogenase is a glucose dehydrogenase (GDH). Examples of GDHs include, but are not limited to, glucose dehydrogenase (E.C. 1.1.1.47), quinoprotein glucose dehydrogenase (E.C. 1.1.5.2) such as pyrroloquinoline quinone (PQQ)-dependent glucose dehydrogenase (E.C. 1.1.99.17; GDH-PQQ, also known as glucose-dye-oxidoreductase GlucDOR; see, e.g., U.S. Pat. Nos. 7,749,437 and 9,017,544), hexokinase (E.C. 2.7.1.1), glucose-6-phospate dehydrogenase (E.C. 1.1.1.49), nicotinamide adenine dinucleotide (NAD)-dependent glucose dehydrogenase (E.C. 1.1.1.119) and flavin adenine dinucleotide (FAD)-dependent glucose dehydrogenase (E.C. 1.1.99.10), or enzymatically active mutants thereof.

As used herein, "mutated" or "mutant" coenzyme-dependent enzyme means a genetically altered variant of a native coenzyme-dependent enzyme (e.g., wild-type enzyme), the variant having around the same number of amino acids as the native coenzyme-dependent enzyme but a different amino acid sequence that thus differs from the native coenzyme-dependent enzyme in at least one amino acid. Generally, the mutant coenzyme-dependent enzyme has an increased thermal and/or hydrolytic stability when compared to the native coenzyme-dependent enzyme.

Mutant coenzyme-dependent enzymes can be obtained by mutating (i.e., substituting, adding or deleting) a native coenzyme-dependent enzyme originating from any biological source. As used herein, "biological source" means both prokaryotes and eukaryotes. The introduction of the mutation(s) may be localized or non-localized; however, in some instances the localized mutations result from recombinant methods known in the art, where at least one amino acid exchange is introduced within the amino acid sequence of the native enzyme. As such, mutations can be introduced site-specifically or non-site-specifically using recombinant methods known in the art, where, according to the respective requirements and conditions, at least one amino acid exchange results within the amino acid sequence of the native enzyme. In this regard, the mutant can have an increased thermal or hydrolytic stability when compared to the wild-type enzyme.

In some instances, the mutant coenzyme-dependent enzyme is a mutant glucose dehydrogenase (E.C. 1.1.1.47) or a mutant glucose-6-phosphate dehydrogenase (E.C. 1.1.1.49). Examples of specific mutant GDHs can be found in, for example, Int'l Patent Application Publication Nos. WO 2005/045016, WO 2009/103540, WO 2010/094632 and WO 2011/020856; as well as Baik et al. (2005) *Appl. Environ. Microbiol.* 71:3285-3293 and Vásquez-Figueroa et al. (2007) *ChemBioChem* 8:2295-2301. Specifically, the GDH mutant can have a mutation at least at amino acid positions 96, 170 and/or 252. See, e.g., Int'l Patent Application Publication No. WO 2009/103540 and WO 2010/094632; and US Patent Application Publication No. 2014/0322737. Particular amino acid substitutions are Glu96Gly, Glu170Arg, Glu170Lys and/or Lys252Leu, particularly Glu170Arg and Gln252Leu in glucose dehydrogenase from *Bacillus subtilis*. Another such mutant is a PQQ-dependent GDH having improved substrate specificity when compared to its wild-type counterpart (e.g., improved glucose sensitivity with reduced or attenuated sensitivity toward a competing sugar such as maltose). See, e.g., U.S. Pat. Nos. 7,132,270; 7,547,535 and 7,732,179.

Regardless of the mutation, the mutant has essentially the same activity as the native enzyme. Mutants of the aforementioned native enzymes should be, moreover, encoded by nucleic acid molecules, which are in a position to hybridize under stringent hybridization conditions with the nucleic acid molecules that encode the native enzymes. As used herein, "stringent hybridization conditions" means a hybridization in which the nucleic acids to be hybridized are incubated at about 65° C. in Church buffer (0.5 M NaPO4 (pH 7.15), 7% SDS; 1 mM EDTA) for about 12 hours and subsequently washed twice for about 30 min in wash buffer (40 mM NaPO4 (pH 7.15), 1% SDS; 1 mM EDTA). One of the nucleic acids to be hybridized is immobilized, and the other is provided with a detectable label. If the nucleic acids hybridize with one another, this hybridization can be detected by means of the detectable label on the immobilized nucleic acid. Methods of carrying out hybridization reactions are known in the art.

Other suitable first coenzyme-dependent enzymes include, but are not limited to, oxidases such as aminotransferases such as aspartate or alanine aminotransferase, 5'-nucleotidase, cholesterol oxidase (E.C. 1.1.3.6), choline oxidase (E.C. 1.1.3.17), creatine kinase, glucose oxidase (E.C.1.1.3.4; GOx), and lactate oxidase (E.C. 1.1.3.2; LOx), as well as enzymatically active mutants thereof.

In addition to the first coenzyme-dependent enzyme, the first analyte-specific detection reagent includes the first coenzyme, which can be a native coenzyme or an artificial/stabilized coenzyme. As used herein, "coenzyme" or "redox cofactor" means a molecule that can serve as an acceptor for enzymatically transferred redox equivalents, such as hydrides ($H^-$), that are transferred from a substrate (e.g., the analyte of interest) to the enzyme to the coenzyme. As used herein, "redox equivalents" relates to a concept commonly used in redox chemistry that is well known to one of skill in the art. In particular, it relates to electrons that are transferred from a substrate of the coenzyme-dependent enzyme (i.e., the analyte of interest) to the coenzyme or electrons transferred to an electrode or indicator reagent from the coenzyme. Examples of coenzymes include, but are not limited to, FAD, NAD, NADP, PQQ, thio-NAD, thio-NADP, and a compound according to formula (I).

As noted elsewhere, the first coenzyme-dependent enzyme and the first coenzyme may be attached, bound, integrated or linked to one another. As such, they may not be physically separate components of the detection reagent but instead may be together as single component (e.g., a covalently or ionically bonded complex). Examples of such coenzyme-dependent enzyme/coenzymes include, but are not limited to, GOx (FAD coenzyme), FAD-dependent GDH (FAD-GDH), PQQ-dependent GDH, cholesterol oxidase (FAD coenzyme), and diaphorase (FMN or FAD coenzyme).

It will be understood that the first coenzyme included in the detection reagents herein depends on the properties of the coenzyme-dependent enzyme. For example, PQQ can be combined with a PQQ-dependent GDH, NAD can be combined with a NAD-dependent GDH, and FAD can be combined with a FAD-dependent GDH. NAD derivatives (e.g., NAD/NADH and/or NADP/NADPH derivatives) include carba-NAD (cNAD). See, e.g., Int'l Patent Application Publication No. WO 2007/012494.

In some instances, the first coenzyme is an artificial/stabilized coenzyme. As used herein, "artificial coenzyme" or "stabilized coenzyme" means a coenzyme that is chemically altered with respect to the native coenzyme and that at atmospheric pressure has a higher stability than the native coenzyme against humidity, temperatures in a region of about 0° C. to about 50° C., acids and bases in a range of about pH 4 to about pH 10, and/or nucleophiles such as alcohols or amines, and thus can produce its effect for a longer time when compared to the native coenzyme under identical ambient conditions. In some instances, the artificial coenzyme has a higher hydrolytic stability than the native coenzyme, complete hydrolytic stability under test conditions being particularly advantageous. Likewise, the artificial coenzyme may have a lower binding constant than the native coenzyme for the coenzyme-dependent enzyme such as, for example, a binding constant reduced by a factor of 2 or more.

As used herein, "about" means within a statistically meaningful range of a value or values such as, for example, a stated concentration, length, width, height, angle, weight, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

Examples of artificial coenzymes include, but are not limited to, artificial NAD(P)/NAD(P)H compounds, which are chemical derivatives of native NAD/NADH or native NADP/NADPH. In some instances, the artificial coenzymes include, but are not limited to, compounds according to formula (I) as shown below:

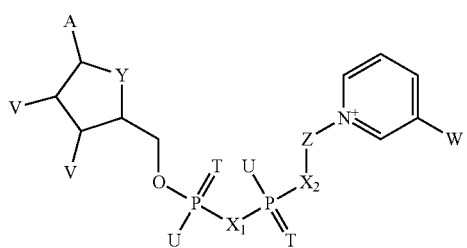

(I)

in which:
A=adenine or an analog thereof,
T=in each case independently denotes O or S,
U=in each case independently denotes OH, SH, $BH_3^-$, or $BCNH_2^-$,
V=in each case independently denotes OH or a phosphate group,
W=COOR, $CON(R)_2$, COR, or $CSN(R)_2$ in which R in each case independently denotes H or $C_1$-$C_2$-alkyl,
$X_1$, $X_2$=in each case independently denote O, $CH_2$, $CHCH_3$, $C(CH_3)_2$, NH, or $NCH_3$,
Y=NH, S, O, or $CH_2$,
Z=a residue comprising a cyclic group with 5 C atoms which optionally contains a heteroatom selected from O, S and N and optionally one or more substituents, and a residue $CR4_2$ wherein $CR4_2$ is bound to the cyclic group and to $X_2$, and
where R4=in each case independently denotes H, F, Cl, or $CH_3$, provided that Z and the pyridine residue are not linked by a glycosidic bond,
or a salt or optionally a reduced form thereof.

Exemplary substituents on Z can be OH, F, Cl, and $C_1$-$C_2$ alky, which are optionally fluorinated or chlorinated and/or OH-substituted, O—$C_1$-$C_2$-alkyl.

Alternatively, a first residue V is OH, and a second residue V is a phosphate group. Optionally, the one OH group and the one phosphate group can form a ring together with the carbon atoms to which they are bound.

Examples of adenine analogues include, but are not limited to, $C_8$-substituted and $N_6$-substituted adenine, deaza variants such as 7-deaza variants such as 8-aza or combinations such as 7-deaza or 8-aza or carbocyclic analogues such as formycin where the 7-deaza variants can be substituted in the 7 position with halogen, $C_1$-$C_6$-alkinyl, $C_1$-$C_6$-alkenyl or $C_1$-$C_6$-alkyl. Alternatively, the compounds include adenosine analogues that contain 2-methoxydeoxyribose, 2'-fluorodeoxy-ribose, hexitol, altritol or polycyclic analogues such as bicyclic, LNA and tricyclic sugars instead of ribose. In one form, (di)phosphate oxygens also can be isoelectronically substituted such as for example $O^-$ by $S^-$ and/or by $BH_3^-$, O by NH, $NCH_3$ and/or by $CH_2$ and =O by =S. Moreover, at least one residue U of a compound according to formula (I) is different from OH and alternatively at least one residue U=$BH_3$—.

Alternatively, the artificial coenzymes include, but are not limited to, compounds according to formula (I) as shown below:

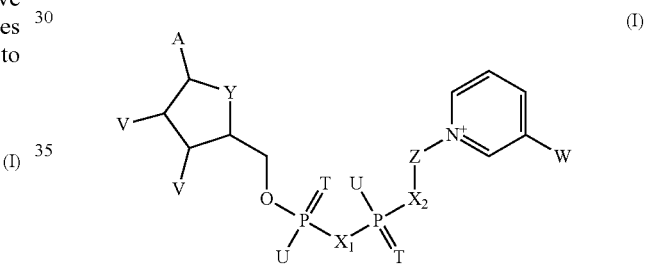

(I)

in which:
A=adenine,
T=in each case denotes O,
U=in each case denotes OH,
V=in each case denotes OH,
W=$CON(R)_2$ in which R denotes H,
$X_1$=O,
$X_2$=O,
Y=O, and
Z=a carbocyclic 5-membered ring of the general formula (II)

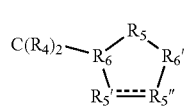

(II)

in which a single bond is present between $R_5'$ and $R_5''$, and in which
$R_4$=H,
$R_5'$=CHOH,
$R_5''$=CHOH,
$R_5$=$CR4_2$,
$R_6$=CH, and
$R_6'$=CH.

Alternatively still, the artificial coenzymes include, but are not limited to, compounds according to formula (I) as shown below:

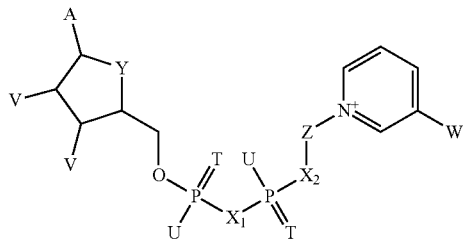

in which:
A=adenine,
T=in each case denotes O,
U=in each case denotes OH,
V=in a first case denotes OH and in a second case denotes a phosphate group,
W=CON(R)$_2$ in which R denotes H,
X$_1$=O,
X$_2$=O,
Y=O, and
Z=a carbocyclic 5-membered ring of the general formula (II):

in which a single bond is present between R$_5$' and R$_5$", and in which
R$_4$=H,
R$_5$'=CHOH,
R$_5$"=CHOH,
R$_5$=CR4$_2$,
R$_6$=CH, and
R$_6$'=CH.

In certain instances, the artificial coenzyme can be carba-NAD or carba-NADP. See, Slama & Simmons (1988) *Biochem.* 27:183-193; and Slama & Simmons (1989) *Biochem.* 28:7688-7694. Carba-NAD has the following structure:

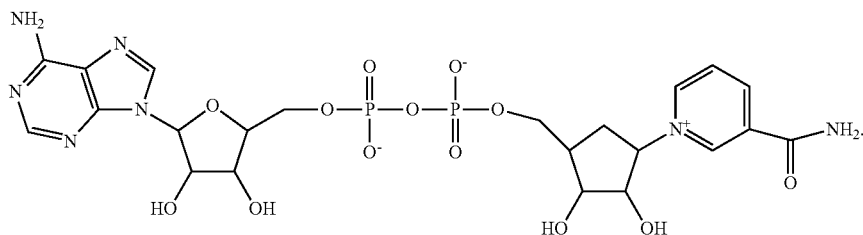 [SMILES: NC(=O)c1ccc[n+](C2CC(COP(=O)([O-])OP(=O)([O-])OCC3OC(n4cnc5c(N)ncnc54)C(O)C3O)C(O)C2O)c1]

Carba-NADP has the following structure: v

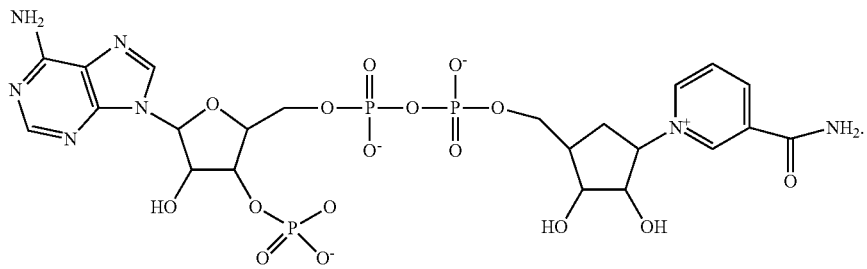 [SMILES: NC(=O)c1ccc[n+](C2CC(COP(=O)([O-])OP(=O)([O-])OCC3OC(n4cnc5c(N)ncnc54)C(O)C3OP(=O)([O-])O)C(O)C2O)c1]

Other compounds according to formula (I) include borano carba-NAD, cyclopentyl-NAD, and carba-NAD cyclophosphate. These compounds have the following structures:

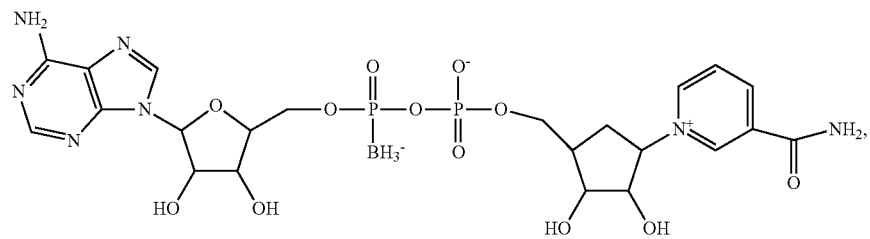

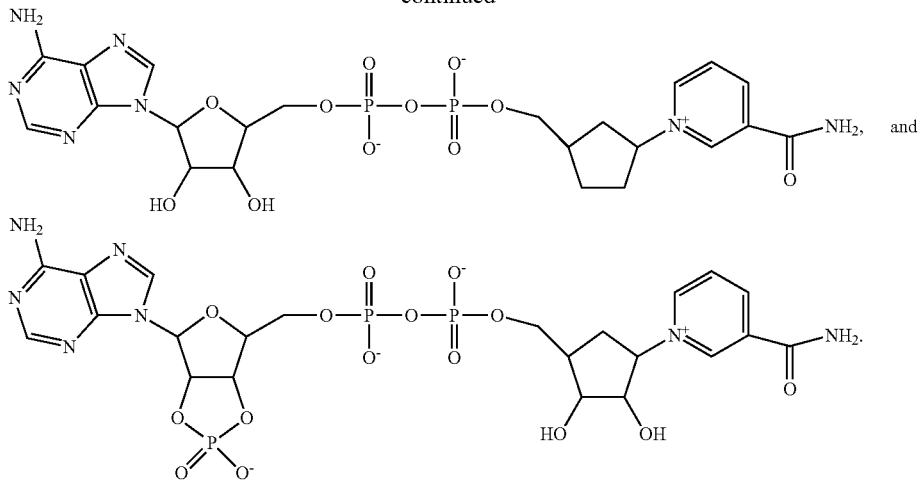

Further details regarding compounds according to formula (I) and synthesis thereof is disclosed in Int'l Patent Application Publication No. WO 2007/012494; as well as U.S. Pat. No. 7,553,615.

Other artificial coenzymes that can be used in the detection reagents described herein are disclosed in Int'l Patent Application Publication Nos. WO 1998/033936, WO 2001/049247, WO 2009/103540 and WO 2011/020856; U.S. Pat. No. 5,801,006; and Hutchinson et al. (1996) *Chem. Commun.* 24:2765-2766.

In addition to the first coenzyme-dependent enzyme and the first coenzyme, the first analyte-specific detection reagent includes the first mediator. As used herein, "mediator" means a chemical compound that increases reactivity of a reduced coenzyme obtained by reaction with the analyte and that transfers electrons to an electrode system or to a suitable optical indicator/optical indicator system.

The mediator can be any chemical species (generally electroactive) that can participate in a reaction scheme involving an analyte, a coenzyme-dependent enzyme, a coenzyme, and reaction products thereof, to produce a detectable electroactive reaction product. Typically, participation of the mediator in the reaction involves a change in its oxidation state (e.g., a reduction) upon interaction with any one of the analyte, the coenzyme-dependent enzyme, the coenzyme, or a species that is a reaction product of one of these (e.g., a coenzyme reacted to a different oxidation state). A variety of mediators exhibit suitable electrochemical behavior. A mediator also can be stable in its oxidized form, may optionally exhibit reversible redox electrochemistry, can exhibit good solubility in aqueous solutions, and can react rapidly to produce an electroactive reaction product. A review of mediators that directly transfer redox equivalents to a suitable detection system and that can be used for electrochemically determining blood glucose may be found in, for example, Takaminami (2008) *Mater. Integr.* 21:317-323 and Heller et al. (2008) *Chem. Rev.* 108:2482-2505.

Examples of first mediators include, but are not limited to, an azo compound or an azo precursor, benzoquinone, meldola blue, a nitrosoaniline or a nitrosoaniline-based precursor, a thiazine or a thiazine derivative, a transition metal complex such as potassium ferricyanide, ruthenium complexes such as ruthenium hexamine chloride, osmium derivatives, a quinone or a quinone derivative, a phenazine or a phenazine-based precursor, and a combination of a phenazine derivative and hexaammineruthenium chloride, as well as derivatives thereof. See, e.g., Int'l Patent Application Publication No. WO 1998/035225; and U.S. Pat. Nos. 5,286,362 and 8,008,037; as well as Gorton & Dominguez (2002) *Rev. Mol. Biotechnol.* 82:371-392.

Examples of azo compounds and azo precursors include, but are not limited to, the compounds described in US Patent Application Publication No. 2014/0212903, especially those azo compounds that do not form azoxy dimers.

Examples of nitrosoaniline-based compounds that can act as a mediator precursor include, but are not limited to, the compounds described in EP Patent Nos. 0620283 and 0831327; U.S. Pat. Nos. 5,206,147 and 5,286,362; and Int'l Patent Application Publication No. WO 2013/131885. In this manner, the nitrosoaniline-based mediator precursor breaks down into reversible mediator components when it contacts a body fluid sample.

Other examples of nitrosoaniline-based mediator precursors include, but are not limited to, N-(2-hydroxyethyl)-N'-p-nitrosophenyl-piperazine, N,N-bis-(2-hydroxyethyl)-p-nitrosoaniline, o-methoxy-[N,N-bis-(2-hydroxyethyl)]-p-nitrosoaniline, p-hydroxynitrosobenzene, N-methyl-N'-(4-nitrosophenyl)-piperazine, p-quinone dioxime, N,N-dimethyl-p-nitrosoaniline, N,N-diethyl-p-nitrosoaniline, N-(4-nitrosophenyl)-morpholine, N-benzyl-N-(5'-carboxypentyl)-p-nitrosoaniline, N,N-dimethyl-4-nitroso-1-naphthylamine, N,N,3-trimethyl-4-nitrosoaniline, N-(2-hydroxyethyl)-5-nitrosoindoline, N,N-bis-(2-hydroxyethyl)-3-chloro-4-nitrosoaniline, 2,4-dimethoxy-nitrosobenzene, N,N-bis-(2-m ethoxyethyl)-4-nitrosoaniline, 3-methoxy-4-nitrosophenol, N-(2-hydroxyethyl)-6-nitroso-1,2,3,4-tetrahydroquinoline, N,N-dimethyl-3-chloro-4-nitrosoaniline, N,N-bis-(2-hydroxyethyl)-3-fluoro-4-nitrosoaniline, N, N-bis(hydroxyethyl)-3-m ethoxy-4-nitrosoaniline hydrochloride (NA114), N, N-bis-(2-hydroxyethyl)-3-methylthio-4-nitrosoaniline, N-(2-hydroxyethyl)-N-(2-(2-methoxyethoxy)-ethyl)-4-nitrosoaniline, N-(2-hydroxyethyl)-N-(3-methoxy-2-hydroxy-1-propyl)-4-nitrosoaniline, N-(2-hydroxyethyl)-N-(3-(2-hydroxyethoxy)-2-hydroxy-1-propyl)-4-nitrosoaniline, N-(2-hydroxyethyl)-N-(2-(2-hydroxyethoxy)-ethyl)-4-nitrosoaniline, and [(4-nitrosophenyl)imino]dimethanol-hydrochloride.

Examples of osmium derivatives include, but are not limited to, the compounds disclosed in EP Patent No. 1457572 and Int'l Patent Application Publication No. 1998/035225.

Examples of phenazines or phenazine-based precursors include, but are not limited to, as phenazinethosulfate (PES), phenazinmethosulfate (PMS), 1-(3-carboxypropoxy)-5-ethylphenaziniumtrifluoromethansulfonate, 1-(3-caroboxypropoxy)-5-ethyl-phenazin-5-ium) (cPES), 1-(3-carboxypropionylamino)-5-ethyl-phenazin-5-ium (PG355), or 1-methoxyphenazinmethosulfate. See, e.g., EP Patent Application Publication No. 0654079; and Gorton (1986) *Chem. Soc., Faraday Trans.* 1 82:1245-1258. In some instances, the phenazine can be 1-amino-phenazine derivative. See, e.g., Int'l Patent Application Publication No. WO 2015/158645. In certain instances, the phenazine can be one of the following structures or derivatives thereof:

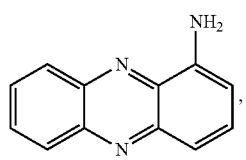

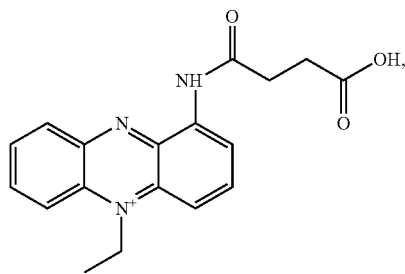

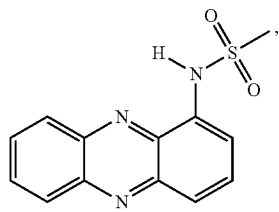

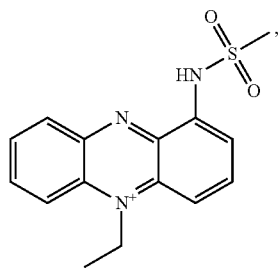

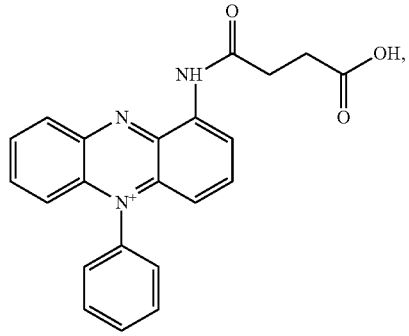

-continued

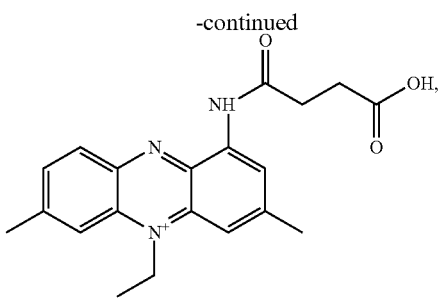

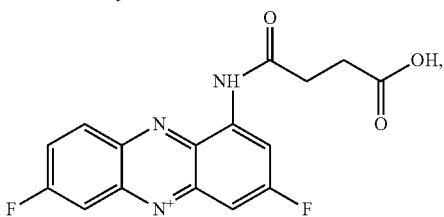

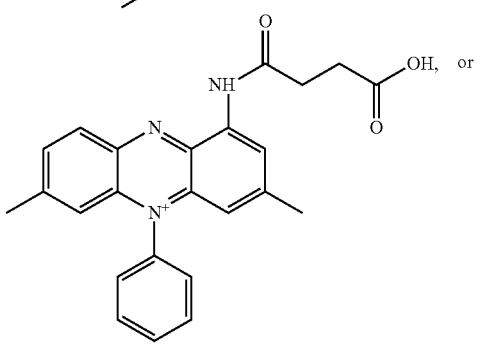

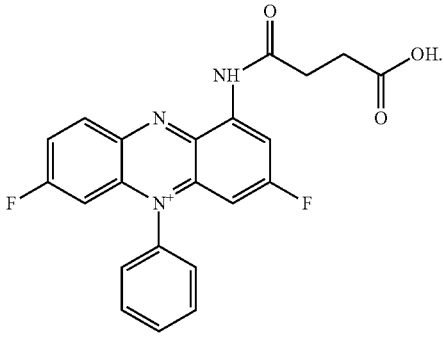

Examples of quinones or quinone derivatives include, but are not limited to, ortho and para quinones, as well as quinonediimines. See, e.g., Gorton (1986), supra; Degrand & Miller (1980) *J. Am. Chem. Soc.* 102:5728-5732; Kitani & Miller (1981) *J. Am. Chem. Soc.* 103:3595-3597; and Baldwin (1983) *Anal. Chem.* 55:1588-1591.

In some instances, the first mediator is N,N-bis(hydroxyethyl)-3-methoxy-4-nitrosoaniline hydrochloride (NA1144).

With respect to the concentration of first mediator, it generally is a very stable mediator (i.e., at least more stable than the second mediator) and is provided in a higher concentration than the second mediator (i.e., the second mediator is provided at a lower concentration than the first mediator). One of skill in the art, however, understands that the relative mediator concentrations are determined, in part, by the analyte concentration ranges expected to be detected. For example, and when monitoring glucose and ketones, the 3-HB concentration range is significantly smaller than the glucose concentration range. Thus, the ketone mediator can be at a lower concentration than the glucose mediator. More specifically, the main consideration for the glucose mediator concentration (i.e., the first mediator) is that it be high enough to support a signal at the high glucose range and thus provide enough oxidized mediator (e.g., nitroso form and quinonediimine form) to support a counter electrode reaction. Depending on the reagent formulation, and based upon a glucose only test element, the first mediator concentration can be from about 10 mM to about 40 mM, from about 15 mM to about 35 mM, from about 20 mM to about 30 mM, or about 25 mM. Alternatively, the first mediator concentration can be about 10 mm, about 15 mM, about 20 mM, about 25 mM, about 30 mM, about 35 mM, or about 40 mM. Alternatively still, the first mediator concentration can be about 10 mM, about 12 mM, about 14 mM, about 16 mM, about 18 mM, about 20 mM, about 22 mM, about 24 mM, about 26 mM, about 28 mM, about 30 mM, about 32 mM, about 34 mM, about 36 mM, about 38 mM, or about 40 mM.

When the coenzyme is NAD/NADH, the mediator can be a quinone (such as an ortho or para quinone), a quinonediimine, a phenazine, a phenoxazine, or a phenothiazine.

Likewise, and when the coenzyme is cNAD/cNADH, the mediator can be PG355, cPES, PES, PMS or N,N-bis (hydroxyethyl)-3-methoxy-4-nitrosoaniline hydrochloride.

Additional non-limiting examples of reagent materials operable for detecting the presence and/or concentration of glucose are disclosed in US Patent Application Publication Nos. 2003/0146113 and 2014/0212903; and U.S. Pat. Nos. 7,727,467 and 8,008,037, as well as Huang et al. (2014) *Clin. Chim. Acta.* 433:28-33.

With respect to the second analyte-specific detection reagent, it can include at least one second coenzyme-dependent enzyme, at least one second coenzyme, and at least one second mediator, where the at least one second mediator is distinct from the at least one first mediator included in the first analyte-specific detection reagent. As above, the components of the second analyte-specific detection reagent are dissolved or suspended in a matrix such that a body fluid sample hydrates or dissolves the matrix, and the analytes diffuse through the matrix to react with one or more of the active components of the detection reagents.

The second coenzyme-dependent enzyme can be an enzyme as listed above and can even be the same enzyme as the first coenzyme-dependent enzyme when one wishes to perform a duplicate analyte measurement on the same diagnostic test element. Alternatively, the first and the second coenzyme-dependent enzymes are not the same.

As noted elsewhere, the second coenzyme-dependent enzyme and the second coenzyme may be attached, bound, integrated or linked to one another. As such, they may not be physically separate components of the detection reagent but instead may be together as single component (e.g., a covalently or ionically bonded complex).

In some instances the second coenzyme-dependent enzyme is a HBDH. Examples of HBDHs include, but are not limited to, alpha-HBDH, beta or 3-HBDH, and gamma-HBDH.

In addition to the second coenzyme-dependent enzyme, the second analyte-specific detection reagent can include the second coenzyme, which can be a native coenzyme or an artificial/stabilized coenzyme. The second coenzyme can be a coenzyme as listed above and can even be the same coenzyme as the first coenzyme. Alternatively, the first and the second coenzymes are not the same.

As above for the first analyte-specific detection reagent, examples of second coenzymes include, but are not limited to, FAD, NAD, NADP, PQQ, thio-NAD, thio-NADP, and a compound according to formula (I). In some instances, such as when the second analyte is a ketone, the second coenzyme can be thio-NAD, thio-NADP or a compound according to formula (I) or a salt or optionally a reduced form thereof, especially carba-NAD or carba-NADP.

In addition to the second coenzyme-dependent enzyme and the second coenzyme, the second analyte-specific detection reagent includes the second mediator. As above for the first analyte-specific detection reagent, examples of second mediators include, but are not limited to, an azo compound or an azo precursor, benzoquinone, meldola blue, a nitrosoaniline or a nitrosoaniline-based precursor, a thiazine or a thiazine derivative, a transition metal complex such as potassium ferricyanide, ruthenium hexamine chloride, and osmium derivatives, a quinone or a quinone derivative, a phenazine or a phenazine-based precursor, and a combination of a phenazine derivative and hexaammineruthenium chloride, as well as derivatives thereof, with the proviso that the second mediator is not the same as the first mediator. In some instances, such as when the second analyte is a ketone, the second mediator can be a phenazine or a phenazine-based derivative, especially 1-amino-phenazine derivatives like PG355. See, e.g., Int'l Patent Application Publication No. 2015/057933.

With respect to the concentration of the second mediator, it generally is a less stable mediator (i.e., at least less stable than the first mediator) and is provided at a lower concentration than the first mediator (i.e., the first mediator is provided at a higher concentration than the second mediator). As noted above, one of skill in the art understands that the relative mediator concentrations are determined, in part, by the analyte concentration ranges expected to be detected. For example, and when monitoring glucose and ketone, the 3-HB concentration range is significantly smaller than the glucose concentration range. Thus, the ketone mediator can be at a lower concentration than the glucose mediator. More specifically, with respect to "low" and "high" concentrations of the second mediator concentration can be from about 2.5 mM to about 8.5 mM, from about 3.0 mM to about 7.5 mM, from about 3.5 mM to about 7.0 mM, from about 4.0 mM to about 6.5 mM, from about 4.5 mM to about 6.0 mM, or from about 5.0 mM to about 5.5 mM. Alternatively, the second mediator concentration can be about 2.5 mM, about 3.0 mM, about 3.5 mM, about 4.0 mM, about 4.5 mM, about 5.0 mM, about 5.5 mM, about 6.0 mM, about 6.5 mM, about 7.0 mM, about 7.5 mM, about 8.0 mM, or about 8.5 mM.

Stated differently, ratios of second to first mediators could be in the range of about 1:1.5, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, or about 1:10. An exemplary ratio can be 1:1.6 (e.g., 7.5 mM PG355: 16 mM NA1144) to about 1:8 (5 mM PG355: 40 mM NA1144).

Additional non-limiting examples of reagent materials operable for detecting the presence and/or concentration of ketones are disclosed in U.S. Pat. Nos. 8,920,628 and 8,921,061.

Aside from the coenzyme-dependent enzymes, coenzymes, and mediators, the detection reagents can include other substances used for qualitative analysis and/or quantitative determination of the analytes of interest. For example, the detection reagents can include a variety of adjuvants to enhance various properties or characteristics thereof. See, e.g., U.S. Pat. No. 7,749,437. Moreover, the detection reagents may include materials for facilitating their placement onto respective substrates and improving their adherence thereto or for increasing the rate of hydration of the reagent materials by the sample fluid. Furthermore, the detection reagents can include components for enhancing the physical properties of the resulting dried reagent layer and improving the uptake of a body fluid sample for analysis. See, e.g., Int'l Patent Application Publication No. WO 2013/131885.

Examples of adjuvant materials include, but are not limited to, buffers, carrier substances, coloring agents, compatible solutes, deliquescent materials, detergents, fillers, film formers, film openers, gelling agents, pigments, solid particles, stabilizers, swelling agents, thickeners, thixotropic agents, and viscosity modulators.

Examples of buffers include, but are not limited to, phosphate buffered saline, Tris buffer, citrate buffer, glycerine phosphate buffer, and Good's buffer. Additional details regarding buffers in detection reagents can be found in, for example, Int'l Patent Application Publication No. 2012/010308.

Examples of deliquescent materials include, but are not limited to, one or more of sodium chloride, calcium chloride, magnesium chloride, zinc chloride, potassium carbonate, potassium phosphate, carnallite, ferric ammonium citrate, potassium hydroxide, and sodium hydroxide. Additional details regarding deliquescent materials in detection reagents can be found in, for example, Int'l Patent Application Publication No. WO 2014/037372.

Examples of detergents that can be included in the detection reagents include, but are not limited to, water-soluble soaps, as well as water-soluble synthetic surface-active compounds such as alkali, earth alkali or optionally substituted ammonium salts of higher fatty acids (e.g., oleic or stearic acid), mixtures of natural fatty acids (e.g., coconut or tallow oil), fatty sulphates, esters of sulphonic acids, salts of alkyl sulphonic acids taurine salts of fatty acids, fatty acid amides, and ester amides. Additional detergents include an ester amide sodium-N-methyl-N-oleoyltaurat, N-octanoyl-N-methyl-glucamide, Mega 8 (N-methyl-N-octanoylglucamide), dioctylsodium sulfosuccinate (DONS), RHODAPEX® (especially CO-433 or CO-436), TEGO® Wet 265 (Evonik Resource Efficiency GmbH; Essen, Germany), TERGITOL® 15-s-19 (Dow Chemical Corp.; Midland, Mich. USA), and a fatty acid salt, N-methyl oleyl taurate sodium salt, sold under the trade name GEROPON® T77 (Rhodia HPCII (Home, Personal Care & Industrial Ingredients).

Examples of film formers and thixotropic agents include, but are not limited to, polymers and silicas such as polyvinylpropionate dispersions, polyvinyl esters, polyvinyl acetates, polyacrylic esters, polymethacrylic acid, polyvinyl amides, polyamides, polystyrene and mixed polymerizates such as butadiene, styrene or maleic acid ester. One more specific thixotropic agent includes silicas sold under the trade name KIESELSAURE SIPEMATE FK 320 DS (Degussa AG), while a more specific film forming agent includes polyvinylpyrrolidone (PVP), sold under the trademark polyvinylpyrrolidone KOLLIDON 25 (BASF) and polyvinyl propionate dispersion.

Examples of solid particles include, but are not limited to, silica particles such as silicon dioxide, sodium silicates or aluminium silicates, diatomaceous earth, metal oxides such as titan oxide and/or aluminium oxide, synthetic oxide materials such as nanoparticles of oxide materials such as nanoparticles of silicon dioxide, aluminium oxide, or titan oxide, Kaolin, powder glass, amorphous silica, calcium sulfate and barium sulfate.

Examples of stabilizers for the coenzyme-dependent enzymes include, but are not limited to, saccharides and mono- or di-fatty acid salts. Another stabilizer includes trehalose sold under the trade name D-(+)-trehalose dihydrate (Sigma Chemical Co). and sodium succinate.

Examples of swelling agents include, but are not limited to, methyl vinyl ether maleic acid anhydride copolymer, xanthan gum and methyl vinyl ether maleic acid copolymer. Examples of thickeners include, but are not limited to, starches, gums (e.g., pectin, guar gum, locust bean (carob seed) gum, konjac gum, xanthan gum, alginates, and agar), casein, gelatin and phycocolloids; cellulose and semi-synthetic cellulose derivatives (carboxymethyl-cellulose, methyl cellulose, hydroxymethylcellulose, hydroxyethylcellulose, methylhydroxyethylcellulose); polyvinyl alcohol and carboxy-vinylates; and bentonite, silicates and colloidal silica. More specific forms of thickeners include a combination of a xanthan gum sold under the trade name KELTROL® F (CP Kelco US, Inc.) and carboxylmethyl cellulose sold under the trade name AQUALON® CMC 7F PH (Hercules Inc., Aqualon Division).

Additional details regarding detection reagents and components thereof that may be used herein can be found in, for example, HOnes et al. (2008), supra, Int'l Patent Application Publication Nos. WO 2007/012494, WO 2009/103540, WO 2010/094426, WO 2010/094427, WO 2011/012269, WO 2011/012270 and WO 2011/012271. Additional reference may be made to EP Patent Application Publication Nos. 0354441, 0431456, 0302287, 0547710 and 1593434 for test substances that may be used herein.

Although the detection reagents have been generally described as being for use in electrochemical test elements, the detection reagents herein also can be for use in optical test elements. In this instance, the detection reagents also can include an indicator. As used herein, "indicator" means any desired substance that is influenced by the course of the detection reaction of the analyte detection, in particular of the enzymatic reaction, such that at least one property change of the indicator can be recorded in the course of the detection reaction. In some instances, this property can be an optical property. Thus, the indicator can be at least one dye. Additional details regarding optical test elements can be found in, for example, US Patent Application Publication No. 2014/0363835.

As the optical indicator or as the optical indicator system, in particular, any desired substance can be used that is reducible and during reduction undergoes a detectable change of its optical properties such as, for example, color, fluorescence, reflectance, transmission, polarization or/and refractive index. The determination of the presence or/and of the amount of the analyte in the sample can take place using the naked eye or/and by means of a detection device using a photometric method appearing suitable to one of skill in the art. In some instances, heteropolyacids such as 2,18-phosphormolybdic acid are used as optical indicators, which are reduced to the corresponding heteropolyblue.

Additionally, the use of fluorophores for detecting glucose concentrations in diagnostic test elements generally is known in, for example, EP Patent No. 1780288 and Int'l Patent Application Publication No. WO 2009/015870. Glucose-induced changes in the fluorescence of proteins and other fluorophores also are known. See, Pickup et al. (2005) *Biosens. Bioelectron.* 20:2555-2565; and US Patent Application Publication No. 2012/0053429.

It is to be appreciated that the chemistry of the reaction scheme of the detection reagents herein can be chosen in light of various chemical factors relating to the system, including the identity of the analyte and of the sample substance. Even then, for a given analyte or substance, various different reactive components may be useful in terms of a catalyst (often, a variety of enzymes will be useful), co-reactants (e.g., a variety of mediators may be useful), and cofactors (if needed, a variety may be useful). Many such detection reagents and their reactive components and reaction products are known, and examples of a few different enzymes include those listed in Table 1.

TABLE 1

Exemplary Detection Reagents for Diagnostic Test Elements.

| Analyte | Enzymes | Mediators (oxidized form) | Additional Mediators |
|---|---|---|---|
| Glucose | glucose dehydrogenase and diaphorase | ferricyanide, osmium (III)-(bipyridyl)-2-imidazolyl-chloride, meldola blue, [Ru(NH$_3$)$_5$MeIm] Cl$_3$ [OS(III) (NH$_3$)$_5$pyz]$_2$(SO$_4$)$_3$, nitrosoaniline derivatives | N/A |
| Glucose | glucose oxidase | (see above) | N/A |
| Cholesterol | cholesterol esterase and cholesterol oxidase | (see glucose) | 2,6-dimethyl-1,4-benzoquinone, 2,5-dichloro-1,4-benzoquinone, or phenazine ethosulfate |
| HDL Cholesterol | cholesterol esterase and cholesterol oxidase | (see glucose) | (see above) |
| Ketone | hydroxybutyrate dehydrogenase | phenazine methosulfate, phenazine ethosulfate | |
| Triglycerides | lipoprotein lipase, glycerol kinase, glycerol-3-phosphate oxidase | (see glucose) | phenazine methosulfate, phenazine ethosulfate |
| Triglycerides | lipoprotein lipase, glycerol kinase, glycerol-3-phosphate dehydrogenase and diaphorase | (see glucose) | (see above) |
| Lactate | lactate oxidase | (see glucose) | 2,5-dichloro-1,4-benzoquinone |
| Lactate | lactate dehydrogenase and diaphorase | (see glucose) | N/A |
| Lactate Dehydrogenase | diaphorase | (see glucose) | N/A |
| Pyruvate | pyruvate oxidase | (see glucose) | N/A |
| Alcohol | alcohol oxidase | (see glucose) | N/A |
| Alcohol | alcohol dehydrogenase and diaphorase | (see glucose) | N/A |
| Uric acid | uricase | (see glucose) | N/A |
| 3-HB (ketone bodies) | 3-HBDH and diaphorase | (see glucose) | N/A |

In view of the above, exemplary dual detection reagents for multi-analyte analysis can include, but are not limited to, those listed in Table 2.

TABLE 2

Exemplary Dual Analyte Detection Reagents for Diagnostic Test Elements.

Glucose & Ketone

| | |
|---|---|
| 1$^{st}$ enzyme | GDH, glucose-6-phospate dehydrogenase or GOx |
| 1$^{st}$ coenzyme | FAD, NAD or NADP |
| 1$^{st}$ mediator | a nitrosoaniline derivative or nitrosoaniline-based precursor, ferricyanide, ruthenium hexamine, or phenazine |
| 2$^{nd}$ enzyme | HBDH |
| 2$^{nd}$ coenzyme | carba-NAD, carba-NADP, thio-NAD or thio-NADP |
| 2$^{nd}$ mediator | medola blue, a phenazine or phenazine-based precursor, or a quinone or a quinone derivative |
| 1$^{st}$ enzyme | FAD-GDH |
| 1$^{st}$ coenzyme | FAD |
| 1$^{st}$ mediator | NA1144 |
| 2$^{nd}$ enzyme | HBDH/diaphorase |
| 2$^{nd}$ coenzyme | carba-NAD/FAD or FMN |

TABLE 2-continued

Exemplary Dual Analyte Detection Reagents for Diagnostic Test Elements.

| | |
|---|---|
| 2$^{nd}$ mediator | NA1144 |
| 1$^{st}$ enzyme | GDH |
| 1$^{st}$ coenzyme | carba-NAD |
| 1$^{st}$ mediator | a phenazine, phenazine-based precursor, modified phenazines, meldola blue, quinone or quinone derivative |
| 2$^{nd}$ enzyme | HBDH |
| 2$^{nd}$ coenzyme | carba-NAD |
| 2$^{nd}$ mediator | a phenazine, phenazine-based precursor, modified phenazines, meldola blue, quinone or quinone derivative |

Dual Glucose

| | |
|---|---|
| 1$^{st}$ enzyme | FAD-GDH, NAD-GDH, PQQ-GDH or GOx |
| 1$^{st}$ coenzyme | FAD for FAD-GDH and GOx, NAD, NADP, cNAD, cNADP, thio-NAD, thio-NADP for NAD-GDH, or PQQ for PQQ-GDH |
| 1$^{st}$ mediator | a nitrosoaniline derivative or nitrosoaniline-based precursor, ferricyanide, ruthenium hexamine, medola |

TABLE 2-continued

Exemplary Dual Analyte Detection Reagents for Diagnostic Test Elements.

|  |  |
|---|---|
|  | blue, a phenazine or phenazine-based precursor, or a quinone or a quinone derivative |
| $2^{nd}$ enzyme | FAD-GDH, NAD-GDH, PQQ-GDH or GOx |
| $2^{nd}$ coenzyme | FAD for FAD-GDH and GOx, NAD, NADP, cNAD, cNADP, thio-NAD, thio-NADP for NAD-GDH, or PQQ for PQQ-GDH |
| $2^{nd}$ mediator | a nitrosoaniline derivative or nitrosoaniline-based precursor, ferricyanide, ruthenium hexamine, medola blue, a phenazine or phenazine-based precursor, or a quinone or a quinone derivative |
| $1^{st}$ enzyme | PQQ-GDH or GDH |
| $1^{st}$ coenzyme | PQQ |
| $1^{st}$ mediator | a nitrosoaniline derivative or nitrosoaniline-based precursor, ferricyanide, ruthenium hexamine, or phenazine, medola blue, a phenazine or phenazine-based precursor, or a quinone or a quinone derivative |
| $2^{nd}$ enzyme | a mutant variant of quinoprotein GDH (e.g., a mutant PQQ-GDH with low maltose sensitivity; see, e.g., Igarashi et al. (1999) *Biochem. Biophys. Res. Commun.* 264: 820-824 and Igarashi et al. (2004) *Biomol. Eng.* 21: 81-89) |
| $2^{nd}$ coenzyme | PQQ |
| $2^{nd}$ mediator | a nitrosoaniline derivative or nitrosoaniline-based precursor, ferricyanide, ruthenium hexamine, or phenazine, medola blue, a phenazine or phenazine-based precursor, or a quinone or a quinone derivative |

Additional detection reagents that may be combined with one of the above-described detection reagents include, but are not limited to, (1) a lactate detection reagent, where LDH is the coenzyme-dependent enzyme, carba-NAD is the coenzyme and PG355 is the mediator; (2) a lactate detection reagent, where lactate oxidase (LOx) is the coenzyme-dependent enzyme, flavin mononucleotide is the coenzyme, and NA1144 is the mediator; (3) a fructosamine detection reagent, where fructosamine oxidase (FOx) is the coenzyme-dependent enzyme, FAD is the coenzyme, and NA1144 is the mediator; (4) a cholesterol detection reagent, where cholesterol oxidase (CHOx) is the coenzyme-dependent enzyme, FAD is the coenzyme, and NA1144 is the mediator; and (5) a choline detection reagent, where choline oxidase (COx) is the coenzyme-dependent enzyme, FAD is the coenzyme, and NA1144 is the mediator.

Multi-Analyte Diagnostic Test Elements

Multi-analyte diagnostic test elements can include an electrode system having at least two WEs and at least one CE in connection with other electrode system components that are disposed upon a substrate. The detection reagents described above are incorporated into a dry-film detection reagent matrix that is provided on an inert support substrate or base for the test elements and are in physical and/or electrical contact with the electrode system for electrochemically analyzing a body fluid sample for a presence or a concentration of one or more analytes of interest.

Diagnostic test elements generally are known and are available in different forms, to which the present disclosure as a whole is applicable. For example, test elements in the form of test strips, test tapes, test disks, foldable test elements (e.g., according to the Leporello principle) and other forms as are known to one of skill in the art. Hereinafter, while the inventive concept will be described substantially with reference to test elements such as test strips, it is to be appreciated that other embodiments also are possible and are intended to be within the scope of the disclosure.

Diagnostic test elements typically are provided in the form of a disposable test strip having a laminar construction including a non-conductive base substrate, a spacer, and a cover. Further details of test elements including a similar laminar construction are provided in U.S. Pat. Nos. 7,727,467 and 8,992,750. In this manner, the test elements can be any one of a plurality produced from rolls of material, sheets of material or any other material stock in accordance with the principles of this disclosure. In general, the material selection for fabricating the test elements includes any material that is sufficiently flexible for roll processing, but is rigid enough to give a useful stiffness to the finished test elements. Moreover, test elements may include one or more graphics to provide a user with guidance on proper handling and use.

In view thereof, one part of the diagnostic test elements herein is a base or support substrate upon which the several components can be constructed, deposited and/or disposed. The substrate includes a first surface facing a spacer and a second surface that is opposite the first surface. Moreover, the substrate has opposite first and second ends (e.g., a dosing end and a meter insertion end, respectively) and opposite side edges that extend between the first and second ends. In some instances, the first and second ends and the opposite side edges of the substrate thus form a generally rectangular shape; however, any one of a number of forms that enable the test elements to function as described herein also are contemplated.

Typically, the substrate is fabricated from a flexible polymer including, but not limited to, a polyester or polyimide, such as polyethylene naphthalate (PEN) or polyethylene terephthalate (PET). Alternatively, the substrate can be fabricated from any other suitable materials that enable the substrate to function as described herein.

In addition to the substrate, the diagnostic test elements herein can include a spacer that is disposed on the first surface of the substrate, where the spacer includes at least one edge defining a boundary of a capillary channel formed between a cover and the substrate. Like the substrate, the spacer can be fabricated from an insulative material such as, for example, a flexible polymer including an adhesive coated PET. In some instances, the spacer can be a PET film, both sides of which are coated with a pressure-sensitive adhesive. Thus, the spacer includes one surface coupled to the first surface of the substrate using any one or a combination of a wide variety of commercially available adhesives. Alternatively, the substrate may be coupled to the spacer by welding, such as heat or ultrasonic welding. In some instances, however, the spacer can be omitted if the cover and/or the substrate is dimensioned to function as the spacer.

In addition to the substrate and the spacer, the diagnostic test elements herein can include a cover that is positioned over the spacer. The cover is generally sized and shaped to match the substrate and thus extends between the opposite side edges of the substrate and extends to the first and second ends of the substrate. Alternatively, one of the cover or the substrate may extend beyond the other to a predefined distance that enables the test elements to function as described herein (i.e., the test elements include an overhang/cantilever at the sampling end). Consequently, the sample chamber, which functions as a capillary, is therefore defined as a space between the cover and the substrate that is bounded by one or more edges of the spacer.

Like the substrate and the spacer, the cover can be fabricated from an insulative material such as, for example, a flexible polymer including an adhesive-coated PET. One particular non-limiting example of a suitable material includes a transparent or translucent PET film. The cover thus includes a lower surface that may be coupled to the spacer using any one or a combination of a wide variety of commercially available adhesives. Alternatively, the cover may be coupled to the spacer by welding, such as heat or ultrasonic welding.

Together, the substrate, spacer and cover form the sample chamber, in which a part of the electrode system and the detection reagents are accessible to the body fluid sample for a measurement. In some instances, the test elements are full width end dose ("FWED"; having a capillary channel bounded on one side) test elements, which allow a sample to fill the sample chamber from the first end (i.e., front) of the test element or from its sides. In FWED test elements, the spacer extends between the opposite side edges of the substrate to form the sample chamber in part with a cover. It is contemplated that the spacer may be fabricated of a single component or even a plurality of components. Regardless, the spacer should include an end edge substantially parallel to and facing the first end of the substrate, thereby defining a boundary of the sample chamber by extending across the entire width of the substrate.

It is further contemplated that the sample chamber also can be a conventional capillary channel (i.e., bounded on more than one side). In this manner, the end edge of the spacer may include multiple portions located between the first and second ends and the opposite side edges of the substrate to form a generally U-shaped pattern to define the boundary of the sample chamber having a sample inlet at the first end of the test elements. Other suitable embodiments contemplate an end edge of the spacer that forms hemi-ovular, semi-circular, or other shaped capillary channels, and the one or more of the portions of end edge may include linear or non-linear edges along all or part of its length.

As noted above, in some instances, the spacer can be omitted, and the sample chamber can be defined only by the substrate and the cover. See, e.g., U.S. Pat. No. 8,992,750.

Additionally or alternatively to using capillary action, the sample chamber can be augmented by other means, such as by applying a pressure on the sample fluid to push it into sample chamber, and/or creating a vacuum on sample chamber to pull the body sample fluid into the sample chamber. In addition, one or more surfaces of sample chamber can be formed from a hydrophilic material, provided with a coating of a hydrophilic material, or subjected to a hydrophilicity-increasing treatment to facilitate filling of sample chamber with the body fluid sample.

For example, the sample chamber may include a sorbent material. Examples of sorbent materials include, but are not limited to, polyester, nylon, cellulose, and cellulose derivatives such as nitrocellulose. When included, the sorbent material facilitates uptake of the body sample fluid by assisting in wicking the fluid into sample chamber. The use of a sorbent material also serves to further reduce the void volume of sample chamber receiving the body sample fluid.

FIG. 1 is a perspective view of an exemplary diagnostic test element 10. In the exemplary embodiment, the test element 10 includes a non-conductive support substrate 12, an electrical conductor (not shown) formed on the support substrate 12 that defines a plurality of electrode traces (not shown), a spacer 14 positioned on the support substrate 12, and a cover 16 positioned on the spacer 14. In some instances, the electrical conductor may form any number of electrode traces, electrodes and contact pads that enable the test element 10 to function as described herein and that are described in greater detail below.

As also shown in FIG. 1, the diagnostic test element 10 can have a substantially rectangular shape; however, any one of a number of forms that enable the test element 10 to function as described herein also are contemplated. In addition, the test element 10 can be any one of a plurality produced from rolls of material, sheets of material or any other material stock in accordance with the principles of this disclosure. In general, the material selection for fabricating the test element 10 includes any material that is sufficiently flexible for roll processing, but is rigid enough to give a useful stiffness to the finished test element 10.

In the exemplary embodiment, the support substrate 12 of the diagnostic test element 10 includes a first surface 18 facing the spacer 14 and a second surface 20 opposite the first surface 18. Moreover, the support substrate 12 has opposite first and second ends 22, 24 and opposite side edges 26, 28 that extend between the first and second ends 22, 24. In some instances, the first and second ends 22, 24 and the opposite side edges 26, 28 of the support substrate 12 form a generally rectangular shape. Alternatively, the first and second ends 22, 24 and the opposite side edges 26, 28 may be arranged to form any one of a variety of shapes and sizes that enable the test element 10 to function as described herein. In some instances, the support substrate 12 can be fabricated of a flexible polymer including, but not limited to, a polyester or polyimide, such as polyethylene naphthalate (PEN). Alternatively, the support substrate 12 can be fabricated from any other suitable materials that enable the support substrate 12 to function as described herein.

An electrical conductor forming electrode traces is provided on the first surface 18 of the support substrate 12. The electrical conductor may be fabricated from materials including, but not limited to, aluminum, carbon (e.g., graphite), cobalt, copper, gallium, gold, indium, iridium, iron, lead, magnesium, mercury (as an amalgam), nickel, niobium, osmium, palladium, platinum, rhenium, rhodium, selenium, silicon (e.g., highly doped polycrystalline silicon), silver, tantalum, tin, titanium, tungsten, uranium, vanadium, zinc, zirconium, and combinations thereof. In some instances, the electrode traces are isolated from the rest of the electrical conductor by laser ablation or laser scribing, both of which are well known in the art. In this manner, the electrode traces can be fabricated by removing the electrical conductor from an area extending around the electrodes either broadly, such as by broad field ablation, or minimally, such as by line scribing. Alternatively, the electrode traces may be fabricated by other techniques such as, for example, lamination, screen-printing, photolithography, etc.

In the exemplary embodiment, diagnostic test element 10 is a FWED test element, which has a capillary channel 30 or an inlet at the first end 22 of the support substrate. It is contemplated, however, that the capillary channel 30 also can be a conventional capillary channel (i.e., bounded on more than one side). In a FWED test element, the spacer 14 extends between the opposite side edges 26, 28 of the support substrate 12 to form the capillary channel 30 in part with a cover. It is contemplated that the spacer 14 may be fabricated of a single component or even a plurality of components. Regardless, the spacer 14 should include an end edge 32 substantially parallel to and facing the first end 22 of the support substrate 12, thereby defining a boundary of a capillary channel 30 by extending across the entire width of the support substrate 12. Alternatively, and as noted above, the end edge 32 may include multiple portions located between the first and second ends 22, 24 and the opposite side edges 26, 28 of the support substrate 12 to form a generally U-shaped pattern to define the boundary of the capillary channel 30 having a sample inlet at the first end 22 of the test element 10 (not shown). Other suitable embodiments contemplate an end edge 28 that forms hemi-ovular, semi-circular, or other shaped capillary channels, and the one or more of the portions of end edge 32 may include linear or non-linear edges along all or part of its length (not shown).

The spacer 14 is fabricated from an insulative material such as, for example, a flexible polymer including an adhesive coated polyethylene terephthalate (PET)-polyester. One particular non-limiting example of a suitable material includes a white PET film, both sides of which are coated with a pressure-sensitive adhesive. The spacer 14 may be constructed of a variety of materials and includes an inner surface 34 that may be coupled to the first surface 18 of the support substrate 12 using any one or a combination of a wide variety of commercially available adhesives. Additionally, when first surface 18 of the support substrate 12 is exposed and not covered by the electrical conductor, the cover 16 may be coupled to support the substrate 12 by welding, such as heat or ultrasonic welding. It also is contemplated that first surface 18 of the support substrate 12 may be printed with, for example, product labeling or instructions (not shown) for use of the test elements 10.

Further, in the exemplary embodiment, the cover 16 extends between the opposite side edges 26, 28 of the support substrate 12 and extends to the first end 22 of the support substrate 12. Alternatively, the cover 16 may extend beyond the first end 22 a predefined distance that enables the test element 10 to function as described herein. In the exemplary embodiment, the capillary channel 30 is therefore defined as the space between the cover 16 and the support substrate 12, bounded by the first end 22 and the opposite side edges 26, 28 of the support substrate 12 and the end edge 32 of the spacer 14.

The cover 16 can be fabricated from an insulative material such as, for example, a flexible polymer including an adhesive coated PET-polyester. One particular non-limiting example of a suitable material includes a transparent or translucent PET film. The cover 16 may be constructed of a variety of materials and includes a lower surface 36 that may be coupled to the spacer 14 using any one or a combination of a wide variety of commercially available adhesives. Additionally, the cover 16 may be coupled to the spacer 14 by welding, such as heat or ultrasonic welding.

The diagnostic test elements include an electrode system having a CE/WE electrode pair, one or more separate WEs, and one or more electrically conductive pathways and contact pads of an electrically conductive material provided on, for example, the first surface of the support such that the electrode systems are co-planar. However, it is contemplated that the electrode system can be formed on opposing surfaces such that one electrode system is on the first surface of the support and another electrode system is on an opposing surface of the cover. See, e.g., U.S. Pat. No. 8,920,628. Regardless, the electrically conductive material typically is arranged on the substrate in such a way to provide the one or more electrically conductive pathways. Particular arrangements of electrically conductive material may be provided using a number of techniques including chemical vapor deposition, laser ablation, lamination, screen-printing, photolithography, and combinations of these and other techniques. One particular method for removing portions of the conductive material include laser ablation or laser scribing, and more particularly broad field laser ablation, as disclosed in, for example, U.S. Pat. No. 7,073,246. In this manner, the electrode system can be fabricated by removing electrically conductive material from the substrate either broadly, such as by broad field ablation, or minimally, such as by line scribing. Alternatively, the electrode system may be fabricated by other techniques such as, for example, lamination, screen-printing, photolithography, etc.

Briefly, laser ablative techniques typically include ablating a conductive material such as a metallic layer or a multi-layer composition that includes an insulating material and a conductive material (e.g., a metallic-laminate of a metal layer coated on or laminated to an insulating material). The metallic layer may contain pure metals, alloys, or other materials, which are metallic conductors. Examples of metals or metallic-like conductors include, but are not limited to, aluminum, carbon (such as graphite and/or graphene), copper, gold, indium, nickel, palladium, platinum, silver, titanium, mixtures thereof, and alloys or solid solutions of these materials. In one aspect, the materials are selected to be essentially unreactive to biological systems, with non-limiting examples including, but not limited to, gold, platinum, palladium, carbon and iridium tin oxide. The metallic layer may be any desired thickness which, in one particular form, is about 500 Å.

With respect to the diagnostic test elements herein, exemplary electrically conductive pathways include two WEs, contact pads for each WE, and respective WE conductive trace portions that extend between and electrically couple each WE to its contact pad. Likewise, the electrically conductive pathways include a CE, contact pad for the CE, and CE conductive trace portions that extend between and electrically couple the CE to its contact pad. As used herein, a "working electrode" or "WE" means an electrode at which an analyte is electrooxidized or electroreduced with or without the agency of a mediator, while the term "counter electrode" or "CE" means an electrode that is paired with one or more WEs and through which passes an electrochemical current equal in magnitude and opposite in sign to the current passed through the WE. CE also includes counter electrodes that also function as reference electrodes (i.e., counter/reference electrodes).

The electrode system also can include one or more sample sufficiency electrodes (SSEs), sample sufficiency contact pads, and respective conductive trace portions that extend between and electrically couple the SSEs and SSE contact pads. If included, the SSEs can be used to implement a number of techniques for determining the sufficiency of a body fluid sample applied to the test elements. See, e.g., Int'l Patent Application Publication No. WO 2014/140170 and WO 2015/187580.

The electrode system also can include one or more test element integrity electrodes (IEs) that can be used to verify that the electrode systems are intact, as described in Int'l Patent Application Publication No. WO 2015/187580.

The electrode system also can include an information circuit in the form of a plurality of selectable resistive elements that form a resistance network, as described in Int'l Patent Application Publication No. WO 2013/017218 and US Patent Application Publication No. 2015/0362455. The information encoded in the resistance network can relate to an attribute of the test elements including, but not limited to, calibration information, test element type, manufacturing information and the like.

Figure 2A:
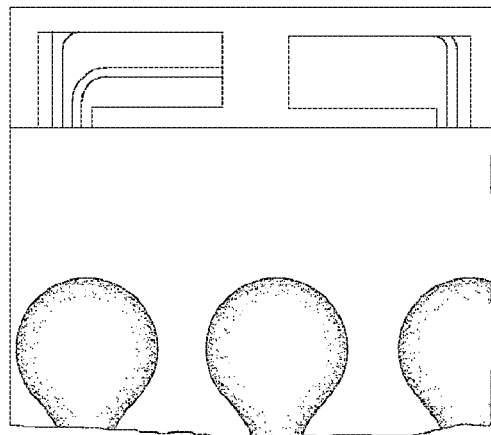
FIGS. 2A-C show exemplary electrode system configurations for multi-analyte test elements.

FIG. 2A shows an exemplary multi-analyte electrode system configuration for a diagnostic test element. In FIG. 2A, the sample chamber of the test element has an electrode system of electrically conductive material that includes a pair of SSEs positioned along a respective side edge of the non-conductive substrate, a CE/WE pair for measuring a first analyte positioned adjacent one of the SSEs and WE for measuring a second analyte positioned adjacent the other SSE, where the WE for measuring the second analyte has a greater working area than the WE for the first analyte.

Figure 2B:
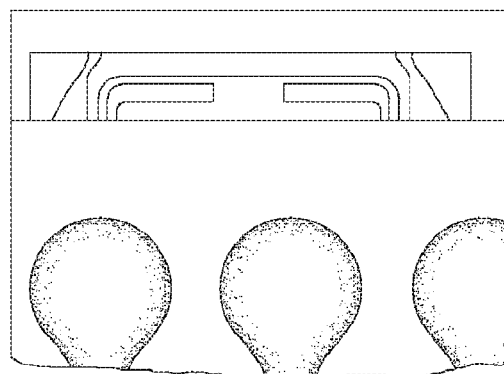

FIG. 2B shows another exemplary multi-analyte electrode system configuration for a diagnostic test element. In FIG. 2B, the sample chamber of the test element has an electrode system of electrically conductive material that includes a pair of SSEs positioned along a respective side edge of the non-conductive substrate, a CE/WE pair for measuring a first analyte and a WE for measuring the second analyte. In contrast to FIG. 2A, the CE in FIG. 2B extends across the sample chamber in front of both WEs. Additionally, the WEs have equivalent working areas.

Figure 2C:
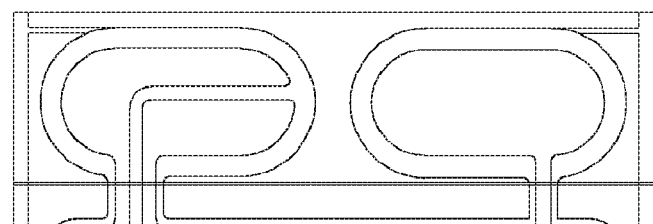

FIG. 2C shows yet another exemplary multi-analyte electrode system configuration for a diagnostic test element. In contrast to the configurations shown in FIGS. 2A-B, FIG. 2C does not include the SSEs and includes a WE for the second analyte having a working area greater than the WE for the first analyte.

The detection reagents that can be applied to the electrode systems are described in detail above.

The detection reagents described above can be formulated as a viscous solution that includes thickeners and thixotropic agents to enhance its physical properties. The thickeners are selected to provide a thick, liquid matrix having the remaining components homogeneously dispersed therein. The thickening and thixotropic agents also inhibit the liquid or semi-paste material from running or spreading over the surface of the substrate after each has been deposited and before they dries. After the detection reagents are deposited, they quickly dry to a readily hydratable reagent matrix.

As such, dry detection reagents can be provided by dissolving these components first in a solvent or solvent mixture and subsequently removing the solvent or mixture of solvents by a suitable treatment as described in further detail below.

As used herein, "dry" means that the reagent composition is essentially free of a solvent or a mixture of solvents. As used herein, "essentially free" means that at least about 85%, at least about 90%, at least about 91%, at least about 92%, at least about 93%, at least about 94%, at least about 95%, at least about 96%, at least about 97% or even at least 98% of the solvent or solvent mixture that was originally present in a solution of the reagent composition is removed from the composition. Accordingly, it is contemplated that the solvent or solvent mixture is present in the dry reagent composition in an amount of up to about 15%, up to about 10%, up to about 9%, up to about 8%, up to about 7%, up to about 6%, up to about 5%, up to about 4%, up to about 3% or up to about 2%. The aforementioned percentage values and the other percentage values referred to herein refer to percent by weight (w/w).

For example, the detection reagents can be applied via ink jetting over their respective electrode(s). See, e.g., U.S. Pat. No. 9,157,109. Alternatively, the detection reagents can be applied via drop on demand printing over their respective electrode(s). Alternatively still, the detection reagents can be applied via a PicoJet® Dispensing System (Nordson EFD) to deposit the detection reagent(s) in discrete areas of the sample chamber. Other contact or non-contact dispensing systems also can be used, which are described in the paragraphs below.

Alternatively still, the detection reagents can be applied via vacuum-assist slot die coating over their respective electrode(s). Methods of controlling detection reagent thickness and uniformity by vacuum-assist slot die coating are described in, for example, Int'l Patent Application Publication No. WO 2012/139767 and U.S. Pat. No. 7,749,437.

Additional details regarding exemplary diagnostic test element configurations that may be used herein are disclosed in, for example, Int'l Patent Application Publication Nos. WO 2014/037372, 2014/068022 and 2014/068024; US Patent Application Publication Nos. 2003/0031592 and 2006/0003397; U.S. Pat. Nos. 5,694,932; 5,271,895; 5,762,770; 5,948,695; 5,975,153; 5,997,817; 6,001,239; 6,025,203; 6,162,639; 6,207,000; 6,245,215; 6,271,045; 6,319,719; 6,406,672; 6,413,395; 6,428,664; 6,447,657; 6,451,264; 6,455,324; 6,488,828; 6,506,575; 6,540,890; 6,562,210; 6,582,573; 6,592,815; 6,627,057; 6,638,772; 6,755,949; 6,767,440; 6,780,296; 6,780,651; 6,814,843; 6,814,844; 6,858,433; 6,866,758; 7,008,799; 7,025,836; 7,063,774; 7,067,320; 7,238,534; 7,473,398; 7,476,827; 7,479,211; 7,510,643; 7,727,467; 7,780,827; 7,820,451; 7,867,369; 7,892,849; 8,180,423; 8,298,401; 8,329,026, as well as RE42560, RE42924 and RE42953.

Likewise, the diagnostic test elements can include one or more reflection layers of one or more pigments that have reflective properties such as, for example, white pigments such as titanium dioxide particles. In some instances, the at least one reflection layer can be on a surface of the substrate that faces away from the detection reagents, which can be in the form of test fields, thus serving as a sample application side. In this manner, the detection of the at least one analyte can take place through the substrate from a side opposite to the sample application side. To facilitate this design, the substrate can be completely or partially optically transparent for at least one excitation light irradiated into the detection reagents and/or transparent for at least one detection light reflected and/or emitted by the detection reagents, where a transparency is understood as a transparency of at least about 70%. In other instances, the liquid sample can be introduced laterally into the detection reagents (i.e., parallel to the layer structure).

A concern in multi-analyte diagnostic test elements is controlling for potential cross-talk in signals that can occur between or among the various detection reagents. Several methods of attenuating or avoiding cross-talk are known in the art and can be used in connection with the multi-analyte test elements disclosed herein. For example, one can control diffusion of components from one detection reagent matrix to the other by (1) using detection reagent formulations that swell but are not completely soluble (e.g. the matrix materials described above); (2) by spacing the detection reagents apart from one another; (3) by using physical barriers between the detection reagents (i.e., leaving residual conductive material or other materials; laser marking on the substrate); and/or (4) by using a short time frame to complete the measurement so that reagent diffusion is limited.

Analyte Measurement Devices, Apparatuses and Test Systems

Test systems can include an analyte measurement device and at least one multi-analyte diagnostic test elements as described above.

Figure 3:
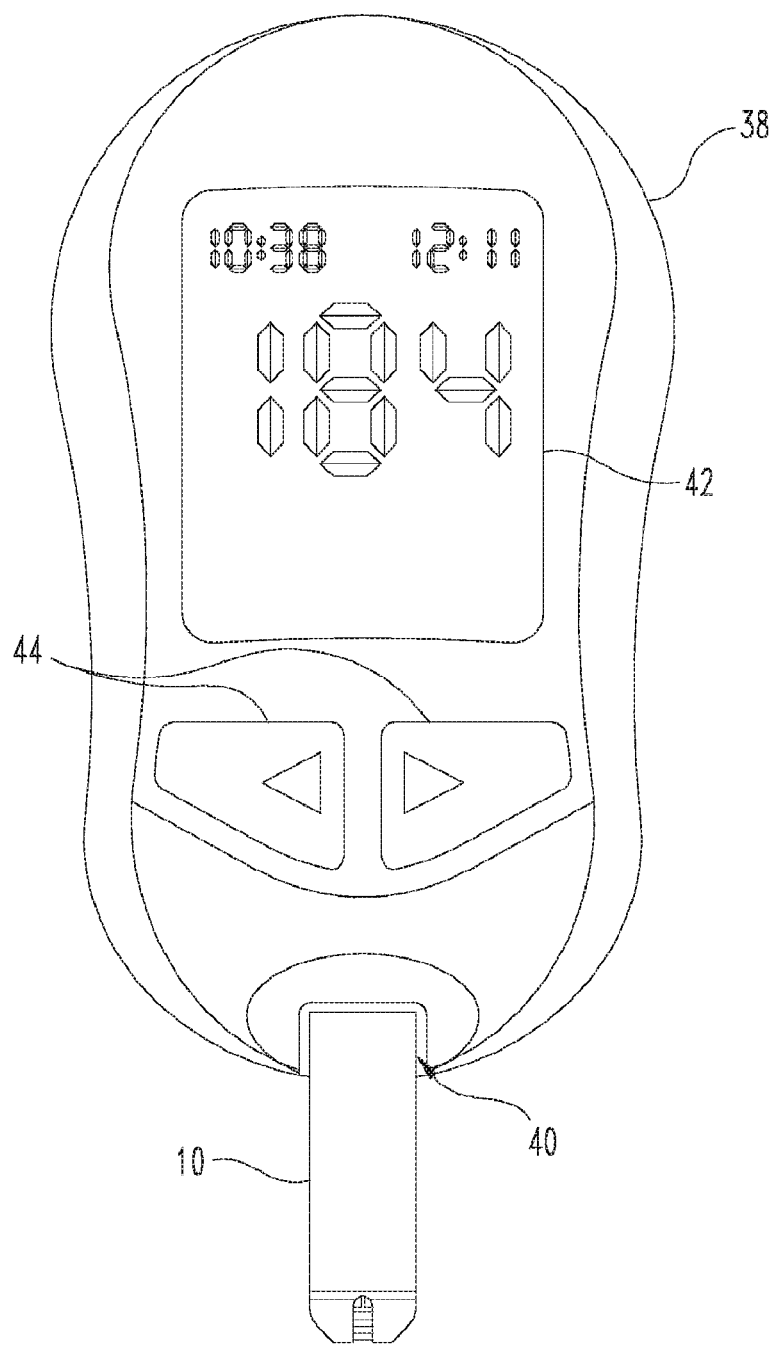
FIG. 3 shows an exemplary test system including a meter and a multi-analyte test element as described herein.

FIG. 3 shows an exemplary analyte measurement system including an analyte measuring device such as a test meter 38 operatively coupled with an electrochemical diagnostic test element 10. In particular, the test element is a multi-analyte diagnostic test element as described in detail above.

Typically, the meter 38 and the diagnostic test element 10 are operable to determine concentration of a plurality of analytes in a body fluid sample provided to the test element 10. In some instances, the sample may be a body fluid sample such as, for example, whole blood, plasma, serum, urine, or saliva. In other instances, the sample may be another type of fluid sample to be tested for the presence or concentration of one or more electrochemically reactive analyte(s) such as an aqueous environmental sample.

In FIG. 3, the diagnostic test element 10 is a single use test strip removably inserted into a connection terminal (or test element port) 40 of meter 38. In some instances, the test element 10 is configured as a dual analyte—glucose and ketone—test element and includes features and functionalities for electrochemically measuring glucose and ketones. In other instances, the test element 10 is configured to electrochemically measure other analytes such as, for example, amino acids, antibodies, bacteria, carbohydrates, drugs, lipids, markers, nucleic acids, peptides, proteins, toxins, viruses, and other analytes.

The meter 38 generally includes an entry (or input) means 44, a controller, a memory associated with the controller/microcontroller, and a programmable processor associated with the controller and connected with the memory. In addition, the meter includes an output such as an electronic display 42 that is connected to the processor and is used to display various types of information to the user including analyte concentration(s) or other test results. Furthermore, the meter 38 further includes associated test signal generating and measuring circuitry (not shown) that are operable to generate a test signal, to apply the signal to the test element 10, and to measure one or more responses of the test element 10 to the test signal. The processor also is connected with a test element port and is operable to process and record data in memory relating to detecting the presence and/or concentration of the analytes obtained through use of a multi-analyte test element as described herein. Test element port includes connectors configured to engage with contact pads of the electrical system. Moreover, the meter includes user entry means connected with the processor, which is accessible by a user to provide input to processor, where the processor is further programmable to receive input commands from user entry means and provide an output that responds to the input commands.

The processor also is connected with a communication module or link to facilitate wireless transmissions with the meter 38. In one form, the communication link may be used to exchange messages, warnings, or other information between the meter 38 and another device or party, such as a caseworker, caregiver, parent, guardian or healthcare provider, including nurses, pharmacists, primary or secondary care physicians and emergency medical professionals, just to provide a few possibilities. The communication link also can be utilized for downloading programming updates for meter 38. By way of non-limiting example, the communication link may be configured for sending and receiving information through mobile phone standard technology, including third-generation (3G) and fourth-generation (4G) technologies, or through BLUETOOTH®, ZIGBEE®, Wibree, ultra-wide band (UWB), wireless local area network (WLAN), General Packet Radio Service (GPRS), Worldwide Interoperability for Microwave Access (WiMAX or WiMAN), Wireless Medical Telemetry (WMTS), Wireless Universal Serial Bus (WUSB), Global System for Mobile communications (GSM), Short Message Service (SMS) or WLAN 802.11x standards.

The controller therefore can include one or more components configured as a single unit or of multi-component form and can be programmable, a state logic machine or other type of dedicated hardware, or a hybrid combination of programmable and dedicated hardware. One or more components of the controller may be of the electronic variety defining digital circuitry, analog circuitry, or both. As an addition or alternative to electronic circuitry, the controller may include one or more mechanical or optical control elements.

In some instances, which include electronic circuitry, the controller includes an integrated processor operatively coupled to one or more solid-state memory devices defining, at least in part, memory. In this manner, the memory contains operating logic to be executed by processor that is a microprocessor and is arranged for reading and writing of data in the memory in accordance with one or more routines of a program executed by the microprocessor.

In addition, the memory can include one or more types of solid-state electronic memory and additionally or alternatively may include the magnetic or optical variety. For example, the memory can include solid-state electronic random access memory (RAM), sequentially accessible memory (SAM) (such as the first-in, first-out (FIFO) variety or the last-in, first-out (LIFO) variety), programmable read only memory (PROM), electrically programmable read only memory (EPROM), or electrically erasable programmable read only memory (EEPROM); or a combination of any of these types. Also, the memory may be volatile, nonvolatile or a hybrid combination of volatile and nonvolatile varieties. Some or all of the memory can be of a portable type, such as a disk, tape, memory stick, cartridge, code chip or the like. Memory can be at least partially integrated with the processor and/or may be in the form of one or more components or units.

In some instances, the meter 38 may utilize a removable memory key, which is pluggable into a socket or other receiving means and which communicates with the memory or controller to provide information relating to calibration codes, measurement methods, measurement techniques, and information management. Examples of such removable memory keys are disclosed in, for example, U.S. Pat. Nos. 5,366,609 and 5,053,199.

The controller also can include signal conditioners, filters, limiters, analog-to-digital (A/D) converters, digital-to-analog (D/A) converters, communication ports, or other types of operators as would occur to one of skill in the art.

Returning to the entry means 44, it may be defined by a plurality of push-button input devices, although the entry means 44 may include one or more other types of input devices like a keyboard, mouse or other pointing device, touch screen, touch pad, roller ball, or a voice recognition input subsystem.

Likewise, the display 42 may include one or more output means like an operator display that can be of a cathode ray tube (CRT) type, liquid crystal display (LCD) type, plasma type, organic light emitting diode (OLED) type, a printer, or the like. Other input and display means can be included such as loudspeakers, voice generators, voice and speech recognition systems, haptic displays, electronic wired or wireless communication subsystems, and the like.

As indicated above, the test element port 40 includes connectors configured to engage with contact pads of the electrode system of the test elements described herein. The connection between meter 38 and the diagnostic test element 10 is used to apply a test signal having a potential or a series of potentials across the electrodes of the electrode system and to subsequently receive electrochemical signals that are produced by the detection reagents in the presence of the analytes of interest and can be correlated to the concentration of the analytes. In this manner, the processor is configured to evaluate the electrochemical signals to assess the presence and/or concentration of the analytes, where the results of the same may be stored in the memory.

In some instances, the meter 38 can be configured as a blood glucose measurement meter and includes features and functionalities of the ACCU-CHEK® AVIVA® meter as described in the booklet "Accu-Chek® Aviva Blood Glucose Meter Owner's Booklet" (2007), portions of which are disclosed in U.S. Pat. No. 6,645,368. In other instances, meter 38 can be configured to electrochemically measure one or more other analytes such as, for example, amino acids, antibodies, bacteria, carbohydrates, drugs, lipids, markers, nucleic acids, proteins, peptides, toxins, viruses, and other analytes. Additional details regarding exemplary meters configured for use with electrochemical measurement methods are disclosed in, for example, U.S. Pat. Nos. 4,720,372; 4,963,814; 4,999,582; 4,999,632; 5,243,516; 5,282,950; 5,366,609; 5,371,687; 5,379,214; 5,405,511; 5,438,271; 5,594,906; 6,134,504; 6,144,922; 6,413,213; 6,425,863; 6,635,167; 6,645,368; 6,787,109; 6,927,749; 6,945,955; 7,208,119; 7,291,107; 7,347,973; 7,569,126; 7,601,299; 7,638,095 and 8,431,408.

In addition to the meter, the test systems include one more multi-analyte diagnostic test elements as described in detail above.

Another component that can be included in the test systems includes lancing devices for obtaining a body fluid sample. Examples of lancing devices are described in, for example, Int'l Patent Application Publication Nos. WO 2012/089523 and WO 2012/089524. In some instances, the lancing device can be integrated into the meter. See, e.g., id.

Multi-Analyte Measuring Methods

The measuring methods disclosed herein largely utilize amperometry; however, it is contemplated that the methods can be used with other electrochemical measuring techniques (e.g., coulometry, potentiometry or voltammetry). Moreover, the measuring methods can be implemented using advanced microprocessor-based algorithms and processes that result in dramatically improved system performance. These measuring methods also offer flexibility and number of ways to create algorithms that can achieve improved performance such as 10/10 performance. As used herein, "10/10 performance" means, for example, that a measured blood glucose concentration is within about ±10% of the actual blood glucose concentration for glucose concentrations >100 mg/dL, and within ±10 mg/dL of the actual blood glucose concentration for glucose concentrations <100 mg/dL.

The measuring methods can include the steps described herein, and these steps may be, but not necessarily, carried out in the sequence as described. Other sequences, however, also are conceivable. Furthermore, individual or multiple steps may be carried out either in parallel and/or overlapping in time and/or individually or in multiply repeated steps. Moreover, the methods may include additional, unspecified steps.

In general, the measuring methods begin by obtaining a body fluid sample having or suspected of having one or more analytes of interest therein. Examples of body fluids include, but are not limited to, blood, interstitial fluid, saliva, tears and urine. As used herein, "blood" means whole blood and its cell-free components, namely plasma and serum.

When the multi-analyte diagnostic test elements are configured for testing glucose and ketones, the body sample fluid may be fresh capillary blood obtained by lancing a fingertip or approved alternate sites (e.g., forearm, palm, ear lobe, upper arm, calf and thigh). Moreover, the bodily fluid sample containing the analyte(s) of interest may be acquired and delivered to the test elements in any fashion. As such, the measuring methods principally relate to in vitro methods. For example, a blood sample may be obtained in conventional fashion by incising the skin, such as with a lancet, needle or scalpel, and then contacting the test element with blood sample that appears at the skin surface. Alternatively, the test elements can be used in connection with control fluids that are used in conventional fashion to verify the integrity of the test system.

In general, the diagnostic test elements are operable for assessing the targeted analytes while only using a very small volume of a body fluid sample. In this manner, only a slight skin incision is necessary to produce the volume of body fluid required for the test, and the pain and other concerns with such method can be minimized or eliminated.

After the body fluid sample has been applied to the dosing end of the diagnostic test element and rehydrates the detection reagents, the methods include applying an electrical test sequence to the electrode system of the test element. Such a test sequence can be supplied by the meter from its connection terminals to one or more contact pads of the electrode system.

In general, electrical test sequences include one or more AC blocks (optional) and/or one or more DC blocks as are known in the art. See, e.g., Int'l Patent Application Publication Nos. WO 2014/140718; WO 2014/140164; WO 2014/140170; WO 2014/140172; WO 2014/140173; and WO 2014/140177.

Figure 4A:
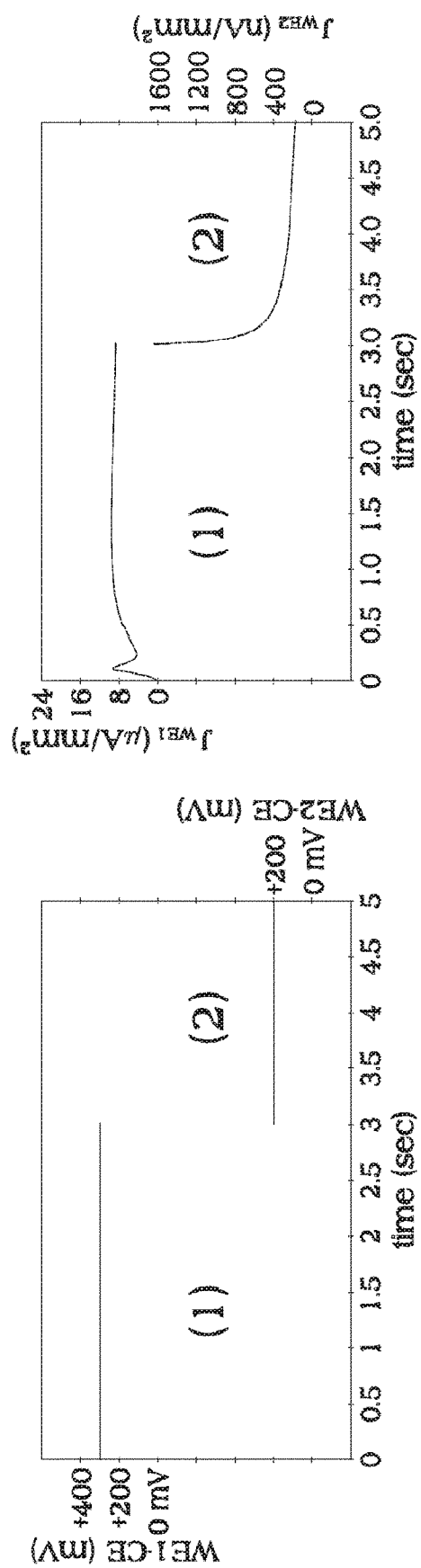
FIGS. 4A-F show exemplary electrical test sequences for multi-analyte measurements. Specifically.
Figure 4B:
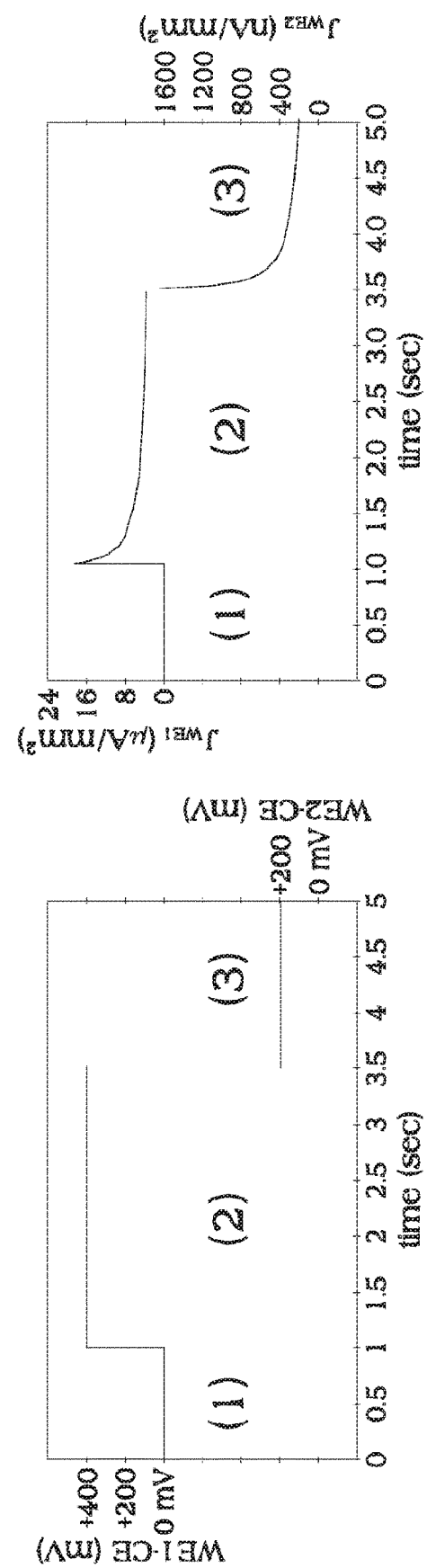

If included, the AC block of low-amplitude signals in connection with a DC block and measuring current responses thereto. FIGS. 4A-F show exemplary test sequences that may be used in connection with SMBG and other test systems. As shown in FIGS. 4A-B, the test sequence can include one or more blocks of AC and or DC potentials, which are described in greater detail below.

With respect to the AC block, it can include a plurality of AC segments such as, for example, from about 2 segments to about 10 segments, from about 3 segments to about 9 segments, from about 4 segments to about 8 segments, from about 5 segments to about 7 segments, or about 6 segments. In other instances, the AC block can include about 2 segments, about 3 segments, about 4 segments, about 5 segments, about 6 segments, about 7 segments, about 8 segments, about 9 segments, or about 10 segments. In still other instances, the AC block can have more than 10 segments, that is, about 15 segments, about 20 segments, or about 25 segments. In yet other instances, the AC block can include 1 segment, where the segment has multiple low-frequency AC signals applied simultaneously.

One of skill in the art understands that the number of AC segments will be limited by the complexity of the response, the associated frequency range and time available to perform the measurements. Higher frequencies generally require high bandwidth electronics and faster sampling, whereas lower frequencies take longer and typically are noisier. The maximum number of segments therefore will be a compromise of these parameters, choosing the minimum count and frequency span needed to discriminate the sample and environmental and/or confounding factors of interest.

The frequency of each signal in each segment of the AC block can be from about 1 kHz to about 20 kHz, from about 2 kHz to about 19 kHz, from about 3 kHz to about 18 kHz, from about 4 kHz to about 17 kHz, from about 5 kHz to about 16 kHz, from about 6 kHz to about 15 kHz, from about 7 kHz to about 14 kHz, from about 8 kHz to about 13 kHz, from about 9 kHz to about 12 kHz or from about 10 kHz to about 11 kHz. In other instances, the frequency of each segment in the AC block can be about 1 kHz, about 2 kHz, about 3 kHz, about 4 kHz, about 5 kHz, about 6 kHz, about 7 kHz, about 8 kHz, about 9 kHz, about 10 kHz, about 11 kHz, about 12 kHz, about 13 kHz, about 14 kHz, about 15 kHz, about 16 kHz, about 17 kHz, about 18 kHz, about 19 kHz, or about 20 kHz. In still other instances, the frequency of each signal in each segment of the AC block can be more than 20 kHz, that is, about 30 kHz, about 40 kHz, or about 50 kHz. In some instances, one or more of the segments can have the same frequency, whereas in other instances each segment has a distinct frequency from the other segments. Four frequencies, however, generally is adequate. The exact frequencies employed can be readily generated by simple integer division of a measurement system clock's maximum frequency.

A maximum frequency limit for a signal in a segment of the AC block, however, can be up to about 100 kHz for an inexpensive, battery-powered handheld instrument such as the meter. Beyond that, the increasing demands on analog bandwidth, sampling rate, storage and processing speed quickly add up, while the imaginary portion of a typical biosensor response becomes increasingly smaller with frequency. Lower frequencies have longer periods and take longer times to sample with comparable accuracy.

The AC block typically includes at least two different low-amplitude signals. For example, the AC block can include two (2) segments at two (2) frequencies such as, for example, about 10 kHz or about 20 kHz followed by about 1 kHz or about 2 kHz. In other instances, the AC block includes a plurality of low-amplitude signals. For example, the AC block can have five (5) segments at four (4) frequencies such as, for example, about 10 kHz, about 20 kHz, about 10 kHz, about 2 kHz and about 1 kHz. Alternatively, the AC block can have four (4) segments at four (4) frequencies such as, for example, about 20 kHz, about 10 kHz, about 2 kHz and about 1 kHz. Alternatively, the AC block can have four (4) frequencies applied simultaneously at about 10 kHz, about 20 kHz, about 10 kHz, about 2 kHz and about 1 kHz. Alternately still, the AC block can have a multi-frequency excitation waveform that simultaneously applies the desired low-amplitude AC signals. The AC frequencies may be applied sequentially, or combined and applied simultaneously and analyzed via Fourier Transform.

The block of low-amplitude AC signals can be applied for about 500 msec to about 1.5 sec, about 600 msec to about 1.25 sec, about 700 msec to about 1000 msec, or about 800 msec to about 900 msec. Alternatively, the block of low-amplitude AC signals can be applied for about 500 msec, about 600 msec, about 700 msec, about 800 msec, about 900 msec, about 1000 msec, about 1.25 sec or about 1.5 sec. In particular, the block of low-amplitude AC signals can be applied for about 100 msec to about 300 msec.

One of skill in the art, however, understands that the number, frequency, duration and order of the AC segments can be varied.

AC current response information can be obtained at any time during a test sequence. Impedance results at lower frequencies may be influenced by analyte concentration if obtained after an electrochemical cell is DC polarized. In some instances, a series of AC current response measurements can be obtained early in the test sequence. Measurements taken shortly after a fluidic sample is applied to a test element will be influenced by diffusion, temperature and reagent solubility. In other instances, the AC response current measurements can be obtained at a sufficient time after an adequate sample has been applied to allow the response to stabilize, and avoid the transient response in the first second. Likewise, response current measurements can be made at one or more frequencies. Due to their capacitive nature, multiple AC measurements separated by a frequency octave or decade may offer different sensitivities or easier manipulation.

The response information to such an AC block can be used to assess diffusion, temperature and reagent solubility prior to initiating the analyte measurements. Consequently, the response information to the AC block can be used to correct for confounding variables such as Hct and/or temperature or to determine the condition of the test element and its suitability for providing an accurate result.

Additional details regarding exemplary AC blocks in electrochemical measurement methods are disclosed in, for example, U.S. Pat. Nos. 7,338,639; 7,390,667; 7,407,811; 7,417,811; 7,452,457; 7,488,601; 7,494,816; 7,597,793; 7,638,033; 7,751,864; 7,977,112; 7,981,363; 8,148,164; 8,298,828; 8,377,707 and 8,420,404.

With respect to one exemplary DC block for the multi-analyte test sequence, it can include a plurality of pulses such as, for example, from about 2 pulses to about 10 pulses, from about 3 pulses to about 9 pulses, from about 4 pulses to about 8 pulses, from about 5 pulses to about 7 pulses, or about 6 pulses. In other instances, the DC block can include about 2 pulses, about 3 pulses, about 4 pulses, about 5 pulses, about 6 pulses, about 7 pulses, about 8 pulses, about 9 pulses, or about 10 pulses. In still other instances, the DC block can have more than 10 pulses, that is, about 15 pulses, about 20 pulses, or about 25 pulses. As used herein, "pulse" means at least one excitation and one recovery period.

The DC block typically includes a constantly applied potential difference that alternates between about 0 mV and about +450 mV potential difference, or other slowly time-varying potential difference that can be analyzed by traditional DC electrochemical methods. One of skill in the art, however, understands that the range for the applied potential difference can, and will, vary depending upon the analyte and reagent chemistry used. As such, excitation pulse potential can be greater-than, less-than or equal to about +450 mV. Examples of excitation potentials include, but are not limited to, 50 mV, 75 mV, 100 mV, 125 mV, 150 mV, 175 mV, 200 mV, 225 mV, 250 mV, 275 mV, 300 mV, 325 mV, 350 mV, 375 mV, 400 mV, 425 mV, 450 mV, 475 mV, 500 mV, 525 mV, 550 mV, 575 mV, 600 mV, 625 mV, 650 mV, 675 mV, 700 mV, 725 mV. 750 mV, 775 mV, 800 mV, 825 mV, 850 mV, 875 mV, 900 mV, 925 mV, 950 mV, 975 mV or 1000 mV.

Regardless of the number, each DC pulse can be applied for about 50 msec to about 500 msec, about 60 msec to about 450 msec, about 70 msec to about 400 msec, about 80 msec to about 350 msec, about 90 msec to about 300 msec, about 100 msec to about 250 msec, about 150 msec to about 200 msec, or about 175 msec. Alternatively, each pulse can be applied for about 50 msec, about 60 msec, about 70 msec, about 80 msec, about 90 msec, about 100 msec, about 125 msec, about 150 msec, about 175 msec, about 200 msec, about 225 msec, about 250 msec, about 275 msec, about 300 msec, about 325 msec, about 350 msec, about 375 msec, about 400 msec, about 425 msec, about 450 msec, about 475 msec or about 500 msec. In particular, each DC pulse at +450 mV can be applied for about 250 msec, and each DC pulse at 0 mV can be applied for about 500 msec. Alternatively still, each pulse can be applied for less than about 50 msec or more than about 500 msec.

Generally, the ramp rate of each DC pulse is selected to provide about 50% or greater reduction in peak current relative to the peak current provided by a nearly ideal potential transition. In some instances, each pulse can have the same ramp rate. In other instances, some pulses can have the same ramp rate and other pulses can have a different ramp rate. In still other instances, each pulse has its own ramp rate. For example, effective ramp rates can be from about 5 mV/msec to about 75 mV/msec or from about 10 mV/msec to about 50 mV/msec, 15 mV/msec to about 25 mV/msec, or about 20 mV/msec. Alternatively, the ramp rate can be about 5 mV/msec, about 10 mV/msec, about 15 mV/msec, about 20 mV/msec, about 25 mV/msec, about 30 mV/msec, about 35 mV/msec, about 40 mV/msec, about 45 mV/msec, about 50 mV/msec, about 55 mV/msec, about 60 mV/msec, about 65 mV/msec, about 70 mV/msec, or about 75 mV/msec. In particular, the ramp rate can be from about 40 mV/msec to about 50 mV/msec.

In the DC block, the applied DC potential can be fixed at about 0 mV between pulses to provide a recovery pulse, thus making it a generally continuous excitation waveform. This is in contrast to test sequences generally known in the art that prescribe the use of an open circuit between positive DC pulses, thereby excluding the possibility of collecting and analyzing the current between positive pulses. As used herein, "recovery pulse" means a zero-potential pulse (e.g., about −10 mV to about +10 mV) applied for an adequately long recovery period in which the electrochemical reaction with the analyte of interested (e.g., glucose) is turned "off," thereby allowing the system to return to a fixed starting point before subsequent interrogation with another positive DC pulse.

An exemplary DC block therefore can alternate (i.e., pulse) between about 0 mV and about +450 mV (in biamperometric mode).

The response information to such a DC block can be used to assess a first analyte concentration or presence, such as a glucose concentration or presence. Additionally, information such as a recovery current response, shape and/or magnitude from the DC block potentials can be used to correct for not only Hct and/or temperature but also wetting of the reagent and sample diffusion, as well as variations in detection reagent thickness.

Like the AC block, one of skill in the art understands that the number, potential, duration and order of the DC pulses can be varied.

With respect to another exemplary DC block for the multi-analyte test sequence, it can include a waveform having plurality of intervals such as, for example, from about 2 intervals to about 10 intervals, from about 3 intervals to about 9 intervals, from about 4 intervals to about 8 intervals, from about 5 intervals to about 7 intervals, or about 6 intervals. In other instances, the waveform can include about 1 interval, about 2 intervals, about 3 intervals, about 4 intervals, about 5 intervals, about 6 intervals, about 7 intervals, about 8 intervals, about 9 intervals, or about 10 intervals. In still other instances, the waveform can have more than 10 intervals, that is, about 15 intervals, about 20 intervals, or about 25 intervals. The number of waveform intervals, however, typically is limited by the available time for the test sequence.

The waveform intervals can be at a potential that alternates or cycles between a positive potential and a negative potential (or vice versa). For example, the potential can alternate from about −450 mV to about +450 mV, from about −425 mV to about +425 mV, from about −400 mV to about +400 mV, from about −375 mV to about +375 mV, from about −350 mV to about +350 mV, from about −325 mV to about +325 mV, from about −300 mV to about +300 mV, from about −275 mV to about +275 mV, from about −250 mV to about +250 mV, from about −225 mV to about +225 mV, from about −200 mV to about +200 mV, from about −175 mV to about +175 mV, from about −150 mV to about +150 mV, from about −125 mV to about +125 mV, from about −100 mV to about +100 mV, from about −75 mV to about +75 mV, or from about −50 my to about +50 mV. In some instances, one or more of the successive cycles can have the same potential, whereas in other instances the successive cycles have a distinct potential from the other segments.

Regardless of the number, each waveform interval can be applied for about 100 msec to about 5 sec, from about 200 msec to about 4 sec, from about 300 msec to about 3 sec, from about 400 msec to about 2 sec, from about 500 msec to about 1 sec, from about 600 msec to about 900 msec, or from about 700 msec to about 800 msec. Alternatively, each waveform interval can be applied for about 100 msec, about 150 msec, about 200 msec, about 250 msec, about 300 msec, about 350 msec, about 400 msec, about 450 msec, about 500 msec, about 550 msec, about 600 msec, about 650 msec, about 700 msec, about 750 msec, about 800 msec, about 850 msec, about 900 msec, about 950 msec, about 1 sec, about 1.5 sec, about 2 sec, about 2.5 sec, about 3 sec, about 3.5 sec, about 4 sec, about 4.5 sec, or about 5 sec. In particular, each waveform interval at about −450 mV can be applied for about 100 msec to about 200 msec, and each waveform interval at about +450 mV can be applied for about 100 msec to about 200 msec. Alternatively still, each waveform interval can be applied for less than about 100 msec or more than about 5 sec.

In some instances, the waveform intervals can have the same ramp rates. In other instances, some waveform intervals can have the same ramp rate and other waveform intervals can have a different ramp rate. In still other instances, each waveform interval has its own ramp rate. For example, the ramp rate can be from about 0.5 mV/msec to <45 mV/msec. Alternatively, the ramp rate of each interval can be from about 1 mV/msec to about 40 mV/msec, from about 2 mV/msec to about 30 mV/msec, from about 3 mV/msec to about 20 mV/msec, from about 4 mV/msec to about 19 mV/msec, from about 5 mV/msec to about 18 mV/msec, from about 6 mV/msec to about 17 mV/msec, from about 7 mV/msec to about 16 mV/msec, from about 8 mV/msec to about 15 mV/msec, from about 9 mV/msec to about 14 mV/msec, or from about 10 mV/msec to about 13 mV/msec, or about 11 mV/msec to about 12 mV/msec. Alternatively, the ramp rate of each intervals can be about 0.5 mV/msec, 1 mV/msec, about 2 mV/msec, about 3 mV/msec, about 4 mV/msec, about 5 mV/msec, about 6 mV/msec, about 7 mV/msec, about 8 mV/msec, about 9 mV/msec, about 10 mV/msec, about 11 mV/msec, about 12 mV/msec, about 13 mV/msec, about 14 mV/msec, about 15 mV/msec, about 16 mV/msec, about 17 mV/msec, about 18 mV/msec, about 19 mV/msec, about 20 mV/msec, about 25 mV/msec, about 30 mV/msec, about 35 mV/msec, about 40 mV/msec, or about 45 mV/msec. In particular, the ramp rate is between about 3 mV/msec and about 9 mV/msec, such as about 5.1 mV/msec or about 7.15 mV/msec.

In some instances, the waveform can be a triangular waveform, trapezoidal waveform, sinusoidal waveform or combinations thereof.

Such a DC block can be used to assess a second analyte's concentration or presence, such as a ketone concentration or presence. Additionally, information such as a recovery current response, shape and/or magnitude from the DC block potentials can be used to assess detection reagent health and/or presence of certain interferents such as antioxidants (e.g., ascorbate, citric acid, deferoxamine (DFO), glutathione, N-acetylcysteine (NAC), pyrrolidine dithiocarbamate (PDTC), trylizad-mesylate (TLM) and uric acid).

As above, one of skill in the art understands that the number, potential, duration and order of the DC pulses can be varied.

With respect to a further exemplary DC block for the multi-analyte test sequence, it can include a waveform having plurality of intervals such as, for example, from about 2 intervals to about 10 intervals, from about 3 intervals to about 9 intervals, from about 4 intervals to about 8 intervals, from about 5 intervals to about 7 intervals, or about 6 intervals. In other instances, the waveform can include about 1 interval, about 2 intervals, about 3 intervals, about 4 intervals, about 5 intervals, about 6 intervals, about 7 intervals, about 8 intervals, about 9 intervals, or about 10 intervals. In still other instances, the waveform can have more than 10 intervals, that is, about 15 intervals, about 20 intervals, or about 25 intervals. The number of waveform intervals, however, typically is limited by the available time for the test sequence.

The waveform intervals can be at a potential that alternates or cycles between a positive potential and a negative potential (or vice versa). For example, the potential can alternate from about 0 mV to about +250 mV, from about 0 mV to about +225 mV, from about 0 mV to about +200 mV, from about 0 mV to about +175 mV, from about 0 mV to about +150 mV, from about 0 mV to about +125 mV, from about −0 mV to about +100 mV. In other instances, the potential can be maintained at about 250 mV, at about 225 mV, at about 200 mV, at about 175 mV, at about 150 mv, at about 125 mV, or at about 100 mV. In some instances, one or more of the successive cycles can have the same potential, whereas in other instances the successive cycles have a distinct potential from the other segments.

Regardless of the number, each waveform interval can be applied for about 100 msec to about 5 sec, from about 200 msec to about 4 sec, from about 300 msec to about 3 sec, from about 400 msec to about 2 sec, from about 500 msec to about 1 sec, from about 600 msec to about 900 msec, or from about 700 msec to about 800 msec. Alternatively, each waveform interval can be applied for about 100 msec, about 150 msec, about 200 msec, about 250 msec, about 300 msec, about 350 msec, about 400 msec, about 450 msec, about 500 msec, about 550 msec, about 600 msec, about 650 msec, about 700 msec, about 750 msec, about 800 msec, about 850 msec, about 900 msec, about 950 msec, about 1 sec, about 1.5 sec, about 2 sec, about 2.5 sec, about 3 sec, about 3.5 sec, about 4 sec, about 4.5 sec, or about 5 sec. In particular, each waveform interval at about −450 mV can be applied for about 100 msec to about 200 msec, and each waveform interval at about +450 mV can be applied for about 100 msec to about 200 msec. Alternatively still, each waveform interval can be applied for less than about 100 msec or more than about 5 sec.

In some instances, the waveform intervals can have the same ramp rates. In other instances, some waveform intervals can have the same ramp rate and other waveform intervals can have a different ramp rate. In still other instances, each waveform interval has its own ramp rate. For example, the ramp rate can be from about 0.5 mV/msec to <45 mV/msec. Alternatively, the ramp rate of each interval can be from about 1 mV/msec to about 40 mV/msec, from about 2 mV/msec to about 30 mV/msec, from about 3 mV/msec to about 20 mV/msec, from about 4 mV/msec to about 19 mV/msec, from about 5 mV/msec to about 18 mV/msec, from about 6 mV/msec to about 17 mV/msec, from about 7 mV/msec to about 16 mV/msec, from about 8 mV/msec to about 15 mV/msec, from about 9 mV/msec to about 14 mV/msec, or from about 10 mV/msec to about 13 mV/msec, or about 11 mV/msec to about 12 mV/msec. Alternatively, the ramp rate of each intervals can be about 0.5 mV/msec, 1 mV/msec, about 2 mV/msec, about 3 mV/msec, about 4 mV/msec, about 5 mV/msec, about 6 mV/msec, about 7 mV/msec, about 8 mV/msec, about 9 mV/msec, about 10 mV/msec, about 11 mV/msec, about 12 mV/msec, about 13 mV/msec, about 14 mV/msec, about 15 mV/msec, about 16 mV/msec, about 17 mV/msec, about 18 mV/msec, about 19 mV/msec, about 20 mV/msec, about 25 mV/msec, about 30 mV/msec, about 35 mV/msec, about 40 mV/msec, or about 45 mV/msec. In particular, the ramp rate is between about 3 mV/msec and about 9 mV/msec, such as about 5.1 mV/msec or about 7.15 mV/msec.

In some instances, the waveform can be a triangular waveform, trapezoidal waveform, sinusoidal waveform or combinations thereof.

The response information to such a DC block can be used to assess a second analyte's concentration or presence, such as a ketone concentration or presence.

As above, one of skill in the art understands that the number, potential, duration and order of the DC pulses can be varied.

An exemplary multi-analyte test sequence is shown in FIG. 4A (left panel), which includes (1) a first fixed DC potential difference between a first electrode pair dedicated to measuring a first analyte, followed by (2) a second fixed DC potential difference between a second electrode pair dedicated to measuring a second analyte. Advantageously, by measuring the analytes sequentially only one potentiostat is required. The sequence order can be determined by the analyte that benefits from a longer reaction time. As such, the first analyte is measured kinetically, while the second analyte's WE remains open circuited. Subsequently, the first analyte's WE is open circuited, while the second analyte's WE is connected to the potentiostat. The potential applied in (1) and (2) may be different depending on the mediator. A selectable potentiostat gain may be advantageous if the physiological levels are significantly different. FIG. 4A (right panel) shows an exemplary response to the test sequence shown in FIG. 4A (left panel).

An alternative exemplary multi-analyte test sequence is shown in FIG. 4B (left panel), which includes (1) a delay after a sample is introduced to the test element to allow the reactions to proceed, during which an open circuit or near 0 V potential difference is maintained between both electrode pairs, (2) a first fixed DC potential difference sufficient to generate a faradaic current between a first electrode pair, dedicated to measuring a first analyte, followed by (3) a second fixed DC potential difference sufficient to generate a faradaic current between a second electrode pair dedicated to measuring a second analyte. FIG. 4B (right panel) shows an exemplary response to the test sequence shown in FIG. 4B (left panel).

Figure 4C:
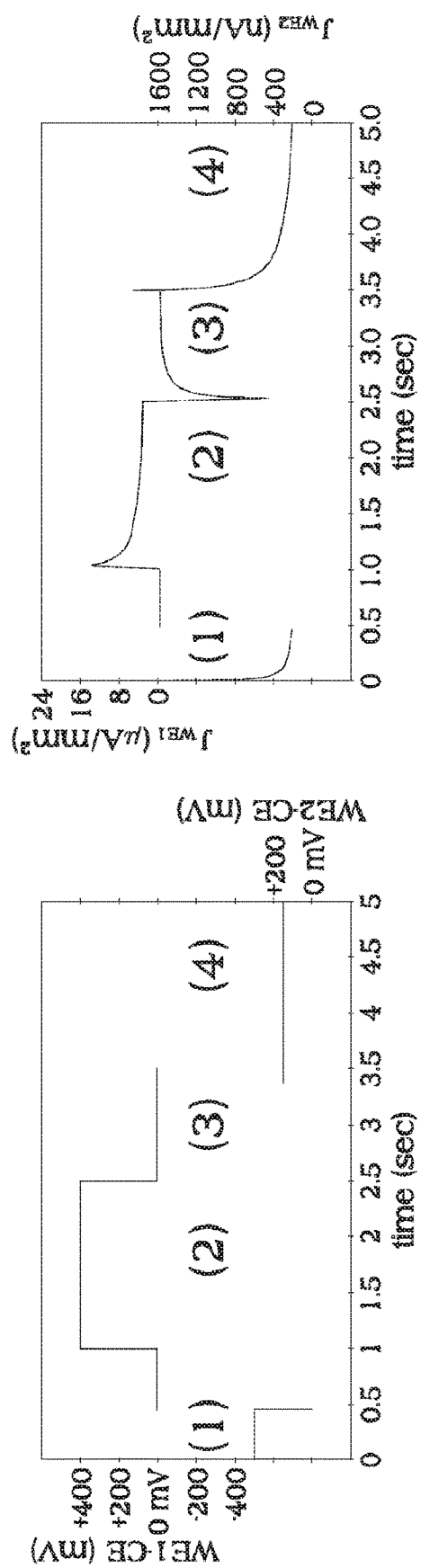

An alternative exemplary multi-analyte test sequence is shown in FIG. 4C (left panel), which includes (1) a delay after a sample is introduced to the test element to allow the reactions to proceed, during which an open circuit or near 0 V potential difference is maintained between both electrode pairs, (2) a first fixed DC potential difference sufficient to generate a faradaic current between a first electrode pair, dedicated to measuring a first analyte, followed by (3) a near 0 V DC potential difference between the first electrode pair to allow the current to return to 0, then (4) a second fixed DC potential difference sufficient to generate a faradaic current between a second electrode pair dedicated to measuring a second analyte. FIG. 4C (right panel) shows an exemplary response to the test sequence shown in FIG. 4C (left panel).

Figure 4D:
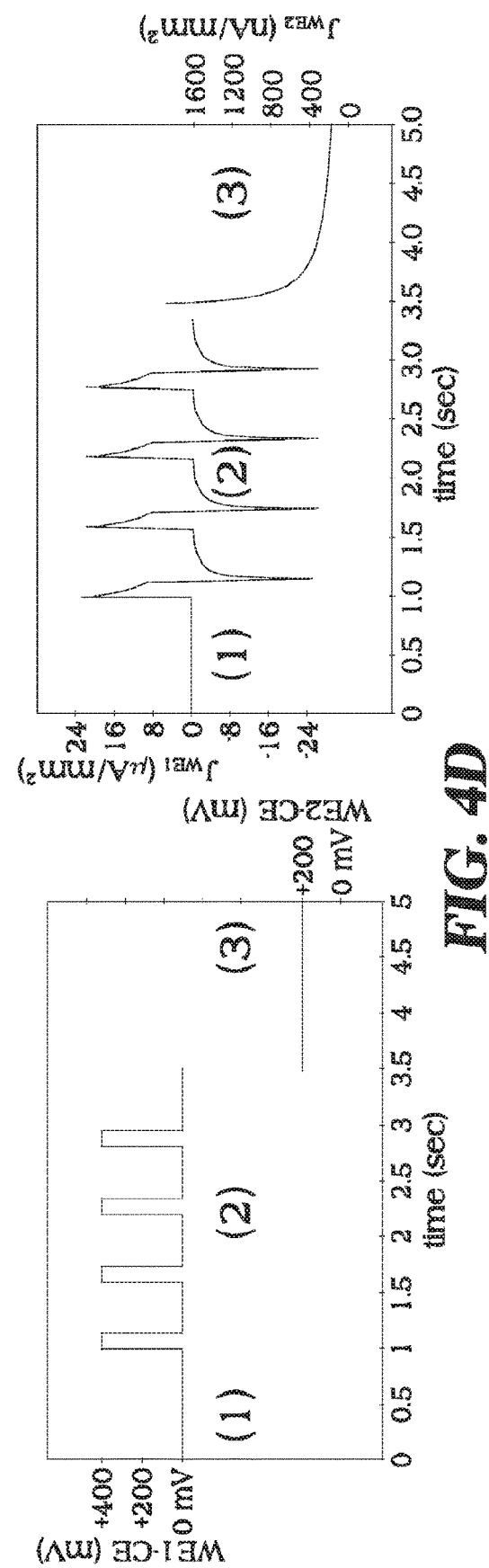

An alternative exemplary multi-analyte test sequence is shown in FIG. 4D (left panel), which includes (1) a delay after a sample is introduced to the test element to allow the reactions to proceed, during which an open circuit or near 0 V potential difference is maintained between both electrode pairs, (2) a first DC block of short-duration (e.g., about 50-500 msec) about +450 mV pulses separated by similarly short-duration (e.g., about 50-500 msec) recovery intervals during which about 0 mV potential difference is applied, followed by (3) a second DC block applying a fixed potential difference of about +175 mV following an open circuit between a second electrode pair dedicated to measuring a second analyte. FIG. 4D (right panel) shows an exemplary response to the test sequence shown in FIG. 4D (left panel).

Figure 4E:
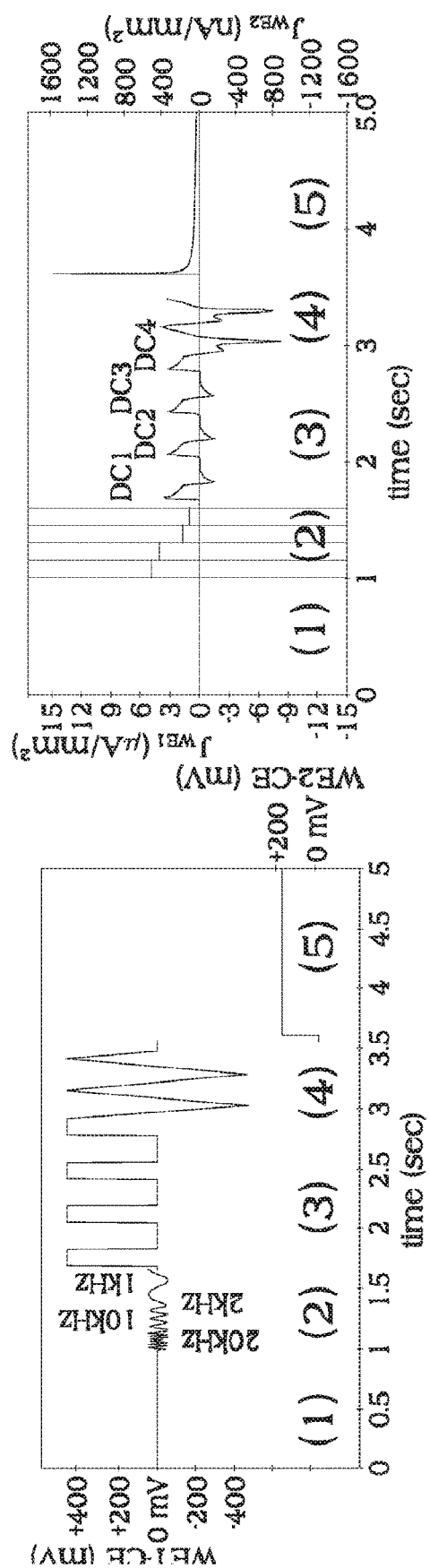

An alternative exemplary multi-analyte test sequence is shown in FIG. 4E (left panel), which includes not only the DC components as discussed above but also includes one or more AC components. For example, the test sequence includes (1) a delay after a sample is introduced to the test element to allow the reactions to proceed, during which an open circuit or near 0 V potential difference is maintained between both electrode pairs, (2) an AC block of a plurality of low-amplitude AC signals, (3) a first DC block of short-duration (e.g., about 50-500 msec) pulses ramped to or from about 0 V to about +450 mV over an interval of 10 msec, separated by similarly short-duration (e.g., about 50-500 msec) recovery pulses during which a closed circuit about 0 mV recovery potential is applied, (4) a second DC block having pulses that alternate or cycle between about −450 mV to about +450 mV in a closed circuit, and (5) a third DC block applying a fixed potential difference of about +175 mV following an open circuit between a second electrode pair dedicated to measuring a second analyte. FIG. 4E (right panel) shows an exemplary response to the test sequence shown in FIG. 4E (left panel).

In the multi-analyte test sequences, the AC component can be a series of small amplitude excitations at multiple discrete frequencies. Likewise, the first (pulsed) DC component can be a series of slew rate-controlled potential differences applied across a primary electrode pair between 0 V DC and an amplitude (i.e., +450 mV is this example) sufficient to produce a faradaic current response proportional to the primary analyte's concentration. The potential's amplitude is dependent on the primary analyte's mediator. The pulses' positive durations are long enough to minimize influences of charging currents and <150 msec to limit the diffusion distance above the primary analyte WE that is interrogated to 10-15 μm ($d=\sqrt{D_M \times t}$), ideally significantly less than the hydrated detection reagent's thickness. It is beneficial to measure the primary analyte's current responses near the end of one or more positive pulses to minimize the effects of charging transients and other noise. The 130 msec positive pulses are interspersed with intervals of 0 V applied potential difference of sufficient duration to allow the electrochemical cell to return to close to its initial state (1-0).

Moroever, the second DC component emulates a cyclic voltammetry technique. Here, the potential difference applied to primary electrode pair is swept between +450 mV and −450 mV at a rate of 3.5 V/sec. The second DC component therefor can be used to detect electro-active interferents. This is followed by a third DC component for measuring a secondary analyte concentration.

Similar to the first DC component, the third DC component applies one or more slew rate-controlled potential difference(s) across a secondary electrode pair at an amplitude (i.e., +175 mV is this example) sufficient to produce a faradaic current response proportional to the secondary analyte's concentration, and dependent on the secondary analyte's mediator. The secondary analyte's current is measured at a time after applying the secondary potential, typically about 500 msec.

Figure 4F:
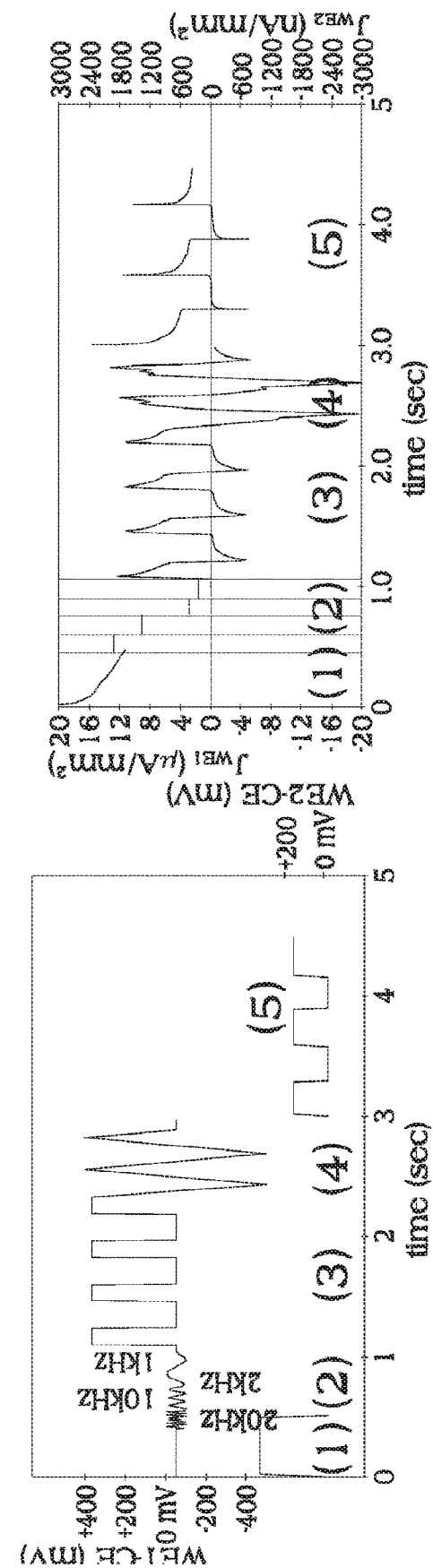

An alternative exemplary multi-analyte test sequence is shown in FIG. 4F, which includes not only the AC and DC components as discussed above but also a burn-off interval. For example, the test sequence includes (1) a burn-off interval during which a first positive potential difference is briefly applied between one or both electrode pairs to reduce the amount of reduced mediator present in the reagent(s) prior to a significant contribution from the analyte reaction of interest, (2) an AC block of a plurality of low-amplitude AC signals; (3) a first DC component of short-duration (e.g., about 50-500 msec) pulses ramped over an interval of 10 msec from about 0 V to a second positive potential difference sufficient to generate a measurable faradaic current related to the first analyte's concentration, then ramped back to about 0 V, separated by similarly short-duration (e.g., about 50-500 msec) recovery pulses during which a closed circuit about 0 mV recovery potential is applied, (4) a second DC component having pulses that alternate or cycle between about −450 mV to about +450 mV in a closed circuit, and (5) a third DC component of short-duration (e.g., about 50-500 msec) pulses ramped over an interval of 10 msec from about 0 V to a third positive potential difference sufficient to generate a measurable faradaic current related to the second analyte's concentration, then ramped back to about 0 V, separated by similarly short-duration (e.g., about 50-500 msec) recovery pulses during which a closed circuit about 0 mV recovery potential is applied. FIG. 4F (right panel) shows an exemplary response to the test sequence shown in FIG. 4F (left panel).

In view thereof, one of the test signals described herein can be applied to one or more of the WEs to provide a potential difference between the WE and CE. Alternatively, a test potential other than virtual ground or reference potential can be provided as a CE to provide a potential difference between the WE and CE. It shall be appreciated that the foregoing and a variety of other additional and alternate test cell, electrode, and/or circuitry configurations operable to apply a test signal to an electrode system in contact with a combined sample and detection reagent and measure a response thereto may be utilized.

AC and/or DC current response information is collected from the applied test sequence and includes current responses to the AC and DC blocks. Important information includes, but is not limited to, duration, shape and/or magnitude of the current response to an excitation pulse and/or a recovery pulse in the test sequence. In some instances, the current response information can be collected at an A/D sampling rate for DC and AC measurements to simplify the system design, including a single shared signal path for AC and DC measurements. Common digital audio sampling rates range include, but are not limited to, from about 44.1 kHz to about 192 kHz. A/D converters in this range are readily available from variety of commercial semiconductor suppliers.

Current response information to the AC block can be used to determine impedance, admittance and phase values or other complex parameters as described in further detail below. Likewise, current information to the DC blocks can be used to determine analyte concentrations or other complex parameters as described in further detail below (e.g., Hct-, temperature-, and/or interferent-based compensation and/or corrections, as well as compensations and/or corrections for reagent wetting, reagent film thickness, and reaction kinetics).

In the methods, the AC and/or DC response current information can be obtained (i.e., measured or recorded) at about 2,000/sec to about 200,000/sec, at about 3,000/sec to about 190,000/sec, at about 4,000/sec to about 180,000/sec, at about 5,000/sec to about 170,000, at about 6,000/sec to about 160,000/sec, at about 7,000/sec to about 150,000/sec, at about 8,000/sec to about 140,000/sec, at about 9,000/sec to about 130,000/sec, at about 10,000/sec to about 120,000/sec, at about 15,000/sec to about 110,000/sec, at about 20,000/sec to about 100,000/sec, at about 30,000/sec to about 90,000/sec, at about 40,000/sec to about 80,000/sec, at about 50,000/sec to about 70,000/sec, or at about 60,000/sec. In some instances, the AC and/or DC response current information can be obtained at about 100/sec to about 200/sec, at about 200/sec to about 300/sec, at about 300/sec to about 400/sec, at about 400/sec to about 500/sec, at about 500/sec to about 600/sec, at about 600/sec to about 700/sec, at about 700/sec to about 800/sec, at about 800/sec to about 900/sec, at about 1,000/sec to about 1,500/sec, at about 1,500/sec to about 2,000/sec, at about 2,000/sec to about 2,500/sec, at about 2,500/sec to about 3,000/sec, at about 3,000/sec to about 3,500/sec, at about 3,500/sec to about 4,000/sec, at about 4,000/sec to about 4,500/sec, at about 4,500/sec to about 5,000/sec, at about 5,000/sec to about 5,500/sec, at about 5,500/sec to about 6,000/sec, at about 6,000/sec to about 6,500/sec, at about 6,500 to about 7,000/sec, at about 7,000/sec to about 7,500/sec, at about 7,500/sec to about 8,000/sec, at about 8,000/sec to about 8,500/sec, at about 8,500 to about 9,000/sec, at about 9,000/sec to about 9,500/sec, at about 9,500/sec to about 10,000/sec, at about 10,000/sec to about 20,000/sec, at about 20,000/sec to about 30,000/sec, at about 30,000/sec to about 40,000/sec, at about 40,000/sec to about 50,000/sec, at about 50,000/sec to about 60,000/sec, at about 60,000/sec to about 70,000/sec, at about 70,000/sec to about 80,000/sec, at about 80,000/sec to about 90,000/sec, at about 90,000/sec to about 100,000/sec, at about 100,000/sec to about 110,000/sec, at about 110,000/sec to about 120,000/sec, at about 120,000/sec to about 130,000/sec, at about 130,000/sec to about 140,000/sec, at about 140,000/sec to about 150,000/sec, at about 150,000/sec to about 160,000/sec, at about 160,000/sec to about 170,000/sec, at about 170,000/sec to about 180,000/sec, at about 180,000/sec to about 190,000/sec, or at about 200,000/sec. In other instances, the AC and/or DC response current information can be obtained up to about 100/sec, about 200/sec, about 300/sec, about 400/sec, about 500/sec, 600/sec, about 700/sec, about 800/sec, about 900/sec, about 1,000/sec, about 1,250/sec, about 1,500/sec, about 1,750/sec, about 2,000/sec, about 2,225/sec, about 2,500/sec, about 2,750/sec, about 3,000/sec, about 3,250/sec, about 3,500/sec, about 3,750/sec, about 4,000/sec, about 4,250/sec, about 4,500/sec, about 4,750/sec, about 5,000/sec, about 5,250/sec, about 5,500/sec, about 5,750/sec, about 6,000/sec, about 6,250/sec, about 6,500, about 7,000/sec, about 7,250/sec, about 7,500/sec, about 7,750/sec, about 8,000/sec, about 8,250/sec, about 8,500/sec, about 8,750, about 9,000/sec, about 9,250/sec, about 9,500/sec, about 9,750/sec, about 10,000/sec, about 15,000/sec, about 20,000/sec, about 25,000/sec, about 30,000/sec, about 35,000/sec, about 40,000/sec, about 45,000/sec, about 50,000/sec, about 55,000/sec, about 60,000/sec, about 65,000/sec, about 70,000/sec, about 75,000/sec, about 80,000/sec, about 85,000/sec, about 90,000/sec, about 95,000/sec, about 100,000/sec, about 105,000/sec, about 110,000/sec, about 115,000/sec, about 120,000/sec, about 125,000/sec, about 130,000/sec, about 135,000/sec, about 140,000/sec, about 145,000/sec, about 150,000/sec, about 155,000/sec, about 160,000/sec, about 165,000/sec, about 170,000/sec, about 175,000/sec, about 180,000/sec, about 185,000/sec, about 190,000/sec, about 195,000 or at about 200,000/sec. In yet other instances, the AC and/or DC response current information can be obtained at more than 200,000/sec.

Additional details regarding exemplary electrochemical measurement methods are disclosed in, for example, U.S. Pat. Nos. 4,008,448; 4,225,410; 4,233,029; 4,323,536; 4,891,319; 4,919,770; 4,963,814; 4,999,582; 4,999,632; 5,053,199; 5,108,564; 5,120,420; 5,122,244; 5,128,015; 5,243,516; 5,288,636; 5,352,351; 5,366,609; 5,385,846; 5,405,511; 5,413,690; 5,437,999; 5,438,271; 5,508,171; 5,526,111; 5,627,075; 5,628,890; 5,682,884; 5,727,548; 5,762,770; 5,858,691; 5,997,817; 6,004,441; 6,054,039; 6,254,736; 6,270,637; 6,645,368; 6,662,439; 7,073,246; 7,018,843; 7,018,848; 7,045,054; 7,115,362; 7,276,146; 7,276,147; 7,335,286; 7,338,639; 7,386,937; 7,390,667; 7,407,811; 7,429,865; 7,452,457; 7,488,601; 7,494,816; 7,545,148; 7,556,723; 7,569,126; 7,597,793; 7,638,033; 7,731,835; 7,751,864; 7,977,112; 7,981,363; 8,148,164; 8,298,828; 8,329,026; 8,377,707; and 8,420,404, as well as RE36268, RE42560, RE42924 and RE42953. Other exemplary electrochemical measurement methods that can be used herein are disclosed in Int'l Patent Application Publication Nos. WO 2014/140718; WO 2014/140164; WO 2014/140170; WO 2014/140172; WO 2014/140173; and WO 2014/140177.

The analyte concentrations can be determined by algorithms and/or correlations to the amount of redox equivalents (e.g., electrons) liberated or consumed in the detection reagents and measured via the electrode system, where such algorithms and/or correlations are known in the art.

After the response information is processed and correlated to determine the analyte concentrations, the methods can include displaying on the meter one or more analyte concentrations or trends to a user. A variety of graphical and/or numeric means are known in the art for displaying the data and other related information to the user. See, e.g., US Patent Application Publication No. 2009/0210249 and U.S. Pat. No. 9,218,453.

Aside from the steps described above, the methods also can include additional steps. With respect to measuring glucose and ketones, the methods can include determining both analytes during each test but only providing to the user the glucose concentration unless a predetermined threshold or condition for one analyte (e.g., glucose), the other analyte (e.g., ketone), or both analytes is met. For example, hydroxybutyrate concentrations below 0.6 mM in blood are considered normal, while hydroxybutyrate concentrations that are between 0.6 mM and 1.5 mM indicate that a problem may develop and that are greater than 1.5 mM indicate a risk for developing DKA. Hydroxybutyrate concentrations above 3 mM in blood are indicative or DKA and require emergency medical treatment. Thus, and in some instances, the glucose concentration is displayed to the user and the ketone concentration is displayed only of the predetermined threshold(s) or condition(s) is/are met, and where the predetermined threshold(s) or condition(s) can be a glucose concentration of about 240 mg/dL or a ketone concentration from about 0.6 mM to about 3.0 mM or even from about 0.6 mM to about 1.5 mM. See, e.g., Int'l Patent Application No. 2014/068024.

In other instances, the methods also can include providing the indication in response to determining the first analyte concentration is above a predetermined value includes at least one of displaying the first analyte concentration, providing a warning, providing a list of actions to take in response to the first analyte concentration being above the predetermined value, and transmitting a message to at least one of a user of the test element, healthcare provider, caregiver and parent or guardian.

Specifically, providing the indication in response to determining the first analyte concentration is above the predetermined level can include transmitting a message to a mobile device or computer. In some instances, providing the indication in response to determining the first analyte concentration is above the predetermined level further includes displaying a message related to the first analyte concentration on a test meter. In other instances, providing the indication in response to determining the first analyte concentration is above the predetermined level includes displaying a message related to the first analyte concentration. In still other instances, providing the indication in response to determining the first analyte concentration is above the predetermined level includes changing a color or a shading of at least a portion of a display screen or textual display. In still another form, providing the indication in response to determining the first analyte concentration is above the predetermined level includes displaying an information icon on a display screen. In still another form, providing the indication in response to determining the first analyte concentration is above the predetermined level includes displaying an information icon on a display screen with an audio tone or vibration to encourage the patient to take notice. In one aspect of this form, the method further includes providing a message in response to a selection of the information icon. In a further aspect, the message includes at least one of a description of the first analyte concentration, a list of actions to take in response to the first analyte concentration being above the predetermined level, and contact information of a healthcare provider.

Accordingly, a ketone watch may be set by the meter whenever a measured glucose value greater than or equal to a predetermined value, such as 240 mg/dL, is recorded. Alternatively, the ketone watch may be set by the meter whenever a measured ketone value is greater than or equal to a predetermined value, such as 0.6 mM to 3.0 mM. The ketone watch would recommend testing glucose and ketone every 4-6 hours as long as the predetermined value remains. In one non-limiting form for example, upon initiation of and during the ketone watch, the meter may automatically display measured glucose and ketone levels regardless of their relationship with any pre-specified values. A ketone watch may also start a new trending set of data to determine if ketones are beginning to rise even if still below the threshold of a high ketone level. A ketone watch may also be started if the user has indicated they have an illness such as a cold or the flu.

EXAMPLES

The inventive concept will be more fully understood upon consideration of the following non-limiting examples, which are offered for purposes of illustration, not limitation.

Example 1: Ketone and Glucose Detection Reagents for Dual Analyte Analysis

Methods:

Ketone and glucose detection reagents were prepared as described below. Table 3 shows the basic components for the ketone detection reagent.

TABLE 3

| Ketone Detection Reagent. | | | |
|---|---|---|---|
| Reagent Component | Wet (%) | Dry (%) | Wet (mM) |
| MOPS | 1.51 | 14.49 | 72.22 |
| Keltrol | 0.08 | 0.78 | |
| Natrosol 250 HBR | 0.56 | 5.34 | |
| Kollidon VA 64 | 1.63 | 15.64 | |
| Tergitol 15-S-19 | 0.03 | 0.28 | |
| Propiofan 70D | 1.18 | 11.29 | |
| PG355 | 0.33 | 3.14 | 10.12 |
| cNAD | 2.00 | 19.20 | 30.37 |
| HBDH | 2.56 | 24.54 | |
| KOH | 0.55 | 5.29 | |
| % solids | 10.43 | 100.00 | |

Table 4 shows the basic components for the glucose detection reagent.

TABLE 4

| Glucose Detection Reagent. | | | |
|---|---|---|---|
| Reagent Component | Wet (%) | Dry (%) | Wet (mM) |
| PIPES Acid | 2.19 | 22.58 | 72.5 |
| Xanthan Gum/Keltrol F | 0.09 | 0.96 | |
| Natrosol 250 HBR | 0.51 | 5.28 | |
| Geropon T77 | 0.03 | 0.29 | |
| Kollidon VA 64 | 1.73 | 17.81 | |
| NA1144 | 0.64 | 6.64 | 23.3 |
| sodium succinate hexahydrate | 0.23 | 2.33 | 14.0 |
| KOH 30%(w/v) | 0.91 | 9.34 | |
| FAD-GDH | 2.07 | 21.34 | |
| Propiofan 70D | 1.30 | 13.43 | |
| % Solid Content | 9.71 | 100 | |

3-HB was prepared in 150 mM phosphate buffer, pH 7.

A test sequence was applied to different levels of 3-HB in buffer (i.e., 0, 0.5, 1.0, 1.5, 2.0, 3.0, 4.0 and 8.0 mM). A test sequence as disclosed in Int'l Patent Application Publication No. WO 2014/140178 was used, which was then followed by a single, long pulse of 175 mV (vs. glucose counter electrode). Current was read at 0.5 seconds after applying the 175 mV potential difference between the ketone working electrode and glucose counter electrode for ketone measurements.

The ketone reagent had a high mediator content (10 mM) when compared to other studies herein. The polymer content in the dry film was higher than in other studies.

Figure 5:
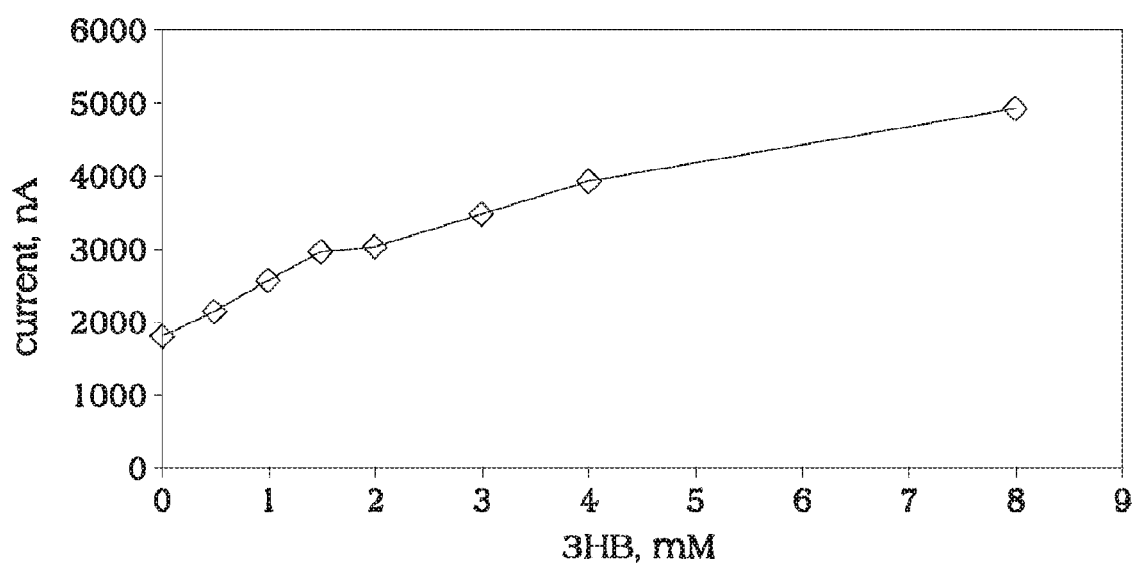
FIG. 5 shows a dose-response curve for an exemplary ketone detection reagent having a mutant HBDH, a high mediator content (PG355) and a high polymer content (Natrasol). Eight different levels of 3-hydroxybutyrate (3-HB) (0 mM, 0.5 mM, 1 mM, 1.5 mM, 2 mM, 3 mM, 4 mM, and 8 mM) were tested.

Results:

FIG. 5 shows a linear response during the dose response study, where increasing currents were measured as the 3-HB concentration increased.

Example 2: Aqueous Cross-Talk Study

Methods:

Ketone and glucose detection reagents were prepared as above in Example 1. The detection reagents were incorporated into test elements and then used in cross-talk experiments. The glucose detection reagent was applied to the glucose working and counter electrodes, and the ketone detection reagent was applied to the ketone working electrode.

The aqueous matrix for glucose and 3-HB was 150 mM phosphate buffer, pH 7. In the cross-talk experiments, test elements were dosed with aqueous samples that contained both 3-HB and glucose with varying concentrations (0, 1.0, 3.0 and 8.0 mM for 3-HB; and 0 or 300 mg/dL for glucose). Current was read at about 130 msec (see, e.g., point "DC1" in FIG. 4E, right panel) after initiating the first ramped pulse from about 0 mV to about +450 mV between the glucose working electrode and the glucose counter electrode for glucose measurements and at about 0.5 seconds after applying the 175 mV potential difference between the ketone working electrode and glucose counter electrode for ketone measurements.

Figure 6A:
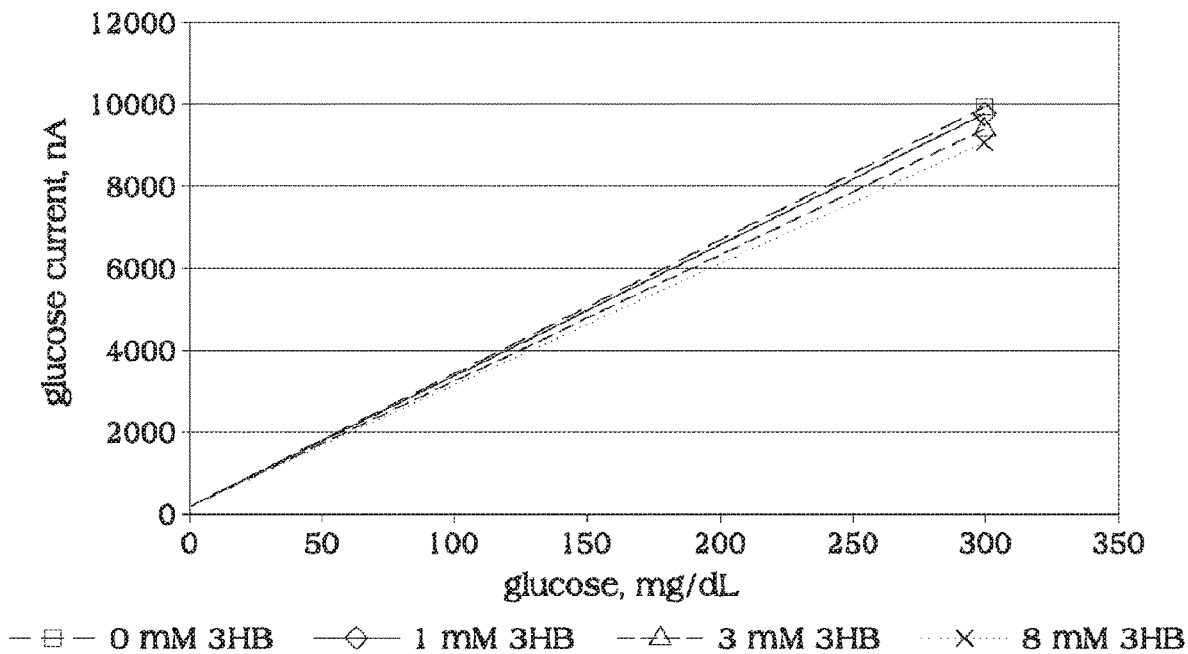
FIGS. 6A-B show results of cross-talk experiments in which test elements were dosed with samples containing both 3-HB and glucose with varying concentrations. Specifically.

Results:

FIG. 6A shows the glucose current in the presence of 3-HB, with no impact on the glucose current from the presence of different levels of 3-HB (0 mM, 1 mM, 3 mM, and 8 mM). Two glucose levels were tested, each with different levels of 3-HB.

Figure 6B:
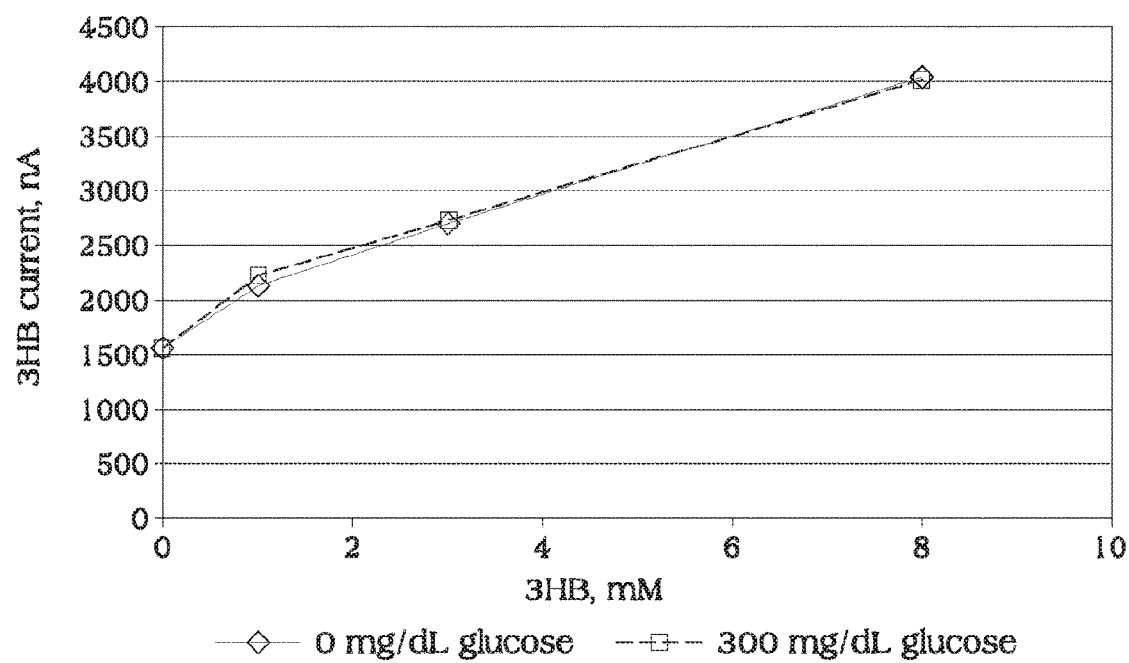

Likewise, FIG. 6B shows the 3-HB current in the presence of glucose, with no impact on the 3-HB current from the presence of different levels of glucose (0 mg/dL and 300 mg/dL). Four different levels of 3-HB (0 mM, 1 mM, 3 mM, and 8 mM) were tested, with each level containing either 0 mg/dL or 300 mg/dL of glucose.

Example 3: Effect of Different Coenzymes on the Ketone Detection Reaqent

Methods:

Reagent chemistries were prepared as described above in Example 1. Here, however, a ketone detection reagent was prepared with NAD instead of cNAD for the coenzyme/cofactor. Tables 5 and 6 show the basic components for the alternate ketone detection reagents. In the dose response studies, the glucose reagent the same as in the Examples above.

TABLE 5

Alternate Ketone Detection Reagent (with NAD).

| Reagent Component | Wet (%) | Dry (%) | Wet (mM) |
|---|---|---|---|
| MOPS | 2.12 | 14.67 | 101.5 |
| Keltrol | 0.075 | 0.52 | |
| Natrosol 250 HBR | 0.27 | 1.89 | |
| Kollidon VA 64 | 1.39 | 9.58 | |
| Tergitol 15-S-19 | 0.03 | 0.21 | |
| Propiofan 70D | 1.20 | 8.28 | |
| sodium succinate | 0.41 | 2.82 | 15.1 |
| PG355 | 0.242 | 1.67 | 7.5 |
| NAD | 4.11 | 28.4 | 62.0 |
| HBDH | 3.794 | 26.20 | |
| KOH | 0.837 | 5.78 | |
| % solids | 14.483 | 100.00 | |

TABLE 6

Alternate Ketone Detection Reagent (with cNAD).

| Reagent Component | Wet (%) | Dry (%) | Wet (mM) |
|---|---|---|---|
| MOPS | 2.12 | 14.67 | 101.5 |
| Keltrol | 0.075 | 0.52 | |
| Natrosol 250 HBR | 0.27 | 1.89 | |
| Kollidon VA 64 | 1.39 | 9.58 | |
| Tergitol 15-S-19 | 0.03 | 0.21 | |
| Propiofan 70D | 1.20 | 8.28 | |
| sodium succinate | 0.41 | 2.82 | 15.1 |
| PG355 | 0.242 | 1.67 | 7.5 |
| cNAD | 4.09 | 28.21 | 62.0 |
| HBDH | 3.79 | 26.20 | |
| KOH | 0.837 | 5.78 | |
| % solids | 14.46 | 100.00 | |

The test sequence was the same as in the Examples above and was applied to different levels of 3-HB in buffer (i.e., 0, 0.5, 1.0, 1.5, 2.0, 3.0, and 4.0 mM) and to different levels of glucose in buffer (i.e., 0, 57, 123, 520, and 1000 mg/dL). As above in Example 2, current was read at about 130 msec (see, e.g., point "DC1") after initiating the first ramped pulse from about 0 mV to about +450 mV between the glucose working electrode and the glucose counter electrode for glucose measurements and at about 0.5 seconds after applying the 175 mV potential difference between the ketone working electrode and glucose counter electrode for ketone measurements.

The ketone reagent has low mediator content (7.5 mM) when compared to the studies above. Likewise, the polymer content in the dry film is lower than the studies above.

Figure 7A:
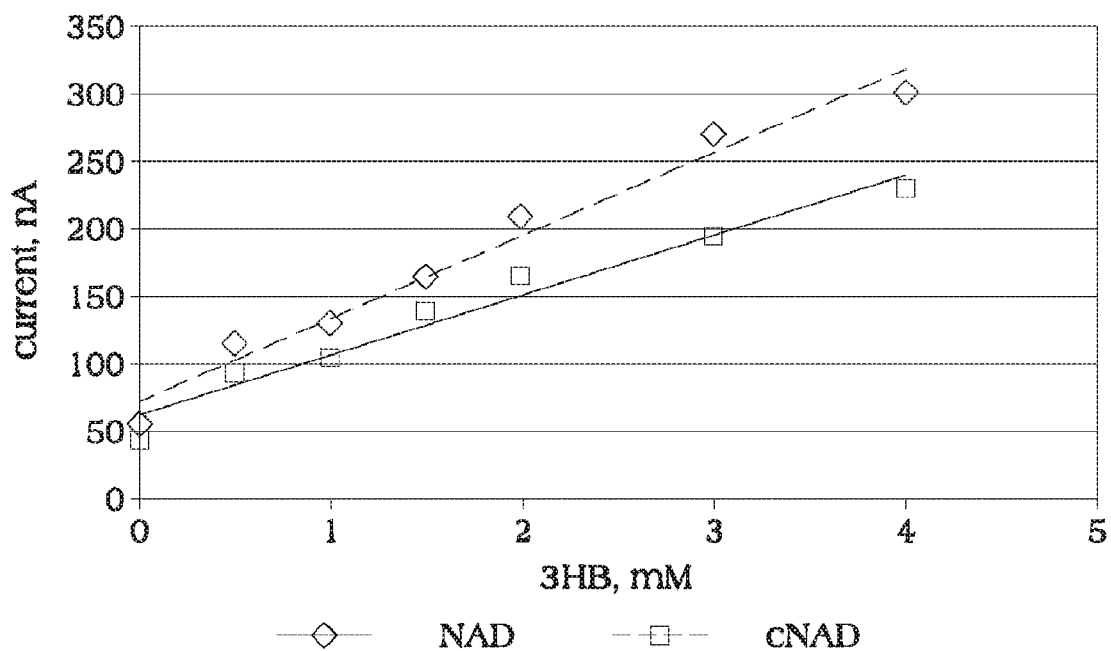
FIGS. 7A-B show dose-response curves for another exemplary ketone detection reagent having a mutant HBDH, a low mediator content (PG355), low polymer content, and a high cofactor content (NAD or cNAD). Specifically.

Results:

FIG. 7A shows that NAD (diamonds) is slightly more effective as the cofactor than cNAD (squares); however, the response with cNAD is still acceptable, especially since it possesses an enhanced stability over the native cofactor NAD.

Figure 7B:
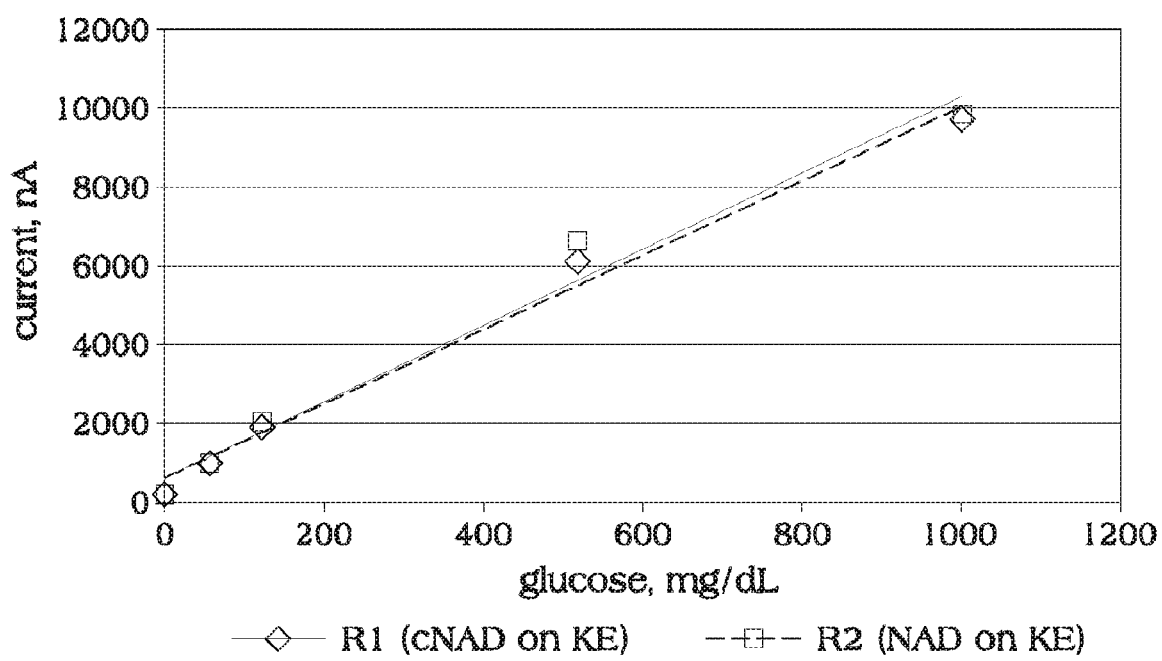

FIG. 7B shows that there is little difference on the glucose measurement when NAD or cNAD are used in the ketone detection reagent. Thus, FIG. 7B shows that the glucose response is unperturbed by the detection reagent deposition method (e.g., PicoJet®).

Example 4: Effect of Different Mediators on the Ketone Detection Reaqent

Methods:

Reagent chemistries were prepared as described above in Example 1. Here, however, the ketone detection reagent was prepared with cPES instead of PG355. Table 7 shows the basic components for the alternate ketone detection reagent. In the dose response studies, the glucose reagent the same as in the Examples above.

TABLE 7

Alternate Ketone Detection Reagent (with cPES).

| Reagent Component | Wet (%) | Dry (%) | Wet (mM) |
|---|---|---|---|
| MOPS | 2.13 | 14.85 | 102.0 |
| Keltrol | 0.08 | 0.53 | |
| Natrosol 250 HBR | 0.27 | 1.91 | |
| Kollidon VA 64 | 1.39 | 9.69 | |
| Tergitol 15-S-19 | 0.03 | 0.21 | |
| Propiofan 70D | 1.20 | 8.36 | |
| sodium succinate | 0.41 | 2.86 | 15.2 |
| cPES | 0.23 | 1.63 | 7.5 |
| cNAD | 4.10 | 28.55 | 62.2 |
| HBDH | 3.89 | 26.51 | |
| KOH | 0.70 | 4.90 | |
| % solids | 14.37 | 100.00 | |

The test sequence was the same as in the Examples above and was applied to different levels of 3-HB in buffer (i.e., 0, 0.5, 1.0, 1.5, 2.0, 3.0, and 4.0 mM). As above, current was read at 0.5 seconds after applying the 175 mV potential difference between the ketone working electrode and glucose counter electrode for ketone measurements.

The ketone reagent has low mediator content (7.5 mM) when compared to the studies above. Likewise, the polymer content in the dry film is lower than the studies above.

Figure 8:
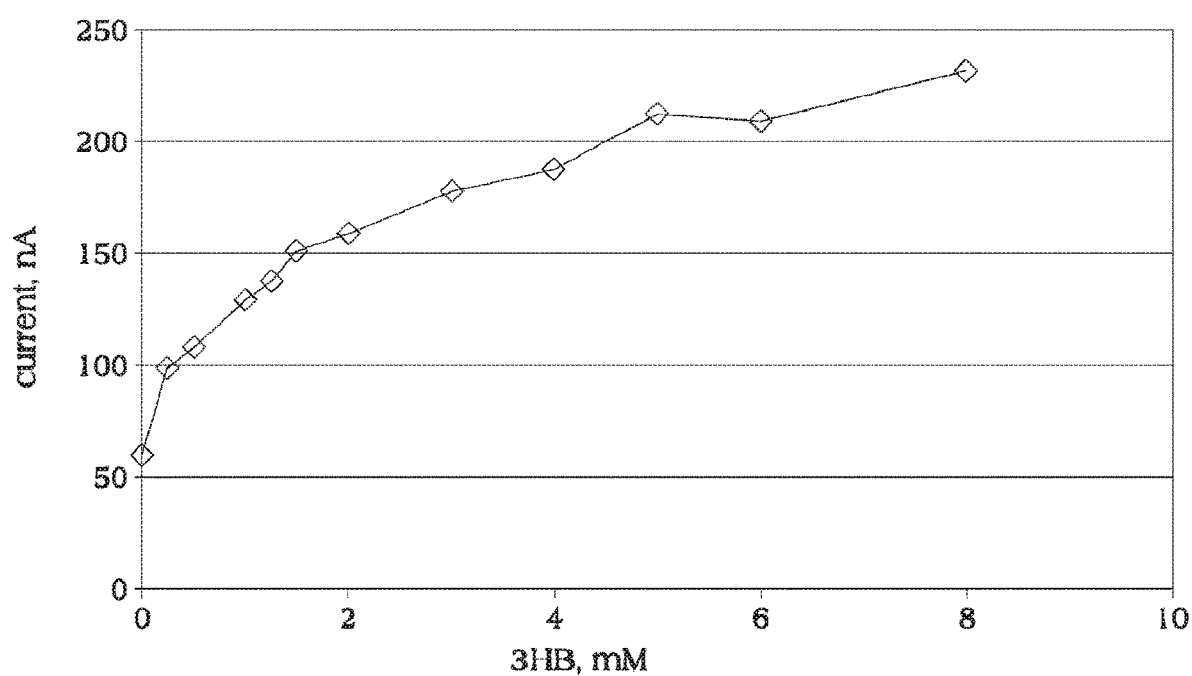
FIG. 8 shows a dose-response curve for multi-analyte test elements having not only a glucose detection reagent but also having an exemplary ketone detection reagent that includes a different mediator (cPES) than the ketone detection reagents above. The test elements were dosed with samples containing 3-HB with varying concentrations (0 mM, 0.25 mM, 0.5 mM, 1 mM, 1.25 mM, 1.5 mM, 2 mM, 3 mM, 4 mM, 5 mM, 6 mM, and 8.0 mM).

Results:

FIG. 8 shows that cPES is an effective mediator with comparable results to using PG355.

Example 5: Effect of Different Enzymes on the Ketone Detection Reagent

Methods:

Reagent chemistries were prepared as described above in Example 2. Here, however, the ketone detection reagent was prepared with wild-type HBDH, an AFDH3 HBDH, and an AFDH4 HBDH mutant (see, EP Patent Application No. 16165421.5 for additional details on the mutants). Table 8 shows the basic components for the alternate ketone detection reagents. In the dose response studies, the glucose detection reagent was the same as in the Examples 1 and 2 above.

TABLE 8

Alternate Ketone Detection Reagent (with wild-type HBDH).

| Reagent Component | Wet (%) | Dry (%) | Wet (mM) |
|---|---|---|---|
| MOPS | 2.12 | 14.54 | 101.5 |
| Keltrol | 0.08 | 0.52 | |
| Natrosol 250 HBR | 0.27 | 1.87 | |
| Kollidon VA 64 | 1.39 | 9.50 | |
| Tergitol 15-S-19 | 0.03 | 0.21 | |
| Propiofan 70D | 1.20 | 8.21 | |
| sodium succinate | 0.41 | 2.80 | 15.1 |
| PG355 | 0.24 | 1.66 | 7.5 |
| cNAD | 4.08 | 27.97 | 61.9 |
| HBDH, AFDH3 HBDH, or AFDH4 HBDH | 3.80 | 26.00 | |
| KOH | 0.98 | 6.71 | |
| % solids | 14.6 | 100.00 | |

The test sequence was the same as in the Examples above and was applied to samples having different levels of 3-HB in buffer (i.e., 0.5, 1.5, and 3.0 mM) and to different levels of glucose in buffer (i.e., 40, 150, and 400 mm/dL). Additionally, the samples were prepared as glycolyzed venous blood having a hematocrit of about 41%. As above in Examples 2-3, current was read at about 130 msec (see, e.g., point "DC1") after initiating the first ramped pulse from about 0 mV to about +450 mV between the glucose working electrode and the glucose counter electrode for glucose measurements and at about 0.5 seconds after applying the 175 mV potential difference between the ketone working electrode and glucose counter electrode for ketone measurements.

Figure 9A:
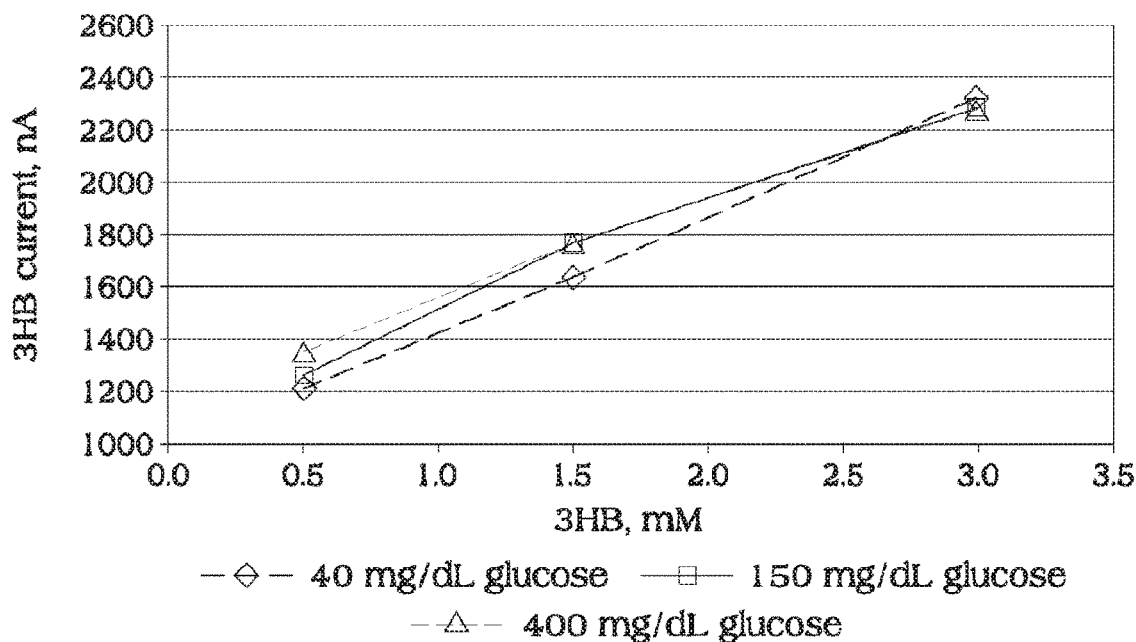
FIGS. 9A-9F show the effect of different HBDH enzymes in an exemplary ketone detection reagent. Specifically.
Figure 9B:
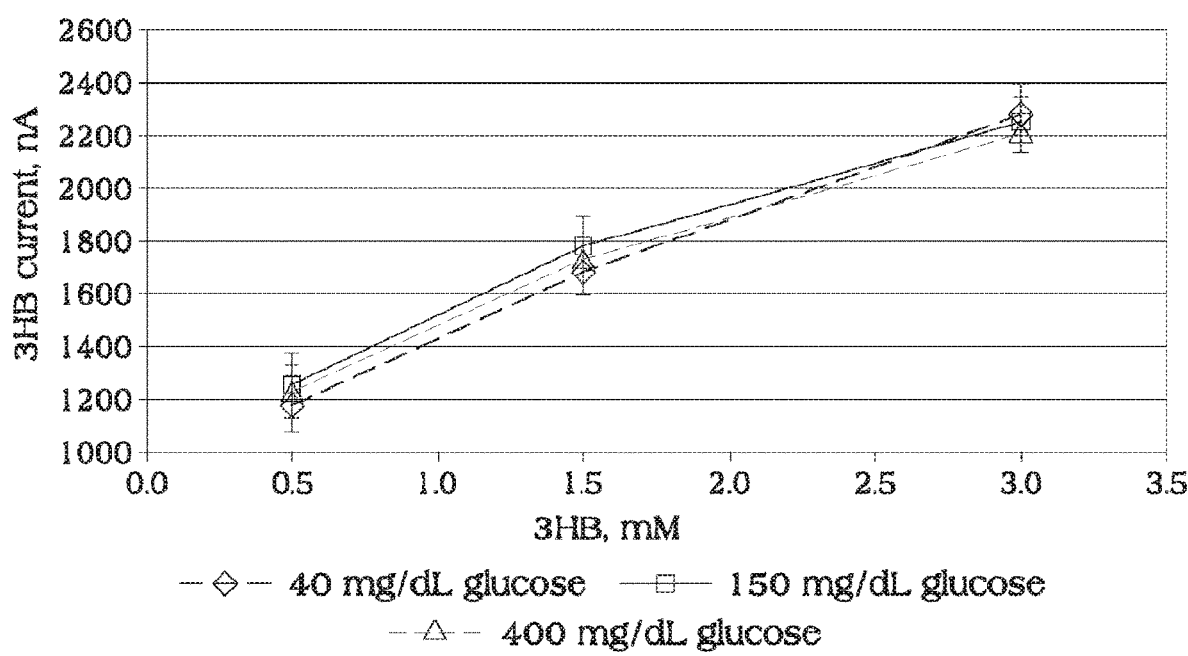
Figure 9C:
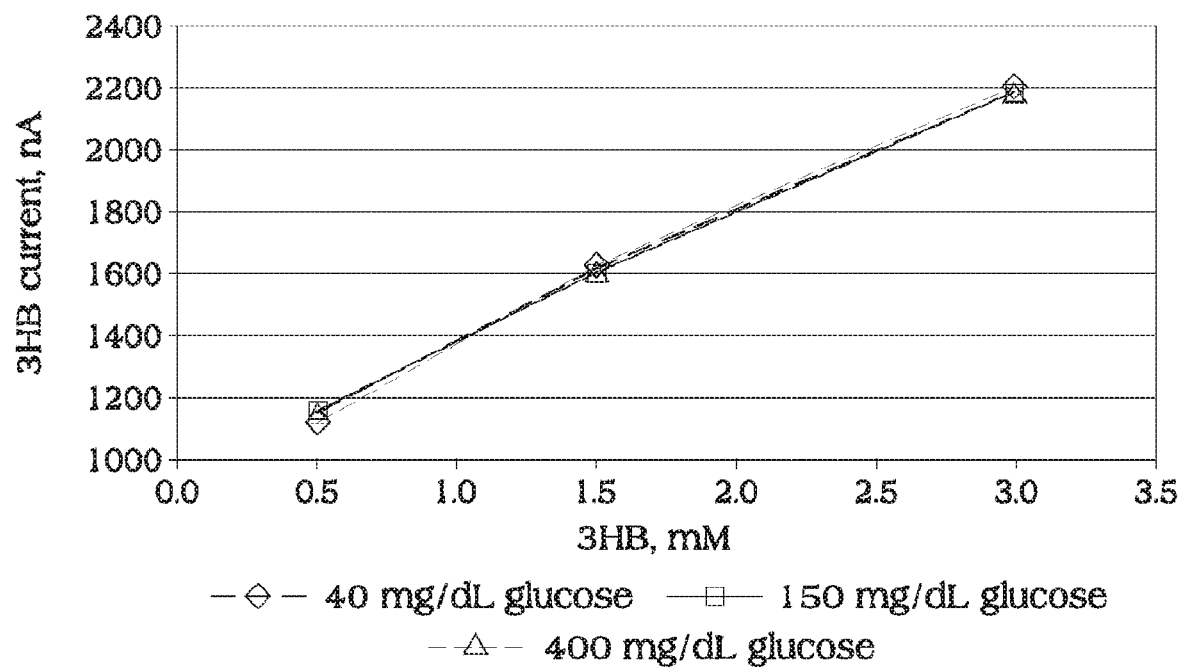
Figure 9D:
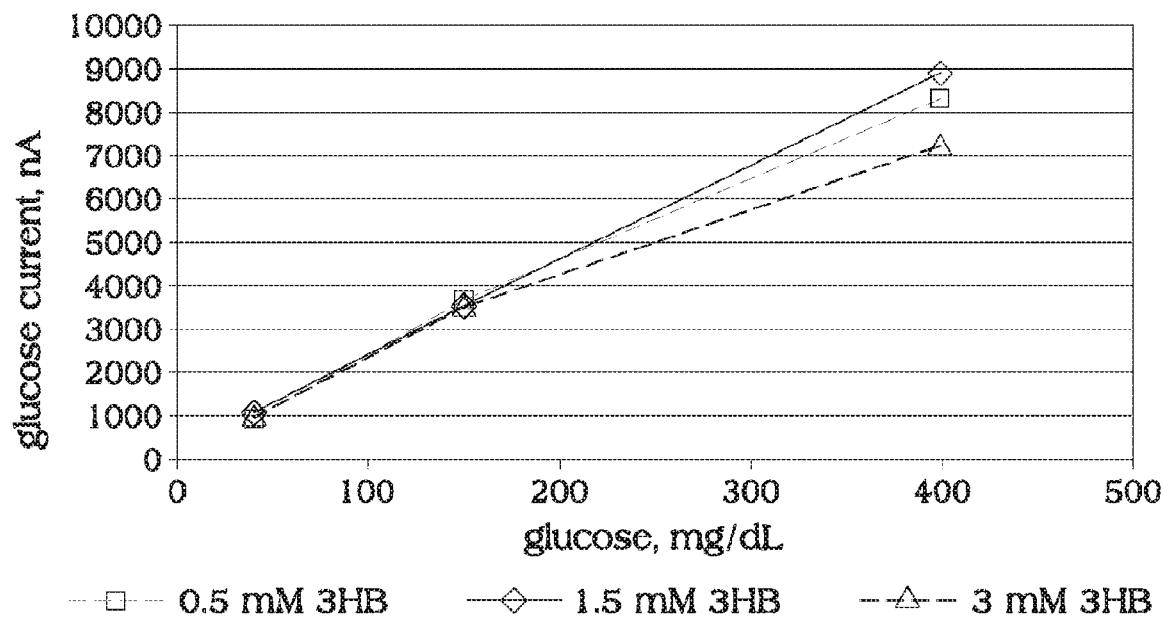
Figure 9E:
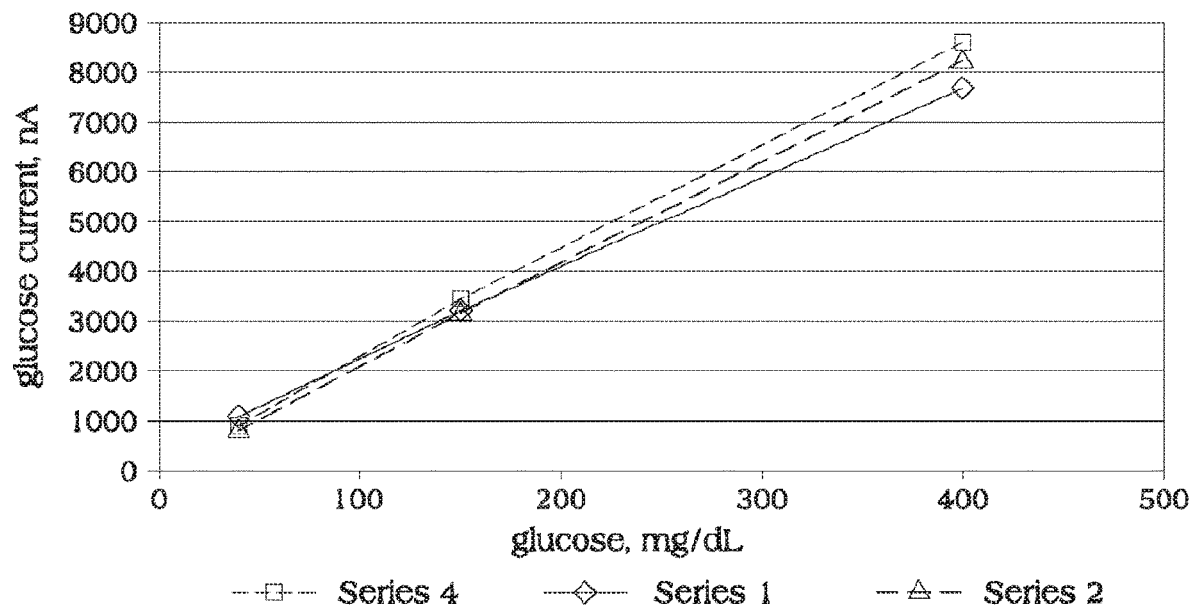
Figure 9F:
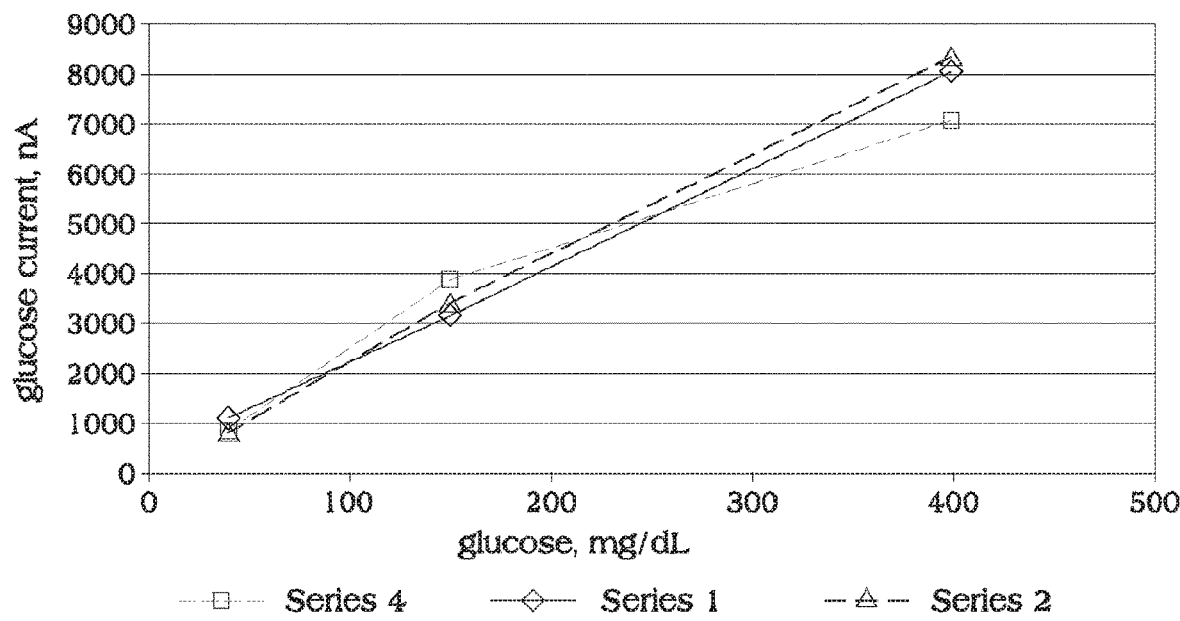

Results:

Overall, no significant impact on 3-HB signal (i.e., current) in the presence of glucose was observed among the different HBDH enzymes (see, FIGS. 9A-C). Likewise, no significant impact on glucose signal in the presence of 3-HB was observed (see, FIGS. 9D-F). Thus, there is no evidence of cross-talk between reagents.

Example 6: Alternative Ketone and Glucose Detection Reagents for Dual Analyte Analysis Methods:

Reagent chemistries were prepared as described above in Example 2. Here, however, the glucose detection reagent was prepared with FAD-GDH and NA1144 and the ketone detection reagent was prepared with HBDH and diaphorase/NA1144. The NA1144 concentration for the glucose detection reagent was 25 mM and was 7.5 mM for the ketone detection reagent.

Ketone and glucose detection reagents were deposited using PicoJet® discrete dispensing.

The test sequence was the same as in the Examples above and was applied to samples having different levels of 3-HB in buffer (i.e., 0 mM, 1 mM, 3 mM, and 8 mM) and having a single glucose level (i.e., 300 mm/dL).

Figure 10A:
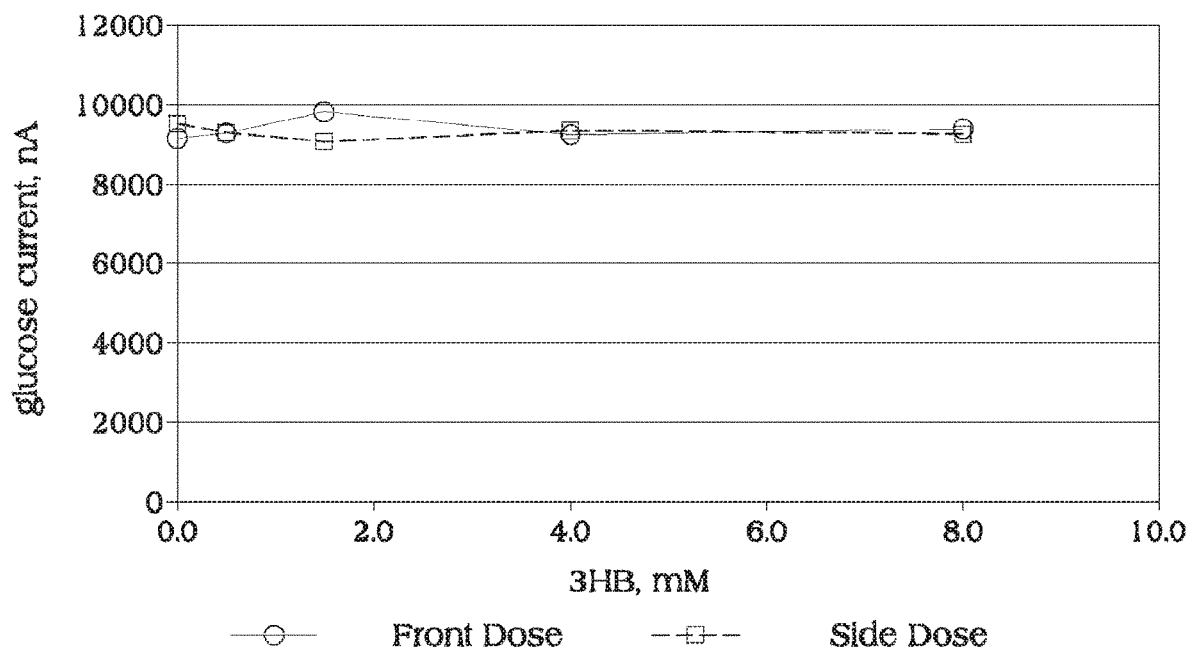
FIGS. 10A-B show results of cross-talk experiments for an alternative exemplary dual detection reagent in which test elements were dosed either form the top of the side with samples containing glucose (300 mg/dL) and 3-HB. Specifically.
Figure 10B:
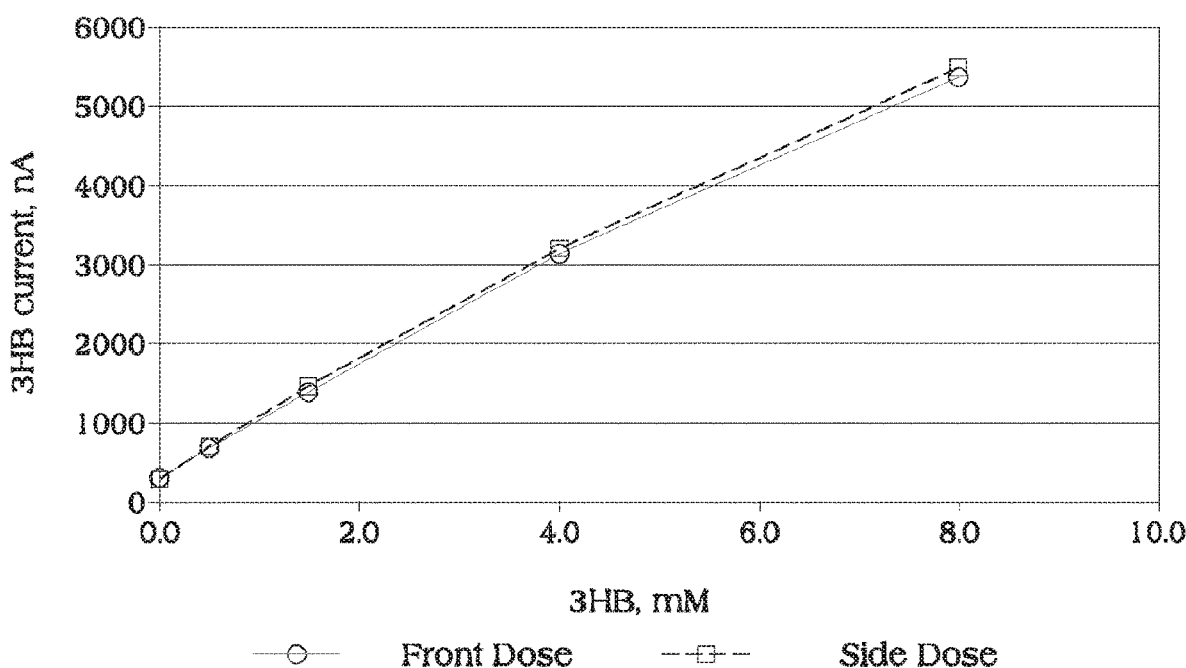

Results:

As shown in FIG. 10A, No significant impact on the glucose current (glucose concentration=300 mg/dL) was observed when the test solutions contained different levels of 3-HB (0, 0.5, 1.5, 4, and 8 mM) and strips were dosed from either the front or the side. Likewise, and as shown in FIG. 10B, there was no significant impact on the 3-HB signal (i.e., current) when test strips were dosed from either the front or the side of the strip. When the strips were dosed from the side, the test solution flowed over the glucose reagent first. If the glucose reagent was not firmly fixed in place, resulting in cross-talk between the reagents, one would expect to see some impact on the 3HB current measured at the ketone working electrode.

Example 7: Slot-Die Coating Dual Glucose Detection Reagents onto Test Elements Methods:

Reagent chemistries were prepared as described above in Example 1. Likewise, the test sequence is the same as described above in Example 1.

Ketone and glucose detection reagents were deposited using dual reagent slot-die coating instead of PicoJet® discrete dispensing.

For the cross-talk experiments, test elements were dosed with samples having different levels of 3-HB in buffer (i.e., 0.5, 1.5, and 3.0 mM) and to different levels of glucose in buffer (i.e., 1, 150, and 300 mm/dL). Again, and as above in Example 2, current was read at about 130 msec (see, e.g., point "DC1") after initiating the first ramped pulse from about 0 mV to about +450 mV between the glucose working electrode and the glucose counter electrode for glucose measurements and at about 0.5 seconds after applying the 175 mV potential difference between the ketone working electrode and glucose counter electrode for ketone measurements.

Figure 11A:
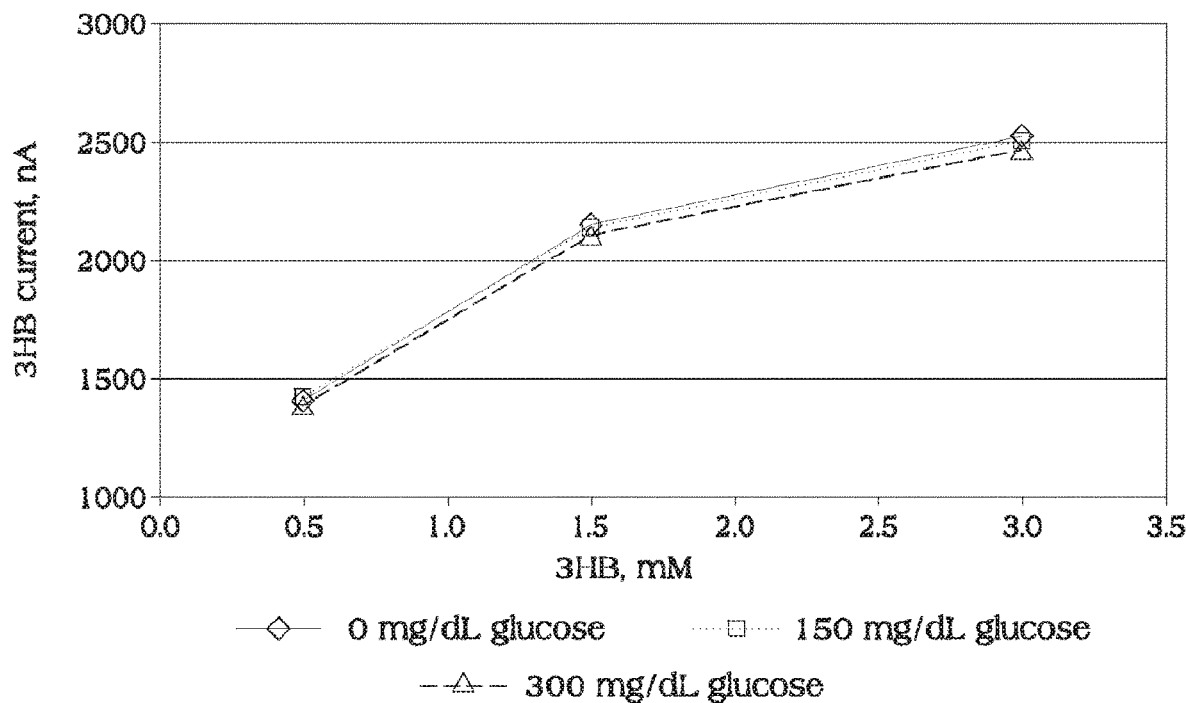
FIGS. 11A-B show results of cross-talk experiments in which the ketone and glucose detection reagents were deposited via slot-die coating instead of PicoJet® discrete dispensing, which were dosed with samples containing both 3-HB and glucose with varying concentrations. Specifically.
Figure 11B:
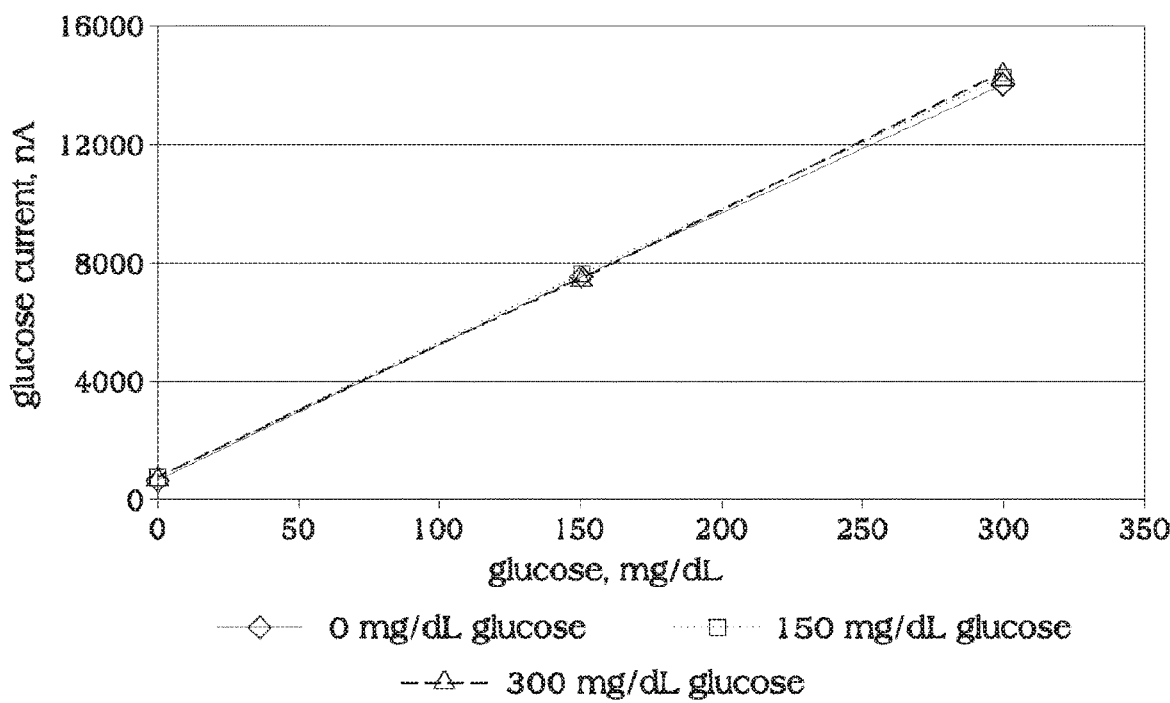

Results:

Overall, no significant impact was observed on 3-HB signal in the presence of different levels of glucose was observed (see, FIG. 11A). Likewise, no significant impact was observed on glucose signal in the presence of 3-HB was observed (see, FIG. 11B). Thus, there was no evidence of cross-talk between reagents via slot die coating.

Example 8: Inkjet Printing Dual Detection Reagents with Polymer Overcoat onto Test Elements Methods:

Reagent chemistries were prepared as described above in Example 1. Here, two glucose detection reagents were prepared, where one glucose detection reagent included FAD-GDH and the other glucose detection reagent included a mutant PQQ-GDH with low maltose sensitivity (available from Roche Diagnostics, Inc.; Indianapolis, Ind. USA). The inkjet formulations for each glucose detection reagent were the same with the exception of the enzyme and coenzyme.

TABLE 9

Inkjet Formations.

| Reagent Component | Wet (%) | Dry (%) |
|---|---|---|
| PIPES | 3.7 | 21.9 |
| Kollidon VA 64 | 7.9 | 47.6 |
| sodium succinate | 0.3 | 1.7 |
| KOH | 0.7 | 4.1 |
| Tegowet 265 | 0.05 | 0.3 |
| NA1144 | 1.4 | 8.4 |
| enzyme (incl. coenzyme) | 3.0 | 16.0 |

TABLE 10

Polymer Overcoat Formulation.

| Component | Wet (%) | Dry (%) |
|---|---|---|
| PIPES | 3.4 | 15.6 |
| Kollidon VA 64 | 11.9 | 54.0 |
| Natrosol 250 HBR | 1.2 | 5.6 |
| Propiofan 70D | 2.7 | 12.4 |
| Aerosil | 2.7 | 12.4 |

Both glucose detection reagents were deposited using inkjet printing instead of dual reagent slot-die coating or PicoJet® discrete dispensing.

The test sequence is the same as described above in Example 1. Minimal crosstalk between the electrodes was observed for major sugar interferents for each electrode. The current responses were normalized to the glucose response for each electrode, since the WE areas were different for each reagent. No dose response data was collected; instead, the experiment was to apply 450 mV across each WE and CE and run a "kinetic" experiment, where the current was monitored from the time the sample was applied.

Figure 12A:
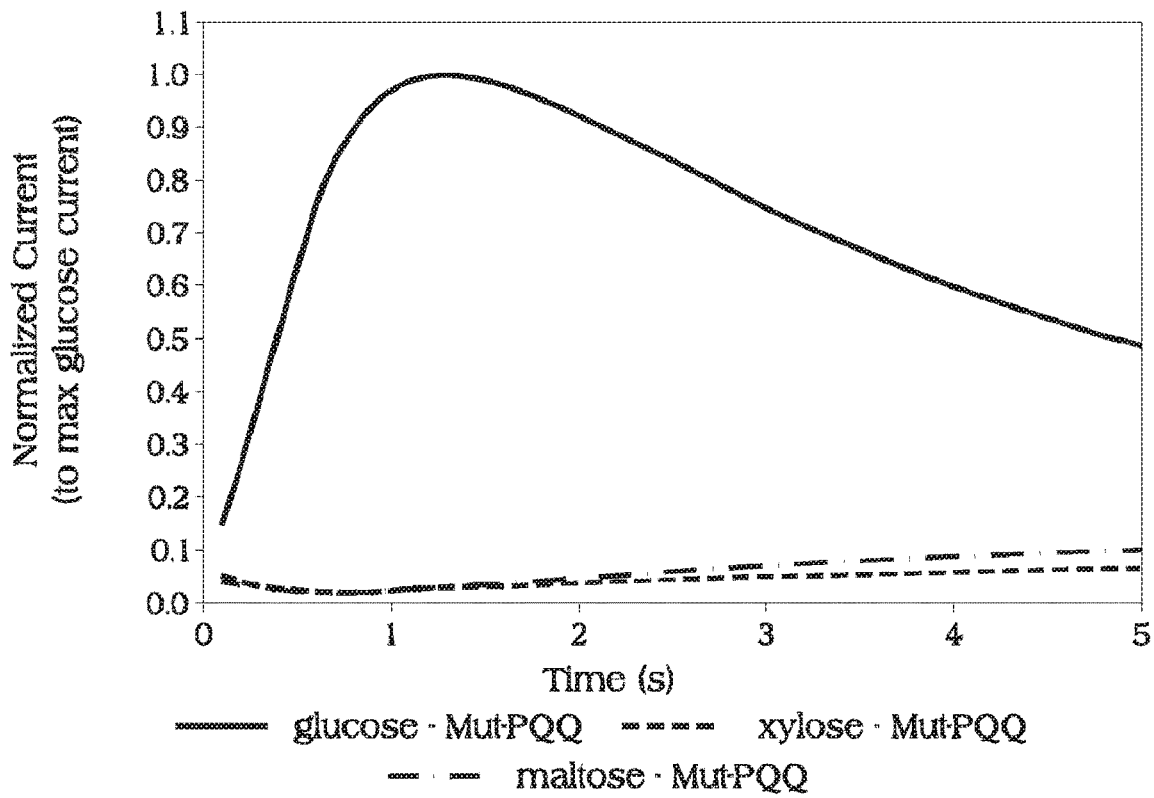
FIGS. 12A-B show results of cross-talk experiments in which dual glucose detection reagents were deposited via inkjet printing instead of slot-die coating or PictoJet discrete dispensing, which were does with samples containing 350 mg/dL glucose, 350 mg/dL maltose, or 350 mg/dL xylose. Specifically.

Results:

FIG. 12A shows response of 350 mg/dL glucose, 350 mg/dL maltose, or 350 mg/dL xylose on the electrode having the mutant PQQ-GDH with low maltose sensitivity. No significant xylose response was seen on the electrode with mutant PQQ-GDH. If there was cross-talk caused by the FAD-GDH reagent, one would have expected to see significant xylose response.

Figure 12B:
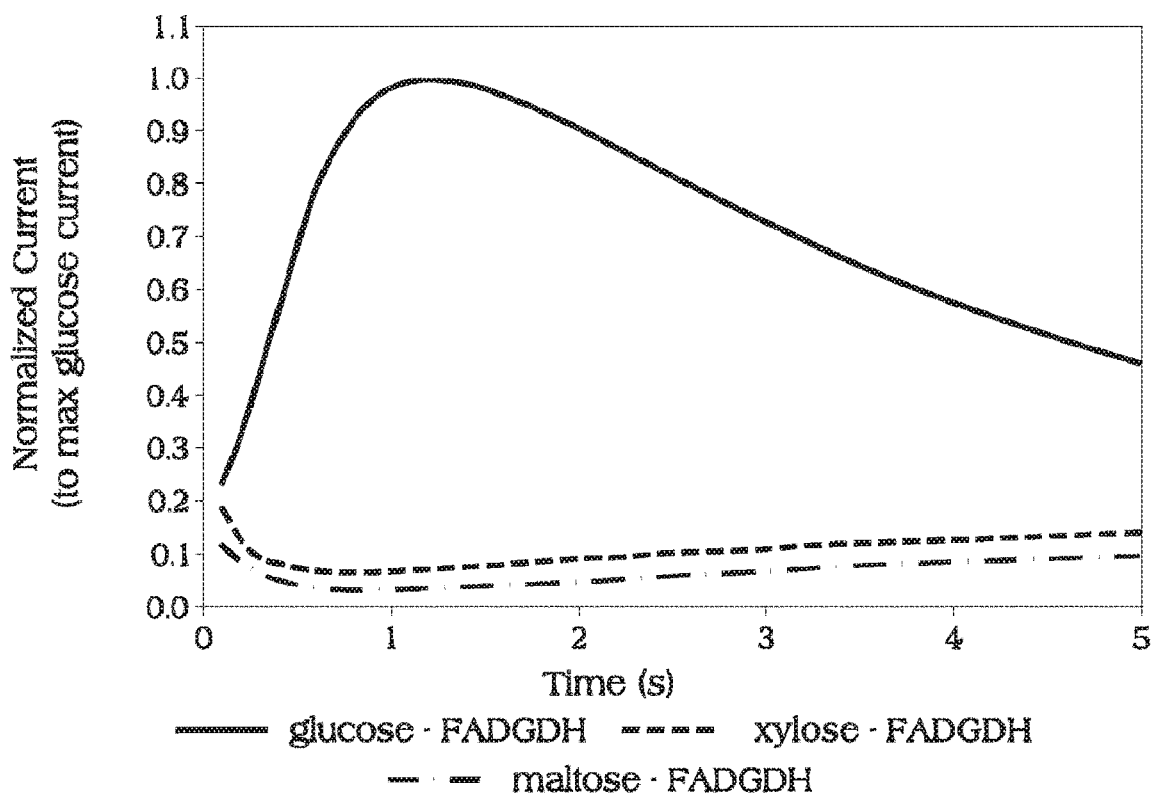

FIG. 12B shows response of 350 mg/dL glucose, 350 mg/dL maltose, and 350 mg/dL xylose on the FAD-GDH electrode. Minimal maltose response was observed on the FAD-GDH electrode. Some signal due to xylose was observed, which was expected due to the xylose interference with FAD-GDH.

All of the patents, patent applications, patent application publications and other publications recited herein are hereby incorporated by reference as if set forth in their entirety.

The present inventive concept has been described in connection with what are presently considered to be the most practical and preferred embodiments. However, the inventive concept has been presented by way of illustration and is not intended to be limited to the disclosed embodiments. Accordingly, one of skill in the art will realize that the inventive concept is intended to encompass all modifications and alternative arrangements within the spirit and scope of the inventive concept as set forth in the appended claims. Numbered embodiments are presented below.

Numbered Embodiments

In addition or as an alternative to the above, the following embodiments are described:

1. A reagent system for detecting multiple analytes, comprising:

a first detection reagent for detecting a first analyte comprising a first coenzyme-dependent enzyme or a substrate for the first enzyme, a first coenzyme, and a first mediator; and a second detection reagent for detecting a second analyte comprising a second coenzyme-dependent enzyme or a substrate for the second enzyme, a second coenzyme, and a second mediator, wherein the second mediator is distinct from the first mediator, and the first and second mediators are selected to facilitate use of the reagent system on a diagnostic test element comprising a single counter electrode utilized in measurement of both the first analyte and the second analyte.

2. The reagent system of Embodiment 1, wherein the first coenzyme-dependent enzyme and the second coenzyme-dependent enzyme are selected from the group consisting of an alcohol dehydrogenase, a glucose dehydrogenase, a glucose-6-phosphate dehydrogenase, a glucose oxidase, a glycerol dehydrogenase, a hydroxybutyrate dehydrogenase, a malate dehydrogenase, a sorbitol dehydrogenase, an amino acid dehydrogenase comprising L-amino acid dehydrogenase, and a flavin adenine dinucleotide (FAD)-, nicotinamide adenine dinucleotide (NAD)- or pyrroloquinolinequinone (PQQ)-dependent oxidase or dehydrogenase.

3. The reagent system of Embodiment 2, wherein the first coenzyme-dependent enzyme is glucose dehydrogenase, glucose-6-phospate dehydrogenase, or glucose oxidase.

4. The reagent system of Embodiment 2, wherein the second coenzyme-dependent enzyme is hydroxybutyrate dehydrogenase.

5. The reagent system of Embodiment 2, wherein the first coenzyme-dependent enzyme is glucose dehydrogenase and the second coenzyme-dependent enzyme is hydroxybutyrate dehydrogenase.

6. The reagent system of Embodiment 4, wherein the first coenzyme-dependent enzyme is glucose dehydrogenase or glucose oxidase.

7. The reagent system of Embodiment 1, wherein the first coenzyme and the second coenzyme are selected from the group consisting of a flavin adenine dinucleotide (FAD), a nicotinamide adenine dinucleotide (NAD), a pyrroloquinoline-quinone (PQQ), a thio-NAD, a thio-NADP, a PQQ, or an artificial coenzyme such as a compound according to formula (I) or a salt or a reduced form thereof, and wherein the compound according to formula (I) is as follows:

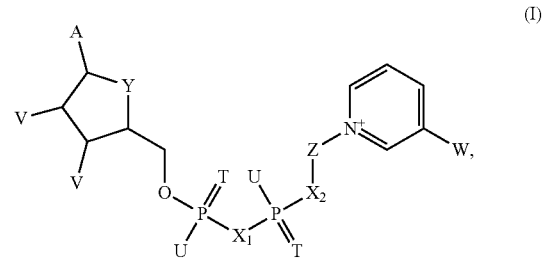

(I)

in which:

A=adenine or an analog thereof,

T=in each case independently denotes O or S,

U=in each case independently denotes OH, SH, $BH_3^-$, or $BCNH_2^-$,

V=in each case independently denotes OH or a phosphate group,

W=COOR, CON(R)$_2$, COR, or CSN(R)$_2$ in which R in each case independently denotes H or C$_1$-C$_2$-alkyl, X$_1$, X$_2$=in each case independently denote O, CH$_2$, CHCH$_3$, C(CH$_3$)$_2$, NH, or NCH$_3$, Y=NH, S, O, or CH$_2$, Z=a residue comprising a cyclic group with 5 C atoms which optionally contains a heteroatom selected from O, S and N and optionally one or more substituents, and a residue CR4$_2$ wherein CR4$_2$ is bound to the cyclic group and to X$_2$, and where R4=in each case independently denotes H, F, Cl, or CH$_3$, provided that Z and the pyridine residue are not linked by a glycosidic bond, or a salt or optionally a reduced form thereof.

8. The reagent system of Embodiment 7, wherein the first coenzyme is FAD, NAD, NADP, or the compound according to formula (I) or a salt or optionally a reduced form thereof.

9. The reagent system of Embodiment 7, wherein the first coenzyme is FAD.

10. The reagent system of Embodiment 7, wherein the second coenzyme is carba-NAD, carba-NADP, thio-NAD, or thio-NADP.

11. The reagent system of Embodiment 7, wherein the first coenzyme is FAD and the second coenzyme is carba-NAD.

12. The reagent system of Embodiment 7, wherein both the first coenzyme and the second coenzyme are carba-NAD or PQQ.

13. The reagent system of Embodiment 1, wherein the first mediator and the second mediator are selected from the group consisting of an azo compound or an azo precursor, benzoquinone, meldola blue, a nitrosoaniline or a nitrosoaniline-based precursor, a phenazine or a phenazine-based precursor, a quinone or a quinone derivative, a thiazine or a thiazine derivative, a transition metal complex such as potassium ferricyanide and osmium derivatives, and a combination of a phenazine/phenazine-based precursor and hexaammineruthenium chloride, as well as derivatives thereof.

14. The reagent system of Embodiment 13, wherein the first mediator is a nitrosoaniline derivative or nitrosoaniline-based precursor, ferricyanide, ruthenium hexamine, or phenazine.

15. The reagent system of Embodiment 14, wherein the first mediator is N,N-bis(hydroxyethyl)-3-methoxy-4-nitrosoaniline hydrochloride.

16. The reagent system of Embodiment 13, wherein the second mediator is medola blue, a phenazine or phenazine-based precursor, or a quinone or a quinone derivative.

17. The reagent system of Embodiment 16, wherein the second mediator is 1-(3-carboxy-propionylamino)-5-ethyl-phenazin-5-ium.

18. The reagent system of Embodiment 1, wherein the first mediator is N,N-bis(hydroxyethyl)-3-methoxy-4-nitrosoaniline hydrochloride and the second mediator is 1-(3-carboxy-propionylamino)-5-ethyl-phenazin-5-ium.

19. The reagent system of Embodiment 1, wherein the concentration of the second mediator is less than the concentration of the first mediator.

20. The reagent system of Embodiment 1, wherein the first coenzyme-dependent enzyme is FAD-dependent glucose dehydrogenase, the first coenzyme is FAD, and the first mediator is N,N-bis(hydroxyethyl)-3-methoxy-4-nitrosoaniline hydrochloride, and wherein the second coenzyme-dependent enzyme is hydroxybutyrate dehydrogenase, the second coenzyme is carba-NAD, carba-NADP, thio-NAD or thio-NADP, and the second mediator is 1-(3-carboxy-propionylamino)-5-ethyl-phenazin-5-ium.

21. The reagent system of Embodiment 1, wherein the first coenzyme-dependent enzyme is FAD-dependent glucose dehydrogenase, the first coenzyme is FAD, and the first mediator is N, N-bis(hydroxyethyl)-3-methoxy-4-nitrosoaniline hydrochloride (NA1144), and wherein the second coenzyme-dependent enzyme is FAD-dependent glucose dehydrogenase or a glucose oxidase, the second coenzyme is FAD or PQQ, and the second mediator is a ferricyanide or a nitrosoaniline other than NA1144 as the mediator.

22. The reagent system of Embodiment 1, wherein the first coenzyme-dependent enzyme and the first coenzyme are covalently or ionically bonded to one another.

23. The reagent system of Embodiment 1, wherein the second coenzyme-dependent enzyme and the second coenzyme are covalently or ionically bonded to one another.

24. A diagnostic test element for detecting a plurality of analytes, comprising:

a cover;

a non-conductive substrate comprising a capillary channel defined thereon and formed in part with the cover at a first end of the non-conductive substrate;

a plurality of electrodes provided on the non-conductive substrate, the electrodes including a first working electrode including at least a portion thereof positioned in the capillary channel, a second working electrode including at least a portion thereof positioned in the capillary channel, and a single counter electrode associated with the first working electrode and the second working electrode and utilized in measurement of both a first analyte and a second analyte;

a first detection reagent for detecting the first analyte comprising a first coenzyme-dependent enzyme or a substrate for the first enzyme, a first coenzyme, and a first mediator; and a second detection reagent for detecting the second analyte comprising a second coenzyme-dependent enzyme or a substrate for the second enzyme, a second coenzyme, and a second mediator;

wherein the first detection reagent is positioned relative to the first working electrode and the counter electrode in an arrangement facilitating measurement of the first analyte with the first working electrode and the counter electrode, and the second detection reagent is positioned relative to the second working electrode and the counter electrode in an arrangement facilitating measurement of the second analyte with the second working electrode and the counter electrode.

25. The diagnostic test element of Embodiment 24, further comprising a spacer positioned between the cover and the non-conductive substrate, wherein the spacer comprises an edge defining a boundary of the capillary channel and extending between opposite side edges of the non-conductive substrate, and the capillary channel comprises an inlet at the first end of the non-conductive substrate.

26. The diagnostic test element of Embodiment 24, further comprising a first counter electrode lead electrically connecting the first working electrode to a first working electrode pad, a second electrode lead electrically connecting the second working electrode to a second working electrode pad, and a counter electrode lead electrically connecting the counter electrode to a counter electrode pad.

27. The diagnostic test element of Embodiment 24, further comprising at least two sample sufficiency electrodes disposed on the non-conductive substrate, each one of the sample sufficiency electrodes being positioned along a respective side edge of the non-conductive substrate.

28. The diagnostic test element of Embodiment 24, where the first working electrode has a working area that is equivalent to a working area of the second electrode.

29. The diagnostic test element of Embodiment 24, wherein the first working electrode has a working area that is less than a working area of the second working electrode.

30. A test system comprising:
   a test meter configured to analyze a body fluid sample; and
   one or more diagnostic test elements of Embodiment 24.

31. A method of electrochemically measuring concentration or presence of one or more analytes of interest in a body fluid sample, the method comprising the steps of:
   applying a body fluid sample having or suspected of having the one or more analytes of interest to a diagnostic test element of Embodiment 24 so that the body fluid sample is in fluidic contact with the dry detection reagent to hydrate the dry detection reagent;
   applying a electrical test sequence to the diagnostic test element via a test meter configured to interact with the diagnostic test element, wherein the test sequence comprises:
   a. a first fixed direct current (DC) component comprising a potential difference applied between the counter electrode and the first working electrode to measure a first analyte of interest; and
   b. a second fixed DC component comprising a potential difference applied between the counter electrode and the second working electrode to measure a second analyte of interest;
   measuring response information to each component of the electrical test sequence with the test meter; and
   determining one or more analyte concentrations with the test meter using the response information.

32. The method of Embodiment 31, wherein the electrical test sequence further comprises a delay after applying the body fluid sample to the diagnostic test element to allow the body fluid sample to hydrate the dry detection reagent, and wherein the delay comprises an open or near 0 V potential difference maintained between the counter electrode and the first working electrode as well as between the counter electrode and the second working electrode.

33. The method of Embodiment 31, wherein the electrical test sequence further comprises between the first fixed DC component and the second fixed DC component, a near 0 V DC potential difference maintained between the counter electrode and the first working electrode to allow a response current to return to 0.

34. The method of Embodiment 31, wherein the first fixed DC component is a plurality of potential pulses ramped to or from about 0 V to about +450 mV with each pulse being separated by a recovery interval during which about a 0 mV potential difference is applied between the counter electrode and the first working electrode, wherein the second fixed DC component follows a final recovery interval and is an about +175 mV potential difference applied between the counter electrode and the second working electrode, wherein the pulses and recovery intervals of the first fixed DC component are each for about 50 msec to about 500 msec, and wherein the second fixed DC component is for at least about 500 msec.

35. The method of Embodiment 31, wherein the first fixed DC component is a plurality of potential pulses ramped to or from about 0 V to about +450 mV with each pulse being separated by a recovery interval during which about a 0 mV potential difference is applied between the counter electrode and the first working electrode, wherein the second fixed DC component follows a final recovery interval and is a plurality of potential pulses ramped to or from about 0 mV to about +175 mV with each pulse being separated by a recovery interval during which about a 0 mV potential difference is applied between the counter electrode and the second working electrode, wherein the pulses and recovery intervals of the first fixed DC component and the second fixed DC component are each for about 50 msec to about 500 msec.

36. The method of Embodiment 34, wherein the potential pulses of the first fixed DC component are ramped for about 10 msec.

37. The method of Embodiment 31, wherein the electrical test sequence further comprises a third fixed DC component, the third fixed DC component comprising a plurality of potential pulses that alternates between about −450 mV to about +450 mV, and wherein the third fixed DC component is applied between the first fixed DC component and the second fixed DC component.

38. The method of Embodiment 31, wherein the electrical test sequence further comprises an alternating current (AC) component, the AC component comprising a plurality of low-amplitude AC signals.

39. The method of Embodiment 38, wherein the AC component comprises frequencies of about 10 kHz, about 20 kHz, about 10 kHz, about 2 kHz and about 1 kHz, and wherein each frequency is applied for about 0.5 seconds to about 1.5 seconds.

40. The method of Embodiment 38, wherein the AC component comprises frequencies of about 20 kHz, about 10 kHz, about 2 kHz and about 1 kHz, and wherein each frequency is applied for about 0.5 seconds to about 1.5 seconds.

41. The method of Embodiment 38, wherein the AC component is applied prior to the first fixed DC component and the second fixed component.

42. The method of Embodiment 31, wherein the electrical test sequence further comprises a burn-off interval during which a positive potential difference is applied between the counter electrode and the first working electrode and optionally between the counter electrode and the second working electrode to reduce an amount of reduced mediator present in the detection reagent prior to a significant contribution from the one or more analytes of interest, wherein the burn-off interval is applied for about 0.5 seconds to about 1.0 seconds.

43. The method of Embodiment 31 further comprising the step of adjusting a treatment or modifying a diet based upon the one or more analyte concentrations.

44. The method of Embodiment 31 further comprising the step of transmitting a message to at least one of a user of the test element, healthcare provider, caregiver, and parent or guardian to adjust a treatment or modify a diet based upon the one or more analyte concentrations.

45. The method of Embodiment 31, wherein the first analyte is glucose and the second analyte is hydroxybutyrate.

46. The method of Embodiment 45, wherein the first coenzyme-dependent enzyme is FAD-dependent glucose dehydrogenase, the first coenzyme is FAD, and the first mediator is N,N-bis(hydroxyethyl)-3-methoxy-4-nitrosoaniline hydrochloride, and wherein the second coenzyme-dependent enzyme is hydroxybutyrate dehydrogenase, the second coenzyme is carba-NAD, carba-NADP, thio-NAD or thio-NADP, and the second mediator is 1-(3-carboxy-propionylamino)-5-ethyl-phenazin-5-ium.

47. The method of Embodiment 45, wherein the first coenzyme-dependent enzyme is FAD-dependent glucose dehydrogenase, the first coenzyme is FAD, and the first mediator is N,N-bis(hydroxyethyl)-3-methoxy-4-nitrosoaniline hydrochloride (NA1144), and wherein the second coenzyme-dependent enzyme is FAD-dependent glucose dehydrogenase or a glucose oxidase, the second coenzyme is FAD or PQQ, and the second mediator is a ferricyanide or a nitrosoaniline other than NA1144 as the mediator.

48. A dry detection reagent as substantially described and shown herein.

49. A diagnostic test element as substantially described and shown herein.

50. A test system as substantially described and shown herein.

51. A method of electrochemically measuring concentration or presence of one or more analytes of interest in a body fluid sample as substantially described and shown herein.

LISTING OF REFERENCE NUMBERS 10 diagnostic test element
12 support substrate
14 spacer
16 cover
18 first surface
20 second surface
22 first end
24 second end
26 side edge
28 side edge
30 capillary channel
32 end edge
34 inner surface
36 lower surface
38 meter
40 test element port
42 display
44 entry means

What is claimed is:

1. A reagent system for detecting multiple analytes, comprising:
    a first detection reagent for detecting a first analyte comprising a first coenzyme-dependent enzyme or a substrate for the first enzyme, a first coenzyme, and a first mediator; and
    a second detection reagent for detecting a second analyte comprising a second coenzyme-dependent enzyme or a substrate for the second enzyme, a second coenzyme, and a second mediator, wherein the second mediator is distinct from the first mediator, and the first and second mediators are selected to facilitate use of the reagent system on a diagnostic test element comprising a single counter electrode utilized in measurement of both the first analyte and the second analyte;
    wherein the second coenzyme-dependent enzyme and the second coenzyme are covalently or ionically bonded to one another.

2. The reagent system of claim 1, wherein the first coenzyme-dependent enzyme and the second coenzyme-dependent enzyme are selected from the group consisting of an alcohol dehydrogenase, a glucose dehydrogenase, a glucose-6-phosphate dehydrogenase, a glucose oxidase, a glycerol dehydrogenase, a hydroxybutyrate dehydrogenase, a malate dehydrogenase, a sorbitol dehydrogenase, an amino acid dehydrogenase comprising L-amino acid dehydrogenase, and a flavin adenine dinucleotide (FAD)-, nicotinamide adenine dinucleotide (NAD)- or pyrroloquinoline-quinone (PQQ)-dependent oxidase or dehydrogenase.

3. The reagent system of claim 2, wherein the first coenzyme-dependent enzyme is glucose dehydrogenase, glucose-6-phospate dehydrogenase, or glucose oxidase.

4. The reagent system of claim 2, wherein the second coenzyme-dependent enzyme is hydroxybutyrate dehydrogenase.

5. The reagent system of claim 4, wherein the first coenzyme-dependent enzyme is glucose dehydrogenase or glucose oxidase.

6. The reagent system of claim 2, wherein the first coenzyme-dependent enzyme is glucose dehydrogenase and the second coenzyme-dependent enzyme is hydroxybutyrate dehydrogenase.

7. The reagent system of claim 1, wherein the first coenzyme and the second coenzyme are selected from the group consisting of a flavin adenine dinucleotide (FAD), a nicotinamide adenine dinucleotide (NAD), a pyrroloquinoline-quinone (PQQ), a thio-NAD, a thio-NADP, a PQQ, or an artificial coenzyme such as a compound according to formula (I) or a salt or a reduced form thereof, and wherein the compound according to formula (I) is as follows:

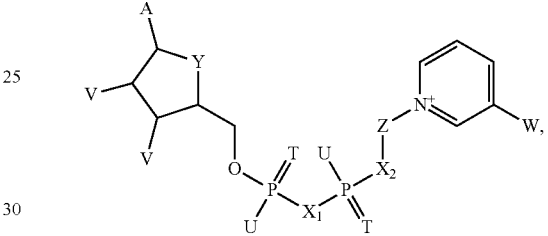

in which:
    A=adenine or an analog thereof,
    T=in each case independently denotes O or S,
    U=in each case independently denotes OH, SH, $BH_3^-$, or $BCNH_2^-$,
    V=in each case independently denotes OH or a phosphate group,
    W=COOR, $CON(R)_2$, COR, or $CSN(R)_2$ in which R in each case independently denotes H or $C_1$-$C_2$-alkyl,
    $X_1$, $X_2$=in each case independently denote O, $CH_2$, $CHCH_3$, $C(CH_3)_2$, NH, or $NCH_3$,
    Y=NH, S, O, or $CH_2$,
    Z=a residue comprising a cyclic group with 5 C atoms which optionally contains a heteroatom selected from O, S and N and optionally one or more substituents, and a residue $CR4_2$ wherein $CR4_2$ is bound to the cyclic group and to $X_2$, and
    where R4=in each case independently denotes H, F, Cl, or $CH_3$, provided that Z and the pyridine residue are not linked by a glycosidic bond,
    or a salt or optionally a reduced form thereof.

8. The reagent system of claim 7, wherein the first coenzyme is FAD, NAD, NADP, or the compound according to formula (I) or a salt or optionally a reduced form thereof.

9. The reagent system of claim 7, wherein the first coenzyme is FAD.

10. The reagent system of claim 7, wherein the second coenzyme is carba-NAD, carba-NADP, thio-NAD, or thio-NADP.

11. The reagent system of claim 7, wherein the first coenzyme is FAD and the second coenzyme is carba-NAD.

12. The reagent system of claim 7, wherein both the first coenzyme and the second coenzyme are carba-NAD or PQQ.

13. The reagent system of claim 1, wherein the first mediator and the second mediator are selected from the group consisting of an azo compound or an azo precursor, benzoquinone, meldola blue, a nitrosoaniline or a nitrosoaniline-based precursor, a phenazine or a phenazine-based precursor, a quinone or a quinone derivative, a thiazine or a thiazine derivative, a transition metal complex such as potassium ferricyanide and osmium derivatives, and a combination of a phenazine/phenazine-based precursor and hexaammineruthenium chloride, as well as derivatives thereof.

14. The reagent system of claim 13, wherein the first mediator is a nitrosoaniline derivative or nitrosoaniline-based precursor, ferricyanide, ruthenium hexamine, or phenazine.

15. The reagent system of claim 14, wherein the first mediator is N,N-bis(hydroxyethyl)-3-methoxy-4-nitrosoaniline hydrochloride.

16. The reagent system of claim 13, wherein the second mediator is medola blue, a phenazine or phenazine-based precursor, or a quinone or a quinone derivative.

17. The reagent system of claim 16, wherein the second mediator is 1-(3-carboxy-propionylamino)-5-ethyl-phenazin-5-ium.

18. The reagent system of claim 1, wherein the first mediator is N,N-bis(hydroxyethyl)-3-methoxy-4-nitrosoaniline hydrochloride and the second mediator is 1-(3-carboxy-propionylamino)-5-ethyl-phenazin-5-ium.

19. The reagent system of claim 1, wherein the concentration of the second mediator is less than the concentration of the first mediator.

20. The reagent system of claim 1, wherein the first coenzyme-dependent enzyme is FAD-dependent glucose dehydrogenase, the first coenzyme is FAD, and the first mediator is N,N-bis(hydroxyethyl)-3-methoxy-4-nitrosoaniline hydrochloride, and wherein the second coenzyme-dependent enzyme is hydroxybutyrate dehydrogenase, the second coenzyme is carba-NAD, carba-NADP, thio-NAD or thio-NADP, and the second mediator is 1-(3-carboxy-propionylamino)-5-ethyl-phenazin-5-ium.

21. The reagent system of claim 1, wherein the first coenzyme-dependent enzyme and the first coenzyme are covalently or ionically bonded to one another.

22. A method of electrochemically measuring concentration or presence of one or more analytes of interest in a body fluid sample, the method comprising the steps of:
   applying a body fluid sample having or suspected of having the one or more analytes of interest to a diagnostic test element so that the body fluid sample is in fluidic contact with a detection reagent to hydrate the detection reagent, wherein the diagnostic test element includes:
      a cover;
      a non-conductive substrate comprising a capillary channel defined thereon and formed in part with the cover at a first end of the non-conductive substrate;
      a plurality of electrodes provided on the non-conductive substrate, the electrodes including a first working electrode including at least a portion thereof positioned in the capillary channel, a second working electrode including at least a portion thereof positioned in the capillary channel, and a single counter electrode associated with the first working electrode and the second working electrode and utilized in measurement of both a first analyte and a second analyte;
      a first detection reagent for detecting the first analyte comprising a first coenzyme-dependent enzyme or a substrate for the first enzyme, a first coenzyme, and a first mediator; and
      a second detection reagent for detecting the second analyte comprising a second coenzyme-dependent enzyme or a substrate for the second enzyme, a second coenzyme, and a second mediator;
      wherein the first detection reagent is positioned relative to the first working electrode and the counter electrode in an arrangement facilitating measurement of the first analyte with the first working electrode and the counter electrode, and the second detection reagent is positioned relative to the second working electrode and the counter electrode in an arrangement facilitating measurement of the second analyte with the second working electrode and the counter electrode;
   applying an electrical test sequence to the diagnostic test element via a test meter configured to interact with the diagnostic test element, wherein the test sequence comprises:
      a. a first fixed direct current (DC) component comprising a potential difference applied between the counter electrode and the first working electrode to measure a first analyte of interest; and
      b. a second fixed DC component comprising a potential difference applied between the counter electrode and the second working electrode to measure a second analyte of interest;
   measuring response information to each component of the electrical test sequence with the test meter; and
   determining one or more analyte concentrations with the test meter using the response information;
   wherein the first analyte is glucose and the second analyte is hydroxybutyrate; and
   wherein the first coenzyme-dependent enzyme is FAD-dependent glucose dehydrogenase, the first coenzyme is FAD, and the first mediator is N,N-bis(hydroxyethyl)-3-methoxy-4-nitrosoaniline hydrochloride (NA1144), and wherein the second coenzyme-dependent enzyme is FAD-dependent glucose dehydrogenase or a glucose oxidase, the second coenzyme is FAD or PQQ, and the second mediator is a ferricyanide or a nitrosoaniline other than NA1144 as the mediator.

23. The method of claim 22, wherein the electrical test sequence further comprises a delay after applying the body fluid sample to the diagnostic test element to allow the body fluid sample to hydrate the dry detection reagent, and wherein the delay comprises an open or near 0 V potential difference maintained between the counter electrode and the first working electrode as well as between the counter electrode and the second working electrode.

24. The method of claim 22, wherein the electrical test sequence further comprises between the first fixed DC component and the second fixed DC component, a near 0 V DC potential difference maintained between the counter electrode and the first working electrode to allow a response current to return to 0.

25. The method of claim 22, wherein the first fixed DC component is a plurality of potential pulses ramped to or from about 0 V to about +450 mV with each pulse being separated by a recovery interval during which about a 0 mV potential difference is applied between the counter electrode and the first working electrode, wherein the second fixed DC component follows a final recovery interval and is an about +175 mV potential difference applied between the counter electrode and the second working electrode, wherein the pulses and recovery intervals of the first fixed DC component are each for about 50 msec to about 500 msec, and wherein the second fixed DC component is for at least about 500 msec.

26. The method of claim 25, wherein the potential pulses of the first fixed DC component are ramped for about 10 msec.

27. The method of claim 22, wherein the first fixed DC component is a plurality of potential pulses ramped to or from about 0 V to about +450 mV with each pulse being separated by a recovery interval during which about a 0 mV potential difference is applied between the counter electrode and the first working electrode, wherein the second fixed DC component follows a final recovery interval and is a plurality of potential pulses ramped to or from about 0 mV to about +175 mV with each pulse being separated by a recovery interval during which about a 0 mV potential difference is applied between the counter electrode and the second working electrode, wherein the pulses and recovery intervals of the first fixed DC component and the second fixed DC component are each for about 50 msec to about 500 msec.

28. The method of claim 22, wherein the electrical test sequence further comprises a third fixed DC component, the third fixed DC component comprising a plurality of potential pulses that alternates between about −450 mV to about +450 mV, and wherein the third fixed DC component is applied between the first fixed DC component and the second fixed DC component.

29. The method of claim 22, wherein the electrical test sequence further comprises a burn-off interval during which a positive potential difference is applied between the counter electrode and the first working electrode and optionally between the counter electrode and the second working electrode to reduce an amount of reduced mediator present in the detection reagent prior to a significant contribution from the one or more analytes of interest, wherein the burn-off interval is applied for about 0.5 seconds to about 1.0 seconds.

30. The method of claim 22 further comprising the step of adjusting a treatment or modifying a diet based upon the one or more analyte concentrations.

31. The method of claim 22 further comprising the step of transmitting a message to at least one of a user of the test element, healthcare provider, caregiver, and parent or guardian to adjust a treatment or modify a diet based upon the one or more analyte concentrations.

32. The method of claim 22, wherein the electrical test sequence further comprises an alternating current (AC) component, the AC component comprising a plurality of low-amplitude AC signals.

33. The method of claim 32, wherein the AC component comprises frequencies of about 10 kHz, about 20 kHz, about 10 kHz, about 2 kHz and about 1 kHz, and wherein each frequency is applied for about 0.5 seconds to about 1.5 seconds.

34. The method of claim 32, wherein the AC component comprises frequencies of about 20 kHz, about 10 kHz, about 2 kHz and about 1 kHz, and wherein each frequency is applied for about 0.5 seconds to about 1.5 seconds.

35. The method of claim 32, wherein the AC component is applied prior to the first fixed DC component and the second fixed component.

36. A reagent system for detecting multiple analytes, comprising:
a first detection reagent for detecting a first analyte comprising a first coenzyme-dependent enzyme or a substrate for the first enzyme, a first coenzyme, and a first mediator; and
a second detection reagent for detecting a second analyte comprising a second coenzyme-dependent enzyme or a substrate for the second enzyme, a second coenzyme, and a second mediator, wherein the second mediator is distinct from the first mediator, and the first and second mediators are selected to facilitate use of the reagent system on a diagnostic test element comprising a single counter electrode utilized in measurement of both the first analyte and the second analyte;
wherein the first coenzyme-dependent enzyme is FAD-dependent glucose dehydrogenase, the first coenzyme is FAD, and the first mediator is N,N-bis(hydroxyethyl)-3-methoxy-4-nitrosoaniline hydrochloride (NA1144), and wherein the second coenzyme-dependent enzyme is FAD-dependent glucose dehydrogenase or a glucose oxidase, the second coenzyme is FAD or PQQ, and the second mediator is a ferricyanide or a nitrosoaniline other than NA1144 as the mediator.

* * * * *